(12) United States Patent
Gudkov et al.

(10) Patent No.: US 9,006,180 B2
(45) Date of Patent: *Apr. 14, 2015

(54) METHODS FOR TREATING TOURNIQUET-INDUCED INJURIES

(71) Applicants: Cleveland BioLabs, Inc., Buffalo, NY (US); Cleveland Clinic Foundation, Cleveland, OH (US)

(72) Inventors: Andrei Gudkov, East Aurora, NY (US); Robert Fairchild, Mayfield Village, OH (US)

(73) Assignees: Cleveland BioLabs, Inc., Buffalo, NY (US); Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/088,097

(22) Filed: Nov. 22, 2013

(65) Prior Publication Data

US 2014/0220037 A1 Aug. 7, 2014

Related U.S. Application Data

(63) Continuation of application No. 13/530,580, filed on Jun. 22, 2012, now Pat. No. 8,618,059, which is a continuation of application No. 13/056,973, filed as application No. PCT/US2009/052493 on Jul. 31, 2009, now Pat. No. 8,324,163.

(60) Provisional application No. 61/085,766, filed on Aug. 1, 2008.

(51) Int. Cl.
| | |
|---|---|
| *A61P 39/06* | (2006.01) |
| *C07K 16/28* | (2006.01) |
| *A61K 31/355* | (2006.01) |
| *A61K 31/661* | (2006.01) |
| *A61K 38/16* | (2006.01) |
| *A61K 45/06* | (2006.01) |
| *C07K 14/195* | (2006.01) |
| *A61B 17/00* | (2006.01) |

(52) U.S. Cl.
CPC .............. *C07K 16/28* (2013.01); *A61K 31/355* (2013.01); *A61K 31/661* (2013.01); *A61K 38/164* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,554,101 | A | 11/1985 | Hopp |
| 5,399,494 | A | 3/1995 | Kaper et al. |
| 5,693,476 | A | 12/1997 | Scheller |
| 6,130,082 | A | 10/2000 | Majarian et al. |
| 7,638,485 | B2 | 12/2009 | Gudkov |
| 7,794,731 | B2 | 9/2010 | Mizel et al. |
| 8,007,812 | B2 | 8/2011 | Gudkov et al. |
| 8,106,005 | B2 | 1/2012 | Gudkov |
| 8,287,882 | B2 | 10/2012 | Gudkov et al. |
| 8,324,163 | B2 | 12/2012 | Gudkov et al. |
| 8,580,321 | B2 | 11/2013 | Gudkov et al. |
| 8,618,059 | B2 * | 12/2013 | Gudkov et al. .............. 514/15.1 |
| 2002/0009747 | A1 | 1/2002 | Miller et al. |
| 2003/0044429 | A1 | 3/2003 | Aderem et al. |
| 2005/0147627 | A1 | 7/2005 | Aderem et al. |
| 2005/0266391 | A1 | 12/2005 | Bennett et al. |
| 2006/0275255 | A1 | 12/2006 | Gudkov |
| 2007/0202551 | A1 | 8/2007 | Gudkov |
| 2007/0269406 | A1 | 11/2007 | Ichim |
| 2008/0124361 | A1 | 5/2008 | Mizel et al. |
| 2008/0182797 | A1 | 7/2008 | Nudler et al. |
| 2009/0011982 | A1 | 1/2009 | Gudkov et al. |
| 2009/0081157 | A1 | 3/2009 | Kornbluth et al. |
| 2009/0123467 | A1 | 5/2009 | Bedi et al. |
| 2009/0175880 | A1 | 7/2009 | Keler et al. |
| 2009/0246303 | A1 | 10/2009 | Gudkov et al. |
| 2010/0056454 | A1 | 3/2010 | Gudkov |
| 2011/0319595 | A1 | 12/2011 | Gudkov et al. |
| 2013/0004515 | A1 | 1/2013 | Gudkov et al. |
| 2013/0324462 | A1 | 12/2013 | Gudkov et al. |

FOREIGN PATENT DOCUMENTS

| | | |
|---|---|---|
| WO | WO 92/05816 | 4/1992 |
| WO | WO 93/18150 | 9/1993 |
| WO | WO 99/29312 | 6/1999 |
| WO | WO 01/40280 | 6/2001 |
| WO | WO 01/55210 | 8/2001 |
| WO | WO 02/44363 | 6/2002 |
| WO | WO 03/027251 | 4/2003 |
| WO | WO 03/028659 | 4/2003 |
| WO | WO 2004/086039 | 10/2004 |
| WO | WO 2005/056041 | 6/2005 |
| WO | WO 2005/056042 | 6/2005 |
| WO | WO 2005/056054 | 6/2005 |
| WO | WO 2005/056055 | 6/2005 |
| WO | WO 2005/057218 | 6/2005 |

(Continued)

OTHER PUBLICATIONS

Alavanja, M. CR., "Biologic damage resulting from exposure to tobacco smoke from radon: implication for preventive interventions," Oncogene, 21:7365-7375 (2002).

Andreassen, C. N. et al., "Chemical radioprotection: a critical review of amifostine as a cytoprotector in radiotherapy," Seminars in Radiation Oncology, 13(1):62-72 (2003).

Androstenediol and Androstenedione, Wikipedia (online). URL: < http://en.wikipedia.org/wiki/Androstenediol>, [Retrieved from the Internet: Dec. 5, 2006], 4 pages.

(Continued)

*Primary Examiner* — Zachary Howard

(74) *Attorney, Agent, or Firm* — Morgan, Lewis & Bockius LLP

(57) ABSTRACT

The present invention relates to treating a tissue in a mammal from the effects of reperfusion using flagellin.

13 Claims, 31 Drawing Sheets

(56) References Cited

FOREIGN PATENT DOCUMENTS

| WO | WO 2006/066214 | 6/2006 |
|---|---|---|
| WO | WO 2006/069198 | 6/2006 |
| WO | WO 2007/030581 | 3/2007 |
| WO | WO 2009/102818 | 8/2009 |
| WO | WO 2011/044246 | 4/2011 |

OTHER PUBLICATIONS

Bachmann, M. F. et al., "Recall proliferation potential of memory CD8+ T cells and antiviral protection," The Journal of Immunology, 175:4677-4685 (2005).

Ben-Yedidia, T. et al., "Intranasal administration of peptide vaccine protects human/mouse radiation chimera from influenza infection," International Immunology, 11(7):1043-1051 (1998).

Booth, D. et. al., "Transforming growth factor-B3 protects murine small intestinal crypt stem cells and animal survival after irradiation, possibly by reducing stem-cell cycling," Int. J. Cancer, 86(1):53-59 (2000).

Borges, H. L. et al., "DNA damage-induced cell death: lessons from the central nervous system," Cell Research, 18:17-26 (2008).

Bulinski, J. C. et al., "Overexpression of MAP4 inhibits organelle motility and trafficking in vivo," Journal of Cell Sciences, 110:3055-3064 (1997).

Burdelya, L. G. et al., "An agonist of toll-like receptor 5 has radioprotective activity in mouse and primate models," Science, 320:226-230 (2008).

Carnes, B. A. et al., "Mortality of atomic bomb survivors predicted from laboratory animals," Radiation Research, 160(2):159-167 (2003) Abstract.

Caron, G. et. al., "Direct stimulation of human T cells via TLR5 and TLR7/8: Flagellin and R-848 up-regulate proliferation and IFN-y production by memory CD4+ T cells," The Journal of Immunology, 175(3):1551-1557 (2005).

Eaves-Pyles, T. et al., "Flagellin, a novel mediator of Salmonella-induced epithelial activation and systemic inflammation: I$\kappa$B$\alpha$ degradation, induction of nitric oxide synthase, induction of proinflammatory mediators, and cardiovascular dysfunction," The Journal of Immunology, 166(2):1248-1260 (2001).

Eaves-Pyles, T. D. et al., "Salmonella flagellin-dependent proinflammatory responses are localized to the conserved amino and carboxyl regions of the protein," The Journal of Immunology, 167(12):7009-7016 (2001).

Egan, L. J. et al., "I$\kappa$B-kinase$\beta$-dependent NF-$\kappa$B activation provides radioprotection to the intestinal epithelium," PNAS, 101(8):2452-2457 (2004).

Efferson, C. L. et al., "Stimulation of human T cells by an influenza A vector expressing a CTL epitope from the HER-2/neu protooncogene results in higher numers of antigen-specific TCR$^{hi}$ cells than stimulation with peptide. Divergent roles of IL-2 and IL-15," Anticancer Research, 25:715-724 (2005).

Elewaut, D. et al., "NF-$\kappa$B is a central regulator of the intestinal epithelial cell innate immune response induced by infection with enteroinvasive bacteria," The Journal of Immunology, 163:1457-1466 (1999).

Foldes, G. et al., "Toll-like receptor modulation in cardiovascular disease: a target for intervention?", Expert Opinion on Investigational Drugs, 15(8):857-871 (2006).

Fukuzawa, N. et al., "A TLR5 agonist inhibits acute renal ischemic failure," The Journal of Immunology, 187:3831-3839 (2011).

GenBank databases, NCBI Accession No. M84972, Apr. 26, 1993, [online], [retrieved on Sep. 29, 2011], Retrieved from the Internet: <URL: http://www.ncbi.nlm.nih.gov/nuccore/M84972>.

Gewirtz, A.T. et. al., "Cutting edge: Bacterial flagellin activates basolaterally expressed TLR5 to induce epithelial proinflammatory gene expression," The Journal of Immunology, 167(4):1882-1885 (2001).

Grdina, D. J. et al., "Relationships between cytoprotection and mutation prevention by WR-1065," Military Medicine, 167(2):51-53 (2002).

Gudkov, A. V. et al., "The role of p53 in determining sensitivity to radiotherapy," Nat. Rev. Cancer, 3:117-129 (2003).

Guan, K. L. et al., "Eukaryotic proteins expressed in Escherichia coli: an improved thrombin cleavage and purification procedure of fusion proteins with glutathione S-transferase," Analytical Biochemistry, 192:262-267 (1991).

Haimovitz-Friedman, A. et al., "Ionizing radiation acts on cellular membranes to generate ceramide and apoptosis," J. Exp. Med., 180:525-535 (1994).

Hall, "Physics and Chemisty of Radiation Absorption," Radiobiology for the Radiobiologist, pp. 5-15, 5th ed., Lippincott Williams and Wilkins, Philadelphia, PA (2000).

Herbert, J. M. et al., "Involvement of u-PA in the anti-apoptotic activity of TGF-beta for vascular smooth muscle cells," FEBS Letters, 413(3):401-404 (1997).

Honko, A. N. et al., "Effects of flagellin on innate and adaptive immunity," Immunologic Research, 33(1):83-101 (2005).

Jung, C. W. et al., "Antiproliferative effect of a vitamin D3 analog, EB1089, on HL-60 cells by the induction of TGF-beta receptor," Leukemia Research, 23(12):1105-1112 (1999).

Kemp, G. et al., "Amifostine pretreatment for protection against cyclophosphamide-induced and cisplatin-induced toxicities: results of a randomized control in patients with advanced ovarian cancer," Journal of Clinical Oncology, 14(7):2101-2112 (1996).

Kyte, J. et al., "A simple method for displaying the hydropathic character of a protein," J. Mol. Biol., 157:105-132 (1982).

Lehnert, B. E. et al., "A new mechanism for DNA alterations induced by alpha particles such as those emitted by radon and radon progeny," Environmental Health Perspectives, 105(5):1095-1101 (1997).

Li, J. et al., "Evolutionary origin and radiation of the avian-adapted non-motile salmonellae," Journal of Medical Microbiology, 38(2):129-139 (1993).

Li, G. et al., "A special issue on DNA damage responses and genome maintenance," Cell Research, 18(1):1-2 (2008).

McQuiston, J. R. et al., "Sequencing and comparative analysis of flagellin genes fliC, fljB, and flpA from Salmonella," Journal of Clinical Microbiology, 42(5):1923-1932 (2004).

Melby, T. E. et al., "The symmetrical structure of structural maintenance of chromosomes (SMC) and MukB proteins: Long, antiparallel coiled coils, folded at a flexible hinge," The Journal of Cell Biology, 142(6):1595-1604 (1998).

Mercurio, F. et al., "NF-$\kappa$B as a primary regulator of the stress response," Oncogene, 18:6163-6171 (1999).

Murley, J. S. et al., "Delayed cytoprotection after enhancement of Sod2 (MnSOD) gene expression in SA-NH mouse sarcoma cells exposed to WR-1065, the active metabolite of amifostine," Radiation Research, 158(1):101-109 (2002).

Murley, J. S. et al., "Delayed radioprotection by NF$\kappa$B-mediated induction of Sod2 (MnSOD) in SA-NH tumor cells after exposure to clinically used thiol-containing drugs," Radiation Research, 162(5):536-546 (2004).

Mutlu-Turkoglu, U. et al., "The effect of selenium and/or vitamin E treatments on radiation-induced intestinal injury in rats," Life Sciences, 66(20):1905-1913 (2000).

Neish, A. S., "TLRS in the Gut. II. Flagellin-induced inflammation and antiapoptosis," American Journal of Physiology: Gastrointestinal and Liver Physiology, 292(2):G462-G466 (2006).

Newton, S. M. C. et al., "Immune response to cholera toxin epitope inserted in Salmonella flagellin," Science, 244:70-72 (1989).

Panda, D. et al., "Stabilization of microtubule dynamics by estramustine by binding to a novel site in tubulin: A possible mechanistic basis for its antitumor action," Proc. Natl. Acad. Sci. USA, 94(20):10560-10564 (1997).

Patchen, M. L., "Amifostine plus granulocyte colony-stimulating factor therapy enhances recovery from supralethal radiation exposures: preclinical experience in animals models," European Journal of Cancer, 31A(1):S17-S21 (1995).

Samatey, F. A. et al., "Structure of the bacterial flagellar protofilament and implications for a switch for supercoiling," Nature, 410:331-337 (2001).

Satyamitra, M. et al., "In vivo postirradiation protection by a vitamin E analog, $\alpha$-TMG," Radiation Research, 160(6):655-661 (2003).

(56) References Cited

OTHER PUBLICATIONS

Sebastiani, G. et. al., "Cloning and characterization of the murine Toll-like Receptor 5 (Tlr5) gene: sequence and mRNA expression studies in *Salmonella*-susceptible MOLF/Ei mice," Genomics, 64(3):230-240 (2000).

Seed, T. et al., "New strategies for the prevention of radiation injury: possible implications for countering radiation hazards of long-term space travel," Journal of Radiation Research, 43:S239-S244 (2002).

Selander, R. K. et al., "Molecular evolutionary genetics of the cattle-adapted serovar *Salmonella* dublin," Journal of Bacteriology, 174(11):3587-3592 (1992).

Service, R. F., "Tumor-Killer Made; How Does It Work?," Science, 274:2009 (1996).

Smith, K. D. et al., "Toll-like receptor 5 recognizes a conserved site on flagellin required for protofilament formation and bacterial motility," Nature Immunology, 4(12):1247-1253 (2003).

Spadaro, J. A. et al., "Radioprotectant combinations spare radiation-induced damage to the physis more than fractionation alone," Int. J. Radiat. Biol., 81(10):759-765 (2005) Abstract.

Sredni, B. et al., "The immunomodulator AS101 administered orally as a chemoprotective and radioprotective agent," Int. J. Immunopharmacol., 14(4):613-619 (1992).

Streeter, P. R. et al., "Activation of the G-CSF and Flt-3 receptors protects hematopoietic stem cells from lethal irradiation," Experimental Hematology, 31(11):1119-1125 (2003).

Symon, Z. et al., "Selective radioprotection of hepatocytes by systemic and portal vein infusions of amifostine in a rat liver tumor model," Int. J. Radiation Oncology Biol. Phys., 50(2):473-478 (2001).

Tallant, T. et al., "Flagellin acting via TLR5 is the major activator of key signaling pathways leading to NF-κB and proinflammatory gene program activation in intestinal epithelial cells," BMC Microbiology, 4(1):33 (2004).

Tsujimoto, H. et al., "Flagellin enhances NK cell proliferation and activation directly and through dendritic cell-NK cell interactions," Journal of Leukocyte Biology, 78(4):888-897 (2005).

Vasquez, R. J. et al., "Nanomolar concentrations of nocodazole alter microtubule dynamic instability in vivo and in vitro," Molecular Biology of the Cell, 8(6):973-985 (1997).

Waddick, K. G. et al., "In vitro and in vivo antileukemic activity of B43-pokeweed antiviral protein against radiation-resistant human B-cell precursor leukemia cells," Blood, 86(11):4228-4233 (1995).

Watson, A. J. et al., "Lessons from genetically engineered animal models. VII. Apoptosis in intestinal epithelium: lessons from transgenic and knockout mice," Am. J. Physiol. Gastrointest. Liver Physiol., 278(1):G1-G5 (2000).

Wheeler, C. M., "Preventative vaccines for cervial cancer," Salud Publica de Mexico, 39(4) (1997), 9 pages.

Whitnall, M. H. et al., "In vivo radioprotection by 5-androstenediol: stimulation of the innate immune system," Radiation Research, 156(3):283-293 (2001).

Wong, G. H. W., "Protective roles of cytokines against radiation: induction of mitochondrial MnSOD," Biochimica et Biophysica Acta, 1271:205-209 (1995).

\* cited by examiner

*Day 7 post-reperfusion*

*Immunohistochemistry staining of RB6, magnification, x200*

24 hours post I/R

Figure 7 , continued
7c
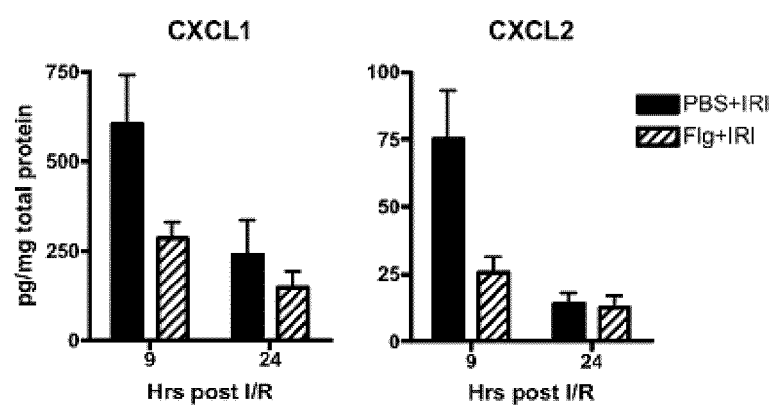

AA'
Nucleotide sequence (990 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGG*CACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTGATGTGAAAAGC
CTTGGCCTTGATGGGTCAATGTTAATTCCCCGGGAATTTCCGGTGGTGGTGGTGGAATT
CTAGACTCCATGGGTACATTAATCAATGAAGACGCTGCCGCAGCCAAGAAAAGTACCGCT
AACCCACTGGCTTCAATTGATTCTGCATTGTCAAAAGTGGACGCAGTTCGTTCTTCTCTG
GGGGCAATTCAAAACCGTTTTGATTCAGCCATTACCAACCTTGGCAATACGGTAACCAAT
CTGAACTCCGCGCGTAGCCGTATCGAAGATGCTGACTATGCAACGGAAGTTTCTAATATG
TCTAAAGCGCAGATTCTGCAGCAGGCTGGTACTTCCGTTCTGGCGCAGGCTAACCAGGTT
CCGCAAAACGTCCTCTCTTTACTGCGTTAG
Protein sequence (329 AA):
*MRGSHHHHHHGMASMTGGQQMGRDLYDDDDKDP*M<u>A</u>QVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLDGFNVNSPGISGGGGGILDSMGTLINEDAAAAKKSTANPLASIDSALSKVDAVRSSLGAIQNRFD
SAITNLGNTVTNLNSARSRIEDADYATEVSNMSKAQILQQAGTSVLAQANQVPQNVLSLLR AB'
Nucleotide sequence (825 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGG*CACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTGATGTGAAAAGC
CTTGGCCTTGATGGGTCAATGTTAATTCCCCGGGAATTTCCGGTGGTGGTGGTGGAATT
CTAGACTCCATGGGTACATTAATCAATGAAGACGCTGCCGCAGCCAAGAAAAGTACCGCT
AACCCACTGGCTTCAATTGATTCTGCATTGTCAAAAGTGGACGCAGTTCGTTCTTCTCTG
GGGGCAATTCAAAACCGTTTTGATTCAGCCATTACCAACCTTTAG
Protein sequence (274 AA):
*MRGSHHHHHHGMASMTGGQQMGRDLYDDDDKDP*M<u>A</u>QVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLDGFNVNSPGISGGGGGILDSMGTLINEDAAAAKKSTANPLASIDSALSKVDAVRSSLGAIQNRFD
SAITNL

Figure 13B

BA'
Nucleotide sequence (831 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCG*TTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTGATGTGAAAAGCCTTGGCCTTGATGGGTTCAATGTTAATTCCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTGGCAATACGGTAACCAATCTGAACTCCGCGTAGCCGTATCGAAGATGCTGACTAT
GCAACGGAAGTTTCTAATATGTCTAAAGCGCAGATTCTGCAGCAGGCTGGTACTTCCGTT
CTGGCGCAGGCTAACCAGGTTCCGCAAAACGTCCTCTCTTTACTGCGTTAG
Protein sequence (276 AA):
*MRGSHHHHHHGMASMTGGQQMGRDLYDDDDKDP*FTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLDGFNVNSPGISGGGGGILDSMG<u>TLINEDAAAAKKSTANPLASIDSALSKVD
AVRSSLGAIQNRFDSAITNLGNTVTNLNSARSRIEDADYATEVSNMSKAQILQQAGTSVLAQANQVP
QNVLSLLR</u>

BB'
Nucleotide sequence (666 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCG*TTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTGATGTGAAAAGCCTTGGCCTTGATGGGTTCAATGTTAATTCCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTTAG
Protein sequence (221 AA):
*MRGSHHHHHHGMASMTGGQQMGRDLYDDDDKDP*FTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLDGFNVNSPGISGGGGGILDSMG<u>TLINEDAAAAKKSTANPLASIDSALSKVD
AVRSSLGAIQNRFDSAITNL</u>

CA'
Nucleotide sequence (603 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCG*TTCACTTCTAATATCAAAGGC
CTGACTCAGGCTTCCCGTAACGCTAACGACGGCATTTCTATTGCGCAGACCACTGAAGGT

Figure 13 C

```
GCGCTGAATGAAATCAACAACAACCTGCAGCGTGTGCGTGAGTTGTCTGTTCAGGCCACT
TCCCCGGGAATTTCCGGTGGTGGTGGTGGAATTCTAGACTCCATGGGTACATTAATCAAT
GAAGACGCTGCCGCAGCCAAGAAAAGTACCGCTAACCCACTGGCTTCAATTGATTCTGCA
TTGTCAAAAGTGGACGCAGTTCGTTCTTCTCTGGGGGCAATTCAAAACCGTTTTGATTCA
GCCATTACCAACCTTGGCAATACGGTAACCAATCTGAACTCCGCGCGTAGCCGTATCGAA
GATGCTGACTATGCAACGGAAGTTTCTAATATGTCTAAAGCGCAGATTCTGCAGCAGGCT
GGTACTTCCGTTCTGGCGCAGGCTAACCAGGTTCCGCAAAACGTCCTCTCTTTACTGCGT
TAG
```
Protein sequence (200 AA):

*MRGSHHHHHHGMASMTGGQQMGRDLYDDDDKDP*FTSNIKGLTQASRNANDGISIAQTTEGALNEINN
NLQRVRELSVQATSPGISGGGGGILDSMGTLINEDAAAAKKSTANPLASIDSALSKVDAVRSSLGAI
QNRFDSAITNLGNTVTNLNSARSRIEDADYATEVSNMSKAQILQQAGTSVLAQANQVPQNVLSLLR

CB'
Nucleotide sequence (438 bp):

```
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
TCCCCGGGAATTTCCGGTGGTGGTGGTGGAATTCTAGACTCCATGGGTACATTAATCAAT
GAAGACGCTGCCGCAGCCAAGAAAAGTACCGCTAACCCACTGGCTTCAATTGATTCTGCA
TTGTCAAAAGTGGACGCAGTTCGTTCTTCTCTGGGGGCAATTCAAAACCGTTTTGATTCA
GCCATTACCAACCTTTAG
```
Protein sequence (145 AA):

*MRGSHHHHHHGMASMTGGQQMGRDLYDDDDKDP*FTSNIKGLTQASRNANDGISIAQTTEGALNEINN
NLQRVRELSVQATSPGISGGGGGILDSMGTLINEDAAAAKKSTANPLASIDSALSKVDAVRSSLGAI
QNRFDSAITNL

A
Nucleotide sequence (639 bp):

```
ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGTCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTGTCTCAGGACAACCAGATGAAAATCCAG
GTTGGTGCTAACGATGGTGAAACCATTACCATCGATCTGCAAAAAATTGATGTGAAAAGC
CTTGGCCTTGATGGGTTCAATGTTAATTCCCCGGGATGA
```
Protein sequence (212 AA), last three amino acids are derived from primer and pRSETb polylinker:

*MRGSHHHHHHGMASMTGGQQMGRDLYDDDDKDP*MAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLDGFNVNSPG

Figure 13 D

B
Nucleotide sequence (480 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGTTCACTTCTAATATCAAAGGT*
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTGTCTCAG
GACAACCAGATGAAAATCCAGGTTGGTGCTAACGATGGTGAAACCATTACCATCGATCTG
CAAAAAATTGATGTGAAAAGCCTTGGCCTTGATGGGTTCAATGTTAATTCCCCGGGATGA
Protein sequence (159 AA), last three amino acids are derived from primer and pRSETb polylinker:
*MRGSHHHHHHGMASMTGGQQMGRDLYDDDDKDP*FTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLDGFNVNSPG

C
Nucleotide sequence (252 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGTTCACTTCTAATATCAAAGGT*
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
TCCCCGGGATGA
Protein sequence (83 AA), last three amino acids are derived from primer and pRSETb polylinker:
*MRGSHHHHHHGMASMTGGQQMGRDLYDDDDKDP*FTSNIKGLTQASRNANDGISIAQTTEGALNEINN
NLQRVRELSVQATSPG

GST-A'
Nucleotide sequence (1038 bp), GST highlighted:

ATGTCCCCTATACTAGGTTATTGGAAAATTAAGGGCCTTGTGCAACCCACTCGACTTCTT
TTGGAATATCTTGAAGAAAAATATGAAGAGCATTTGTATGAGCGCGATGAAGGCGATAAA
GGCGAAACAAAAAGCTTGAATTGGGTTTGGAGTTTGCCAATCTTCCTTATTATATCGAT
GGTGATGTTAAATTAACACAGTCTATGGCCATCATACGTTATATAGCTGACAAGCACAAC
ATGCTGGGTGGTTGTCCAAAAGAGCGTGCAGAGATTTTGAATGCCTTGAAGGACCGGCTTTG
GATATTAGATACGGTGTTTCGAGAATGCCATATAGTAAAGACTTTGAAACTCTGAAAGTT
GATTTTCTTAGCAAGCTACCTGAAATGCTGAAAATGTTCGAAGATCGTTTATGTCATAAA
ACATATTTAAATGGTGATCATGTAACCCATCCTGACTTCATGTTGTATGACGCTCTCGAT
GTTGTTTTATACATGGACCCAATGTGCCTGGATGCCGTTCCCAAAATTAGTTTGTTTAAA
AAACGTATTGAAGCTATGCCACAAATTGATAAGTACTTGAAATCCAGCAAGTATATAGCA
TGGCCTTTGCAGGGCTGCCAAGCGACGTTTGGTGGTGGCGACCATCCTCCAAAATCGAT
CTGGTTCCGCGTGGA*TCCCCGGGAATTTCCGGTGGTGGTGGTGGAATTCTAGACTCCATG*
GGTACATTAATCAATGAAGACGCTGCCGCAGCCAAGAAAAGTACCGCTAACCCACTGGCT
TCAATTGATTCTGCATTGTCAAAAGTGGACGCAGTTCGTTCTTCTCTGGGGGCAATTCAA
AACCGTTTTGATTCAGCCATTACCAACCTTGGCAATACGGTAACCAATCTGAACTCCGCG
CGTAGCCGTATCGAAGATGCTGACTATGCAACGGAAGTTTCTAATATGTCTAAAGCGCAG
ATTCTGCAGCAGGCTGGTACTTCCGTTCTGGCGCAGGCTAACCAGGTTCCGCAAAACGTC
CTCTCTTTACTGCGTTAG
Protein sequence (345 AA):

Figure 13E

MSPILGYWKIKGLVQPTRLLLEYLEEKYEEHLYERDEGDKWRNKKFELGLEFPNLPYYIDGDVKLTQ
SMAIIRYIADKHNMLGGCPKERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKRIEAIPQIDKYLKSSKYIAW
PLQGWQATFGGGDHPPKSDLVPRGSPGISGGGGGILDSMGTLINEDAAAAKKSTANPLASIDSALSK
VDAVRSSLGAIQNRFDSAITNLGNTVTNLNSARSRIEDADYATEVSNMSKAQILQQAGTSVLAQANQ
VPQNVLSLLR

GST-B'
Nucleotide sequence (873 bp), GST highlighted:

ATGTCCCCTATACTAGGTTATTGGAAAATTAAGGGCCTTGTGCAACCCACTCGACTTCTT
TTGGAATATCTTGAAGAAAAATATGAAGAGCATTTGTATGAGCGGGATGAAGGTGATAAA
TGCCGAAACAAAAAGTTTCAATTGGGTTTGCACTTTGCCAATCTTCCTTATTATATTGAT
GGTGATGTTAAATAACACAGTCTATGGCCATCATAGGTTATATAGGTTGACAAGCACAAC
ATGTTGGGTGGTTGTCCAAAAGAGCGTGCAGAGATTTCAATGCTTGAAGGAGCGGTTTTG
GATATTAGATACGGTGTTTCGAGAATTGCATATAGTAAAGACTTTGAAACTCTCAAAGTT
GATTTTCTTAGCAAGCTACCTGAAATGCTGAAAATGTTCGAAGATCGTTTATGTCATAAA
ACATATTTAAATGGTGATCATGTAACCCATCCTGACTTCATGTTGTATGACCCTCTTGAT
GTTGTTTTATACATGGACCCAATGTGCCTGGATGCGTTCCCAAAATTAGTTTGTTTTAAA
AAACGTATTGAAGCTATCCCACAAATTGATAAGTACTTGAAATCCAGCAAGTATATAGCA
TGGCCTTTGCAGGGCTGGCAAGCCACGTTTGGTGGTGGCGACCATCCTCCAAAAATCGGAT
CTGGTTCCGCCGTGGA**TCCCCGGGAATTTCCGGTGGTGGTGGTGGAATTCTAGACTCCATG
GGT**ACATTAATCAATGAAGACGCTGCCGCAGCCAAGAAAAGTACCGCTAACCCACTGGCT
TCAATTGATTCTGCATTGTCAAAAGTGGACGCAGTTCGTTCTTCTCTGGGGGCAATTCAA
AACCGTTTTGATTCAGCCATTACCAACCTTTAG

Protein sequence (290 AA):

MSPILGYWKIKGLVQPTRLLLEYLEEKYEEHLYERDEGDKWRNKKFELGLEFPNLPYYIDGDVKLTQ
SMAIIRYIADKHNMLGGCPKERAEISMLEGAVLDIRYGVSRIAYSKDFETLKVDFLSKLPEMLKMFE
DRLCHKTYLNGDHVTHPDFMLYDALDVVLYMDPMCLDAFPKLVCFKKRIEAIPQIDKYLKSSKYIAW
PLQGWQATFGGGDHPPKSDLVPRGSPGISGGGGGILDSMGTLINEDAAAAKKSTANPLASIDSALSK
VDAVRSSLGAIQNRFDSAITNL

AA'n1-170
Nucleotide sequence (972 bp):

*ATGCGGGGTTCTCATCATCATCATCATCATGGTATGGCTAGCATGACTGGTGGACAGCAA
ATGGGTCGGGATCTGTACGACGATGACGATAAGGATCCGATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTGATGTGAAAAGC
CTTGGCCTTATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGGCAATTCAAAACCGT
TTTGATTCAGCCATTACCAACCTTGGCAATACGGTAACCAATCTGAACTCCGCGCGTAGC
CGTATCGAAGATGCTGACTATGCAACGGAAGTTTCTAATATGTCTAAAGCGCAGATTCTG
CAGCAGGCTGGTACTTCCGTTCTGGCGCAGGCTAACCAGGTTCCGCAAAACGTCCTCTCT*

Figure 13 F

TTACTGCGTTAG
Protein sequence (323 AA):
*MRGSHHHHHHGMASMTGGQQMGRDLYDDDDKDP*MAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIDVKSL
GLIPGISGGGGGILDSMGTLINEDAAAAKKSTANPLASIDSALSKVDAVRSSLGAIQNRFDSAITNL
GNTVTNLNSARSRIEDADYATEVSNMSKAQILQQAGTSVLAQANQVPQNVLSLLR AA'n1-163
Nucleotide sequence (951 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATG*GCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTATCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTGGCAATACGGTAACCAATCTGAACTCCGCGCGTAGCCGTATCGAAGATGCTGACTAT
GCAACGGAAGTTTCTAATATGTCTAAAGCGCAGATTCTGCAGCAGGCTGGTACTTCCGTT
CTGGCGCAGGCTAACCAGGTTCCGCAAAACGTCCTCTCTTTACTGCGTTAG
Protein sequence (316 AA):
*MRGSHHHHHHGMASMTGGQQMGRDLYDDDDKDP*MAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIIPGIS
GGGGGILDSMGTLINEDAAAAKKSTANPLASIDSALSKVDAVRSSLGAIQNRFDSAITNLGNTVTNL
NSARSRIEDADYATEVSNMSKAQILQQAGTSVLAQANQVPQNVLSLLR AA'n54-170
Nucleotide sequence (813 bp):
*ATGCGGGGTTCTCATCATCATCATCATCATGGTATGGCTAGCATGACTGGTGGACAGCAA*
*ATGGGTCGGGATCTGTACGACGATGACGATAAGGATCC*GTTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTGATGTGAAAAGCCTTGGCCTTATCCCGGGAATTTCCGGTGGTGGTGGTGGA
ATTCTAGACTCCATGGGTACATTAATCAATGAAGACGCTGCCGCAGCCAAGAAAAGTACC
GCTAACCCACTGGCTTCAATTGATTCTGCATTGTCAAAAGTGGACGCAGTTCGTTCTTCT
CTGGGGGCAATTCAAAACCGTTTTGATTCAGCCATTACCAACCTTGGCAATACGGTAACC
AATCTGAACTCCGCGCGTAGCCGTATCGAAGATGCTGACTATGCAACGGAAGTTTCTAAT
ATGTCTAAAGCGCAGATTCTGCAGCAGGCTGGTACTTCCGTTCTGGCGCAGGCTAACCAG
GTTCCGCAAAACGTCCTCTCTTTACTGCGTTAG

Figure 13 G

Protein sequence (270 AA):
*MRGSHHHHHHGMASMTGGQQMGRDLYDDDDKDP*FTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIDVKSLGLIPGISGGGGGILDSMGTLINEDAAAAKKSTANPLASIDSALSKVDAVRSSL
GAIQNRFDSAITNLGNTVTNLNSARSRIEDADYATEVSNMSKAQILQQAGTSVLAQANQVPQNVLSL
LR AA'n54-163
Nucleotide sequence (792 bp):
*ATGCGGGGTTCTCATCATCATCATCATCATGGTATGGCTAGCATGACTGGTGGACAGCAA
ATGGGTCGGGATCTGTACGACGATGACGATAAGGATCCG*TTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGACTCAATTTAACGGTGTTAAAGTCCTCTCTCAG
GACAACCAGATGAAAATCCAGGTTGGTGCTAACGATGGTGAAACCATTACCATCGATCTG
CAAAAAATTATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGGCAATTCAAAACCGT
TTTGATTCAGCCATTACCAACCTTGGCAATACGGTAACCAATCTGAACTCCGCGCGTAGC
CGTATCGAAGATGCTGACTATGCAACGGAAGTTTCTAATATGTCTAAAGCGCAGATTCTG
CAGCAGGCTGGTACTTCCGTTCTGGCGCAGGCTAACCAGGTTCCGCAAAACGTCCTCTCT
TTACTGCGTTAG
Protein sequence (263 AA):
*MRGSHHHHHHGMASMTGGQQMGRDLYDDDDKDP*FTSNIKGLTQASRNANDGISIAQTTEGALNEINN
NLQRVRELSVQATNGTNSDSDLKSIQDEIQQRLEEIDRVSNQTQFNGVKVLSQDNQMKIQVGANDGE
TITIDLQKIIPGISGGGGGILDSMGTLINEDAAAAKKSTANPLASIDSALSKVDAVRSSLGAIQNRF
DSAITNLGNTVTNLNSARSRIEDADYATEVSNMSKAQILQQAGTSVLAQANQVPQNVLSLLR AB'n1-170 (or AA'n1-170c402-450)
Nucleotide sequence (807 bp):
*ATGCGGGGTTCTCATCATCATCATCATCATGGTATGGCTAGCATGACTGGTGGACAGCAA
ATGGGTCGGGATCTGTACGACGATGACGATAAGGATCCG*ATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTGATGTGAAAAGC
CTTGGCCTTATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGGCAATTCAAAACCGT
TTTGATTCAGCCATTACCAACCTTTAG
Protein sequence (268 AA):
*MRGSHHHHHHGMASMTGGQQMGRDLYDDDDKDP*MAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN

Figure 13H

GTNSDSDLKSIQDEIQQRLEEIDRVSNQTQFNGVKVLSQDNQMKIQVGANDGETITIDLQKIDVKSL
GLIPGISGGGGGILDSMGTLINEDAAAAKKSTANPLASIDSALSKVDAVRSSLGAIQNRFDSAITNL

AB'n1-163 (or AA'n1-163c402-450)
Nucleotide sequence (786 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGG*CACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGACTCAATTTAACGGTGTTAAAGTCCTCTCTCAGGACAACCAGATGAAAATCCAG
GTTGGTGCTAACGATGGTGAAACCATTACCATCGATCTGCAAAAAATTATCCCGGGAATT
TCCGGTGGTGGTGGTGGAATTCTAGACTCCATGGGTACATTAATCAATGAAGACGCTGCC
GCAGCCAAGAAAAGTACCGCTAACCCACTGGCTTCAATTGATTCTGCATTGTCAAAAGTG
GACGCAGTTCGTTCTTCTCTGGGGGCAATTCAAAACCGTTTTGATTCAGCCATTACCAAC
CTTTAG Protein sequence (261 AA):
*MRGSHHHHHHGMASMTGGQQMGRDLYDDDDKDPM*AQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQTQFNGVKVLSQDNQMKIQVGANDGETITIDLQKIIPGIS
GGGGGILDSMGTLINEDAAAAKKSTANPLASIDSALSKVDAVRSSLGAIQNRFDSAITNL AA'n1-129
Nucleotide sequence (849 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGG*CACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGATCCCGGGAATTTCCGGTGGTGGTGGTGGAATTCTAGACTCCATGGGTACATTA
ATCAATGAAGACGCTGCCGCAGCCAAGAAAAGTACCGCCACTGGCTTCAATTGAT
TCTGCATTGTCAAAAGTGGACGCAGTTCGTTCTTCTCTGGGGGCAATTCAAAACCGTTTT
GATTCAGCCATTACCAACCTTGGCAATACGGTAACCAATCTGAACTCCGCGCGTAGCCGT
ATCGAAGATGCTGACTATGCAACGGAAGTTTCTAATATGTCTAAAGCGCAGATTCTGCAG
CAGGCTGGTACTTCCGTTCTGGCGCAGGCTAACCAGGTTCCGCAAAACGTCCTCTCTTTA
CTGCGTTAG Protein sequence (282 AA):
*MRGSHHHHHHGMASMTGGQQMGRDLYDDDDKDPM*AQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQIPGISGGGGGILDSMGTLINEDAAAAKKSTANPLASIDS
ALSKVDAVRSSLGAIQNRFDSAITNLGNTVTNLNSARSRIEDADYATEVSNMSKAQILQQAGTSVLA
QANQVPQNVLSLLR

Figure 13 I

AA'n54-129
Nucleotide sequence (690 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCG*TTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT
AACGGGACTAACTCTGATTCCGATCTGAAATCTATCCAGGATGAAATTCAGCAACGTCTG
GAAGAAATCGATCGCGTTTCTAATCAGATCCCGGGAATTTCCGGTGGTGGTGGTGGAATT
CTAGACTCCATGGGTACATTAATCAATGAAGACGCTGCCGCAGCCAAGAAAAGTACCGCT
AACCCACTGGCTTCAATTGATTCTGCATTGTCAAAAGTGGACGCAGTTCGTTCTTCTCTG
GGGGCAATTCAAAACCGTTTTGATTCAGCCATTACCAACCTTGGCAATACGGTAACCAAT
CTGAACTCCGCGCGTAGCCGTATCGAAGATGCTGACTATGCAACGGAAGTTTCTAATATG
TCTAAAGCGCAGATTCTGCAGCAGGCTGGTACTTCCGTTCTGGCGCAGGCTAACCAGGTT
CCGCAAAACGTCCTCTCTTTACTGCGTTAG
Protein sequence (229 AA):
*MRGSHHHHHHGMASMTGGQQMGRDLYDDDDKDP*F TSNIKGLTQASRNANDGISIAQTTEGALNEINN
NLQRVRELSVQATNGTNSDSDLKSIQDEIQQRLEEIDRVSNQIPGISGGGGGILDSMGTLINEDAAA
AKKSTANPLASIDSALSKVDAVRSSLGAIQNRFDSAITNLGNTVTNLNSARSRIEDADYATEVSNMS
KAQILQQAGTSVLAQANQVPQNVLSLLR AB'n1-129
Nucleotide sequence (684 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCG*ATGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTAACGGGACTAACTCTGATTCC
GATCTGAAATCTATCCAGGATGAAATTCAGCAACGTCTGGAAGAAATCGATCGCGTTTCT
AATCAGATCCCGGGAATTTCCGGTGGTGGTGGTGGAATTCTAGACTCCATGGGTACATTA
ATCAATGAAGACGCTGCCGCAGCCAAGAAAAGTACCGCTAACCCACTGGCTTCAATTGAT
TCTGCATTGTCAAAAGTGGACGCAGTTCGTTCTTCTCTGGGGGCAATTCAAAACCGTTTT
GATTCAGCCATTACCAACCTTTAG
Protein sequence (227 AA):
*MRGSHHHHHHGMASMTGGQQMGRDLYDDDDKDP*MAQVINTNSLSLLTQNNLNKSQSSLSSAIERLSS
GLRINSAKDDAAGQAIANRFTSNIKGLTQASRNANDGISIAQTTEGALNEINNNLQRVRELSVQATN
GTNSDSDLKSIQDEIQQRLEEIDRVSNQIPGISGGGGGILDSMGTLINEDAAAAKKSTANPLASIDS
ALSKVDAVRSSLGAIQNRFDSAITNL AB'n54-129
Nucleotide sequence (525 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCG*TTCACTTCTAATATCAAAGGC
CTGACTCAGGCTTCCCGTAACGCTAACGACGGCATTTCTATTGCGCAGACCACTGAAGGT
GCGCTGAATGAAATCAACAACAACCTGCAGCGTGTGCGTGAGTTGTCTGTTCAGGCCACT

Figure 13 J

AACGGGACTAACTCTGATTCCGATCTGAAATCTATCCAGGATGAAATTCAGCAACGTCTG
GAAGAAATCGATCGCGTTTCTAATCAGATCCCGGGAATTTCCGGTGGTGGTGGTGGAATT
CTAGACTCCATGGGTACATTAATCAATGAAGACGCTGCCGCAGCCAAGAAAAGTACCGCT
AACCCACTGGCTTCAATTGATTCTGCATTGTCAAAAGTGGACGCAGTTCGTTCTTCTCTG
GGGGCAATTCAAAACCGTTTTGATTCAGCCATTACCAACCTTTAG
Protein sequence (174 AA):
*MRGSHHHHHHGMASMTGGQQMGRDLYDDDDKDP*FTSNIKGLTQASRNANDGISIAQTTEGALNEINN
NLQRVRELSVQATNGTNSDSDLKSIQDEIQQRLEEIDRVSNQIPGISGGGGGILDSMGTLINEDAAA
AKKSTANPLASIDSALSKVDAVRSSLGAIQNRFDSAITNL AA'n1-100
Nucleotide sequence (762 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGG*CACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTATCCCGGGAATTTCCGGTGGT
GGTGGTGGAATTCTAGACTCCATGGGTACATTAATCAATGAAGACGCTGCCGCAGCCAAG
AAAAGTACCGCTAACCCACTGGCTTCAATTGATTCTGCATTGTCAAAAGTGGACGCAGTT
CGTTCTTCTCTGGGGGCAATTCAAAACCGTTTTGATTCAGCCATTACCAACCTTGGCAAT
ACGGTAACCAATCTGAACTCCGCGCGTAGCCGTATCGAAGATGCTGACTATGCAACGGAA
GTTTCTAATATGTCTAAAGCGCAGATTCTGCAGCAGGCTGGTACTTCCGTTCTGGCGCAG
GCTAACCAGGTTCCGCAAAACGTCCTCTCTTTACTGCGTTAG
Protein sequence (253 AA):
*MRGSHHHHHHGMASMTGGQQMGRDLYDDDDKDP*MAQVINTNSLSLLTQNNLNKSQSSLSSAIERLSS
GLRINSAKDDAAGQAIANRFTSNIKGLTQASRNANDGISIAQTTEGALNEINNNLQRVRELSVQATI
PGISGGGGGILDSMGTLINEDAAAAKKSTANPLASIDSALSKVDAVRSSLGAIQNRFDSAITNLGNT
VTNLNSARSRIEDADYATEVSNMSKAQILQQAGTSVLAQANQVPQNVLSLLR AB'n1-100
Nucleotide sequence (597 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGATGG*CACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACGGCATTTCTATTGCGCAGACCACTGAAGGTGCGCTGAATGAAATCAACAAC
AACCTGCAGCGTGTGCGTGAGTTGTCTGTTCAGGCCACTATCCCGGGAATTTCCGGTGGT
GGTGGTGGAATTCTAGACTCCATGGGTACATTAATCAATGAAGACGCTGCCGCAGCCAAG
AAAAGTACCGCTAACCCACTGGCTTCAATTGATTCTGCATTGTCAAAAGTGGACGCAGTT
CGTTCTTCTCTGGGGGCAATTCAAAACCGTTTTGATTCAGCCATTACCAACCTTTAG
Protein sequence (198 AA):
*MRGSHHHHHHGMASMTGGQQMGRDLYDDDDKDP*MAQVINTNSLSLLTQNNLNKSQSSLSSAIERLSS
GLRINSAKDDAAGQAIANRFTSNIKGLTQASRNANDGISIAQTTEGALNEINNNLQRVRELSVQATI
PGISGGGGGILDSMGTLINEDAAAAKKSTANPLASIDSALSKVDAVRSSLGAIQNRFDSAITNL

Figure 13 K

AA'n1-70
Nucleotide sequence (672 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGA*TGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGGCAATTCAAAACCGT
TTTGATTCAGCCATTACCAACCTTGGCAATACGGTAACCAATCTGAACTCCGCGCGTAGC
CGTATCGAAGATGCTGACTATGCAACGGAAGTTTCTAATATGTCTAAAGCGCAGATTCTG
CAGCAGGCTGGTACTTCCGTTCTGGCGCAGGCTAACCAGGTTCCGCAAAACGTCCTCTCT
TTACTGCGTTAG
Protein sequence (223 AA):
*MRGSHHHHHHGMASMTGGQQMGRDLYDDDDKDPM*AQVINTNSLSLLTQNNLNKSQSSLSSAIERLSS
GLRINSAKDDAAGQAIANRFTSNIKGLTQASRNANDIPGISGGGGGILDSMGTLINEDAAAAKKSTA
NPLASIDSALSKVDAVRSSLGAIQNRFDSAITNLGNTVTNLNSARSRIEDADYATEVSNMSKAQILQ
QAGTSVLAQANQVPQNVLSLLR AB'n1-70
Nucleotide sequence (507 bp):
*ATGCGGGGTTCTCATCATCATCATCATCATGGTATGGCTAGCATGACTGGTGGACAGCAA*
*ATGGGTCGGGATCTGTACGACGATGACGATAAGGATCCGA*TGGCACAAGTCATTAATACA
AACAGCCTGTCGCTGTTGACCCAGAATAACCTGAACAAATCTCAGTCCTCACTGAGTTCC
GCTATTGAGCGTCTGTCCTCTGGTCTGCGTATCAACAGCGCGAAAGACGATGCGGCAGGC
CAGGCGATTGCTAACCGCTTCACTTCTAATATCAAAGGCCTGACTCAGGCTTCCCGTAAC
GCTAACGACATCCCGGGAATTTCCGGTGGTGGTGGTGGAATTCTAGACTCCATGGGTACA
TTAATCAATGAAGACGCTGCCGCAGCCAAGAAAAGTACCGCTAACCCACTGGCTTCAATT
GATTCTGCATTGTCAAAAGTGGACGCAGTTCGTTCTTCTCTGGGGGCAATTCAAAACCGT
TTTGATTCAGCCATTACCAACCTTTAG
Protein sequence (168 AA):
*MRGSHHHHHHGMASMTGGQQMGRDLYDDDDKDPM*AQVINTNSLSLLTQNNLNKSQSSLSSAIERLSS
GLRINSAKDDAAGQAIANRFTSNIKGLTQASRNANDIPGISGGGGGILDSMGTLINEDAAAAKKSTA
NPLASIDSALSKVDAVRSSLGAIQNRFDSAITNL Hematoxylin/eosin stain of section from hind limb muscle on day 14 after reperfusion following 3 hours of warm ischemia A. Mouse given 0.5 ug CBLB502 i.m. within 15 min of reperfusion.
B. Mouse given PBS/1%BSA i.m. within 15 min of reperfusion.

C CBLB502 decreases tissue edema

D CBLB502 attenuates vascular leak i = ischemia reperfusion injured limb
c = contralateral limb

Figure 15A

```
Q53970   1 MAQVINTNSLSLLTQNNLNKSQSSLSSAIERLSSGLRINSAKDDAAGQAIANRFTSNIKGLTQASRNAND
P72151   1 MALTVNTNIASLNTQRNLNASSNDLNTSLQRLTTGYRINSAKDDAAGLQISNRLSNQISGLNVATRNAND
Q5X5M6   1 MAQVINTNVASLTAQRNLGVSGNMMQTSIQRLSSGLRINSAKDDAAGLAISQRMTAQIRGMNQAVRNAND
Q6VMV6   1 MAQVINTNSLSLLTQNNLNKSQSSLSSAIERLSSGLRINSAKDDAAGQAIANRFTANIKGLTQASRNAND
P13713   1 MAQVINTNSLSLMAQNNLNKSQSSLGTAIERLSSGLRINSAKDDAAGQAISNRFTANIKGLTQASRNAND
Q93RK8   1 --MRINHNIAALNTSRQLNAGSNSAAKNMEKLSSGLRINRAGDDAAGLAISEKMRSQIRGLDMASKNAQD
Q02551   1 --MKVNTNIISLKTQEYLRKNNEGMTQAQFRLASGKRINSSLDDAAGLAVVTRMNVKSTGLDAASKNSSM
Q09012   1 MAQVINTNSLSLLTQNNLNKSQSSLSSAIERLSSGLRINSAKDDAAGQAIANRFTANIKGLTQASRNAND
Q8GNT8   1 MAQVINTNSLSLMAQNNLNKSQSALGTAIERLSSGLRINSAKDDAAGQAISNRFTANINGLTQASRNAND
Q9FAE7   1 MASTINTNVSSLTAQRNLSLSQSSLNTSIQRLSSGLRINSAKDDAAGLAISERFTSQIRGLNQAVRNAND
Q8ZF76   1 MA-VINTNSLSLLTQNNLNKSQSSLSSAIERLSSGLRINSAKDDAAGQAIANRFTSNIKGLTQAARNAND
Q7N5J4   1 MAQVINTNSLSLLTQNNLNRSQGTLGSAIERLSSGLRINSAKDDAAGQAIANRFTANVRGLTQAARNAND
O33578   1 -MTTINTNIGAIAAQANMTKVNDQFNTAMTRLSTGLRINAAKDDAAGMAIGKKMTAQVMGLNQAIRNAQD
Q56826   1 MASVINTNDSALLAQNNLTKSKGILGSAIERLSSGLRINSAKDDAAGQAIANRFTANVKGLTQAARNAND
P42273   1 MAQVINTNYLSLVTQNNLNRSQSALGNAIERLSSGMRINSAKDDAAGQAIANRFTSNINGLTQAARNAND
O31059   1 --MVVQHNMQAANASRMLGITTGDQSKSTEKLSSGFKINRAADDAAGLSISEKMRKQIRGLDQASTNASD
Q7VZC2   1 MAAVINTNYLSLVAQNNLNKSQSALGSAIERLSSGLRINSAKDDAAGQAIANRFTANVKGLTQAARNAND
Q9F4A4   1 --MIINHNMNALNAHRNMMGNIATAGKSMEKLSSGLRINRAGDDAAGLAISEKMRGQIRGLDQASRNAQD
Q8P9C4   1 MAQVINTNVMSLNAQRNLNTNSSSMALSIQQLSSGKRITSASVDAAGLAISERFTTQIRGLDVASRNAND
Q82UA3   1 MPQVINTNIASLNAQRNLNVSQNSLSTALQRLSSGLRINSAKDDAAGLAISERMTSQIRGMNQAARNAND
Q84IC5   1 -GFRINTNGASLNAQVNAGLNSRNLDSSLARLSSGLRINSAADDASGLAIADSLKTQANSLGQAINNAND
              :: *   :  :              :*::* :*. :  **:*   :    .: * *:.

Q53970  71 GISIAQTTEGALNEINNNLQRVRELSVQATNGTNSDSDLKSIQDEIQQRLEEIDRVSNQTQFNGVKVLSQ
P72151  71 GISLAQTAEGALQQSTNILQRIRDLALQSANCSNSDADRAALQKEVAAQQAELTRISDTTTFGGRKLLDG
Q5X5M6  71 GISLAQVAEGAMQETTNILQRMRELSVQAANSTNNSSDRASIQSEISQLKSELERIAQNTEFNGQRILDG
Q6VMV6  71 GISVAQTTEGALNEINNNLQRVRELTVQATNGTNSDSDLSSIQAEITQRLEEIDRVSEQTQFNGVKVLAE
P13713  71 GISLAQTTEGALNEVNDNLQNIRRLTVQAQNGSNSTSDLKSIQDEITQRLSEINRISEQTDFNGVKVLSS
Q93RK8  69 GISLIQTSEGALNETHSILQRMSELATQAANDTNTDSDRSELQKEMDQLASEVTRISTDTEFNTKKLLDG
Q02551  71 GIDLLQTADSALSSMSSILQRMRQLAVQSSNGSFSDEDRKQYTAEFGSLIKELDHVADTTNYNNIKLLDQ
Q09012  69 GISVAQTTEGALSEINNNLQRIRELSVQATNGTNSDSDLNSIQDEITQRLSEIDRVSNQTQFNGVKVLAS
Q8GNT8  71 GISLAQTTEGALNEVNDNLQRIRRLTVQAQNGSNSSSDLQSIQDEITQRLSEIDRISQQTDFNGVKVLSK
Q9FAE7  71 GISLAQTAEGALKSTGDILQRVRELAVQSANATNSSGDRAIQAEVGQLLSEMDRIAGNTEFNGQKLLDG
Q8ZF76  70 CISIAQTTEGSLNEINNNLQRVRELTVQAQNGSNSSSDLDSTQDEISLRLAEIDRVSDQTQFNGKKVLAE
Q7N5J4  71 GISIAQTTEGALNEINTNLQRIRELTVQSQNGSNSESDIKSIQEEVTQRLKEIDRISEQTQFNGVRVLRE
O33578  70 GKNLVDTTEGAHVEVSSMLQRLRELAVQSSNDTNTAADRGSLAAEGKQLIAEINRVAESTTTNGMKVLDG
Q56826  71 GISIAQTTEGALNEINNNLQRIRELTVQSENGSNSKSDLDSIQKEVTQRLEEIDRISTQTQFNGIKVLNG
P42273  71 GISVSQTTEGALNEINNNLQRIRELTVQAKNGTNSNSDINSIQNEVNQRLDEINRVSEQTQFNGVKVLSG
O31059  69 GISAVQTAEGALTEVHSMLQRMNELAVQAANGTNSESDRSSIQDEINQLTTEIDRVAETTKFNETYLLKG
Q7VZC2  71 GISIAQTTEGALNEINNNLQRIRELTVQASMGTNSASDIDSIQQEVNQRLEEINRIAEQTDFNGIKVLKS
Q9F4A4  69 GISLIQTAEGALAETHSILQRMRELSVQSANDTNVAVDRTAIQEEINSLTEEINRISGDTEFNTQKLLDG
Q8P9C4  71 GISLAQTAEGAMVEIGNNLQRIRELSVQSANATNSATDREALNSEVKQLTSEIDRVANQTSFNGTKLLNG
Q82UA3  71 GISLAQTAEGALVEIGNNLQRIRELAVQSANATNSEDDREALQKEVTQLIDEIQRVCEQTSFNGTKLLDG
Q84IC5  70 ANSMLQIADKAMDEQLKILDTIKVKATQAAQDGQTAKTRAMIQGEINKLMEELDNIANTTTYNGKQLLSG
             .. :::  :   .    *: :    : *: :   :     *      *: ..  * :.   :*
```

Figure 15B

```
Q53970  141 DNQ-MK--IQVGANDG---------------ETITIDLQ----------KID-VKSLG----LDGFN
P72151  141 SFGTTS--FQVGSNAY---------------ETIDISLQNASASAIGSYQVG-SNGAGTVASVAGTA
Q5X5M6  141 SFSGAS--FQVGANSN---------------QTINFSIG----------SIK-ASSIGGIATATGTE
Q6VMV6  141 NNE-MK--IQVGANDG---------------ETITINLA----------KID-AKTLG----LDGFN
P13713  141 DQK-LT--IQVGANDG---------------ETTDIDLK----------KID-AKQLG----MDTF-
Q93RK8  139 TAQNLT--FQIGANEG---------------QTMSLSIN----------KMD-SE---------SLK
Q02551  139 TATGAATQVSIQASDKAN-------------DLINIDLFNAKGLSAGTITLGSGSTVAGYSALSVAD
Q09012  141 DQT-MK--ICVGANDG---------------ETIEIALD----------KID-AKTLG----LDNFS
Q8GNT8  141 DQK-LT--IQVGANDG---------------ETIDIDLK----------NIN-AQSLG----LDKFN
Q9FAE7  141 SFGSAT--FQVGANAN---------------QTITATTGNFRTNNY-GAQLT-ASASG--AATSGAS
Q8ZF76  140 NTT-MS--IQVGANDG---------------ETIDINLQ----------KID-SKSLG----LGSYS
Q7N5J4  141 DSK-MT--IQVGANDN---------------EVIDIDLK----------KID-KEALN----LGKFT
O33578  140 SFTGKQ--LQIGADSG---------------QTMAINVDSAAATDIGAHKISSASTVVADAALTDTT
Q56826  141 DVTEMK--IQVGANDN---------------ETIGIKLG----------KTN-SEKLN----LKEFS
P42273  141 EKSKMT--IQVGTNDN---------------EVIEFNLD----------KID-NDTLG----VASDK
O31059  139 GNGDRT--VRVYAHDAGLVGSLSQNTTKATFQMRKLEIGDSYTIGGTTYKIG-AETVK--EAMTALK
Q7VZC2  141 NATDMTLSIQVGAKDN---------------ETIDIKID----------RNS-NWNLY----DAVGT
Q9F4A4  139 GFKG-E--FQIGANSN---------------QTVKLDIG----------NMS-AA-----------SLG
Q8P9C4  141 DFSGAL--FQVGADAG---------------QTIGINS---------IVDAN-VDSLG--KANFAAS
Q82UA3  141 SFASQI--FQVGANEG---------------ETIDFTD-----------------------------
Q84IC5  140 SFSNAQ--FQIGDKAN---------------QTVNATIG----------STN-SAKVGQTRFETGAV
                    :                                :
```

Figure 15C

METHODS FOR TREATING TOURNIQUET-INDUCED INJURIES

CROSS-REFERENCE TO RELATED APPLICATIONS

This application is a continuation of U.S. patent application Ser. No. 13/530,580, filed Jun. 22, 2012, now U.S. Pat. No. 8,618,059, which is a continuation of U.S. patent application Ser. No. 13/056,973, filed Jan. 31, 2011, now U.S. Pat. No. 8,324,163, which is a 371 national application of International Patent Application No. PCT/US2009/052493, which claims the benefit of U.S. Provisional Application No. 61/085,766, filed on Aug. 1, 2008, the contents of all of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: CLEV_008_03US_SeqList_ST25.txt, date recorded: Mar. 24, 2014, file size 135 kilobytes).

FIELD OF THE INVENTION

This invention relates to the use of flagellin related polypeptides to treat tissues from the effects of reperfusion.

BACKGROUND OF THE INVENTION

Tissues deprived of blood and oxygen undergo ischemic necrosis or infarction with possible irreversible organ damage. Once the flow of blood and oxygen is restored to the organ or tissue (reperfusion), the organ does not immediately return to the normal preischemic state. Reperfusion of coronary flow is necessary to resuscitate the ischemic or hypoxic tissue or organ. Timely reperfusion facilitates salvage of cells and decreases morbidity and mortality. Reperfusion of an ischemic area may result in a paradoxical dysfunction including marked endothelial cell dysfunction, which results in vasoconstriction, platelet and leukocyte activation, increased oxidant production, and increased fluid and protein extravasation.

Over the past two decades has witnessed several pharmacological interventions designed to limit reperfusion injury. Unfortunately, the success of some agents has been limited to experimental model of ischemia and reperfusion. The lack of consistent clinical benefit may be related to a variety of factors, including poor clinical trial design, inadequate pharmacokinetic/pharmacodynamic studies and the complexity of the human in vivo model.

There is a need in the art to distinguish therapeutic strategies for ischemia vs. reperfusion, and it is possible that a combination of agents is required to elicit the maximum clinical benefit.

SUMMARY OF THE INVENTION

Provided herein is a method of treating a tissue of a mammal from the effects of reperfusion, which may comprise administering to a mammal in need thereof a composition comprising flagellin. The composition may be administered in combination with an antioxidant, which may be selected from the group consisting of amifostine and vitamin E.

The reperfusion may be caused by an injury, which may be ischemia or hypoxia. The ischemia may be selected from the group consisting of tachycardia, infarction, hypotension, embolism, thromboemoblism (blood clot), sickle cell disease, localized pressure to extremities to the body, and tumors. The hypoxia may be selected from the group consisting of hypoxemic hypoxia (carbon monoxide poisoning; sleep apnea, chronic obstructive pulmonary disease, respiratory arrest; shunts), anemic hypoxia (O2 content low), hypoxemic hypoxia, and histotoxic hypoxia. The localized pressure may be due to a tourniquet.

The composition may be administered prior to, together with, or after the influx of oxygen. The tissue may be selected from the group consisting of GI tract, lung, kidney, liver, cardiovascular system, blood vessel endothelium, central nervous system, peripheral nervous system, muscle, bone, and hair follicle.

BRIEF DESCRIPTION OF THE DRAWINGS

FIG. 5a is kidney tissue cells immunohistochemically stained for levels of neutrophil infiltration 9 hours and 24 hours after reperfusion in ischemic and non-ischemic treated kidneys cells from mice pretreated with PBS or flagellin at 0.5 µg/body. FIG. 5b is the number of neutrophils, macrophages, $CD4^+$ T cells, and $CD8^+$ T cells infiltrating into kidney tissue cells isolated from mice pretreated with PBS or flagellin a concentration of 0.5 µg/body. FIG. 5c shows the effects of flagellin on myeloperoxidase levels, as a measure of the activation of neutrophils, during reperfusion of ischemic kidneys as compared to controls.

FIG. 7a shows the effects of administering flagellin 30 minutes before or within 30 minutes after declamping on the viability of mice subjected to ischemic injury. FIG. 7b shows the effects of administering flagellin 30 minutes before declamping or within 30 minutes following declamping on levels of serum creatinine after reperfusion of the ischemic kidneys. FIG. 7c shows the effects of flagellin on CXCL1 and CXCL2 levels at 9 and 24 hours after reperfusion.

FIGS. 13A-K show the nucleotide and amino acid sequence for the following flagellin variants: AA' (SEQ ID NO: 7-8), AB' (SEQ ID NO: 9-10), BA' (SEQ ID NO: 11-12), BB' (SEQ ID NO: 13-14), CA' (SEQ ID NO: 15-16), CB' (SEQ ID NO: 17-18), A (SEQ ID NO: 19-20), B (SEQ ID NO: 21-22), C (SEQ ID NO: 23-24), GST-A' (SEQ ID NO: 25-26), GST-B' (SEQ ID NO: 27-28), AA'n1-170 (SEQ ID NO: 29-30), AA'n1-163 (SEQ ID NO: 33-34), AA'n54-170 (SEQ ID NO: 31-32), AA'n54-163 (SEQ ID NO: 335-36), AB'n1-170 (SEQ ID NO: 37-38), AB'n1-163 (SEQ ID NO: 39-40), AA'n1-129 (SEQ ID NO: 41-42), AA'n54-129 (SEQ ID NO: 43-44), AB'n1-129 (SEQ ID NO: 45-46), AB'n54-129 (SEQ ID NO: 47-48), AA'n1-100 (SEQ ID NO: 49-50), AB'n1-100 (SEQ ID NO: 51-52), AA'n1-70 (SEQ ID NO: 53-54) and AB'n1-70 (SEQ ID NO: 55-56). The pRSETb leader sequence is shown in Italic (leader includes Met, which is also amino acid 1 of FliC). The N terminal constant domain is underlined. The amino acid linker sequence is in Bold. The C terminal constant domain is underlined. GST, if present, is highlighted.

FIGS. 15A-C show a comparison of amino acid sequences of the conserved amino (FIG. 15A) and carboxy (FIGS. 15B and 15C) terminus from 21 species of bacteria. The 13 conserved amino acids important for TLR5 activity are shown with shading. The amino acid sequences are identified by their accession numbers from TrEMBL (first letter=Q) or Swiss-Prot (first letter=P). The amino terminus sequences have SEQ ID NOs: 57-77, respectively, for each of the 21 bacterial species, and the carboxy terminus sequences have SEQ ID NOs: 78-98, respectively.

DETAILED DESCRIPTION

Figure 1:
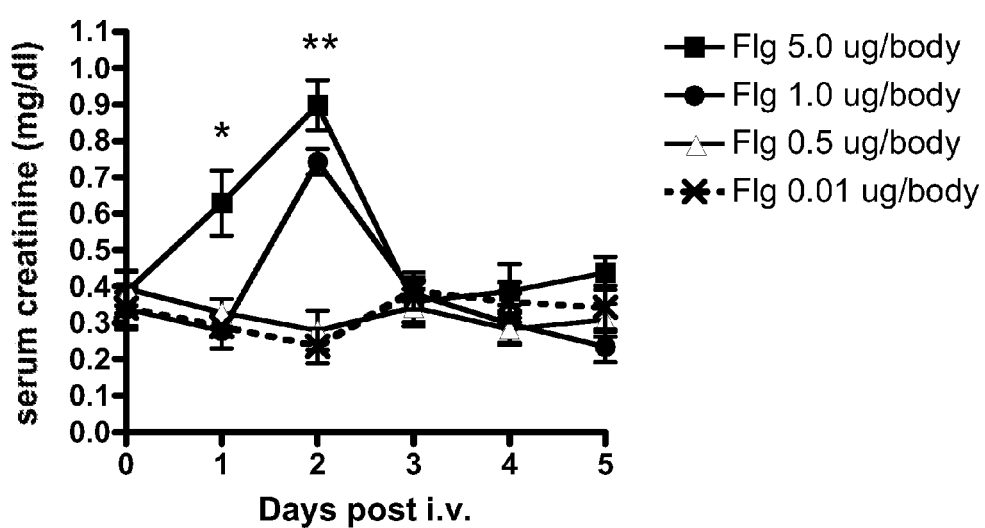
FIG. 1 demonstrates the level of creatinine in the serum of mice over 5 days post intravenous administration of flagellin at concentrations of either 0.01 µg, 0.5 µg, 1.0 µg, or 5.0 µg/body.

The inventors have made the surprising discovery that flagellin protects from the effects of reperfusion. The absence or reduction of oxygen and nutrients from blood creates a condition in which the restoration of circulation results in inflammation and oxidative damage through the induction of oxidative stress rather than the restoration of normal function. The restored blood flow reintroduces oxygen within cells that damages cellular proteins, DNA and the plasma membrane. Damage to cell's membrane may in turn cause the release of more free radicals. Such reactive species also act in redox signaling to induce apoptosis of ischemic tissue cells. In addition, inflammatory response further damages the tissue.

White blood cells carried to the area by the newly returning blood release a host of inflammatory factors such as interleukins as well as free radicals in response to tissue damage. Leukocytes may also build up in small capillaries, obstructing them and leading to more ischemia. While not being bound by theory, flagellin may provide protection from the effects of reperfusion by reducing the oxidative and inflammatory stresses to the tissue thereby preventing apoptosis and allowing faster recovery of the tissue to a normal state. This protective nature of flagellin can either by used at the onset of reperfusion or be used to prevent further damage due to reperfusion. The below-described invention relates in part to administration of flagellin to a treat tissue of a mammal from the effects of reperfusion.

1. DEFINITIONS

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Administer" may mean a dosage of an agent that induces NF-κB activity, means a single dose or multiple doses of the agent.

"Analog" may mean, in the context of a peptide or polypeptide, a peptide or polypeptide comprising one or more nonstandard amino acids or other structural variations from the conventional set of amino acids.

"Antibody" may mean an antibody of classes IgG, IgM, IgA, IgD or IgE, or fragments, fragments or derivatives thereof, including Fab, F(ab')$_2$, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibody may also be a chimeric antibody. The antibody may be derivatized by the attachment of one or more chemical, peptide, or polypeptide moieties known in the art. The antibody may be conjugated with a chemical moiety.

"Apoptosis" may mean a form of cell death that includes progressive contraction of cell volume with the preservation of the integrity of cytoplasmic organelles; condensation of chromatin (i.e., nuclear condensation), as viewed by light or electron microscopy; and/or DNA cleavage into nucleosome-sized fragments, as determined by centrifuged sedimentation assays. Cell death occurs when the membrane integrity of the cell is lost (e.g., membrane blebbing) with engulfment of intact cell fragments ("apoptotic bodies") by phagocytic cells.

A "peptide" or "polypeptide" may mean a linked sequence of amino acids and may be natural, synthetic, or a modification or combination of natural and synthetic.

"Treating," "treatment," or "to treat" each may mean to alleviate, suppress, repress, eliminate, prevent or slow the appearance of symptoms, clinical signs, or underlying pathology of a condition or disorder on a temporary or permanent basis. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. TREATING THE EFFECTS OF REPERFUSION

Provided herein is a method of treating the effects of reperfusion by administering to a mammal in need thereof a composition comprising flagellin. Reperfusion may be caused by an injury.

Reperfusion may damage a body component when blood supply returns to the body component after the injury. The effects of reperfusion may be more damaging to the body component than the injury itself. There are several mechanism and mediators of reperfusion including oxygen free radicals, intracellular calcium overload, and endothelial dysfunction. Excessive quantities of reactive oxygen species, when reintroduced into a previously injured body component, undergo a sequential reduction leading to the formation of oxygen free radicals. Potent oxidant radicals, such as superoxide anion, hydroxyl radical, and peroxynitrite may be produced within the first few minutes of reflow to the body component and may play a crucial role in the development of reperfusion injury. Oxygen free radicals also can be generated from sources other than reduction of molecular oxygen. These sources include enzymes, such as xanthine oxidase, cytochrome oxidase, and cyclooxygenase, and the oxidation of catecholamines.

Reperfusion is also a potent stimulus for neutrophil activation and accumulation, which in turn serve as potent stimuli for reactive oxygen species production. Specifically, the main products of the neutrophil respiratory burst are strong oxidizing agents including hydrogen peroxide, free oxygen radicals and hypochlorite. Neutrophils are the most abundant type of phagocyte, normally representing 50 to 60% of the total circulating leukocytes, and are usually the first cells to arrive at the site of injured body component. Oxygen-derived free radicals produce damage by reacting with polyunsaturated fatty acids, resulting in the formation of lipid peroxides and hydroperoxides that damage the body component and impair the function of membrane-bound enzyme systems. Free radicals stimulate the endothelial release of platelet activating factor and chemokines such as neutrophil activator factor, chemokine (C—X—C motif) ligand 1, and chemokine (C—X—C motif) ligand 1 which attracts more neutrophils and amplifies the production of oxidant radicals and the degree of reperfusion injury. Reactive oxygen species also quench nitric oxide, exaggerating endothelial injury and tissue cell dysfunction. In addition to an increased production, there is also a relative deficiency in endogenous oxidant scavenging enzymes, which further exaggerates free radical-mediated cardiac dysfunction.

Reperfusion may further result in marked endothelial cell dysfunction. Endothelial dysfunction facilitates the expression of a prothrombotic phenotype characterized by platelet and neutrophil activation, important mediators of reperfusion. Once neutrophils make contact with the dysfunctional endothelium, they are activated, and in a series of well-defined steps (rolling, firm adherence, and transmigration) they migrate into areas of tissue injury through endothelial cell junctions as part of the innate immune response.

Changes in intracellular calcium homeostasis play an important role in the development of reperfusion. Reperfusion may be associated with an increase in intracellular calcium; this effect may be related to increased sarcolemmal calcium entry through L-type calcium channels or may be secondary to alterations in sarcoplasmic reticulum calcium cycling. In addition to intracellular calcium overload, alterations in myofilament sensitivity to calcium have been implicated in reperfusion. Activation of calcium-dependent proteases (calpain I) with resultant myofibril proteolysis has been suggested to underscore reperfusion injury, as has proteolysis of troponin.

Reperfusion of tissue cells subjected to an injury have an altered cellular metabolism, which in turn may contribute to delayed functional recovery. For example, an injury may induce anaerobic metabolism in the cell with a net production of lactate. Lactate release persists during reperfusion, suggesting a delayed recovery of normal aerobic metabolism. Likewise, the activity of mitochondrial pyruvate dehydrogenase (PDH) may be inhibited up to 40% after an injury and may remain depressed for up to 30 minutes after reperfusion.

Each of these events during reperfusion can lead to stress to the tissue cells and programmed cell death (apoptosis) and necrosis of the tissue cells. Apoptosis normally functions to "clean" tissues from wounded and genetically damaged cells, while cytokines serve to mobilize the defense system of the organism against the pathogen. However, under conditions of severe injury both stress response mechanisms can by themselves act as causes of death.

a. Flagellin

Figure 7:
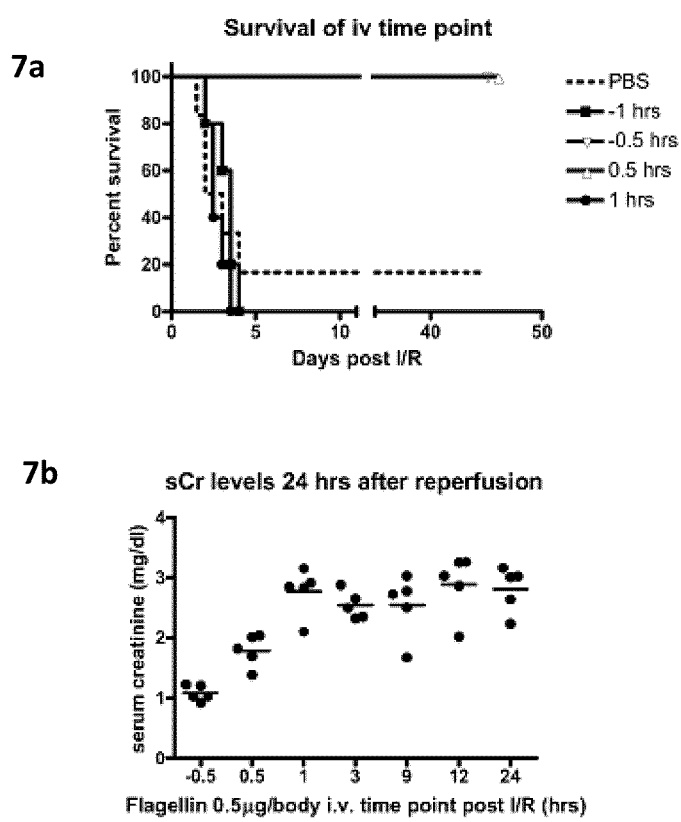
FIG. 7 demonstrates survival and creatinine levels in groups of C57BL/6 mice that were subjected to 45 minutes of bilateral renal pedicle occlusion and were administered 0.5 μg of flagellin at various times following the removal of the renal clamps.

The flagellin may be a flagellin-related polypeptide. The flagellin may be from any source, including a variety of Gram-positive and Gram-negative bacterial species. Flagellin may have the amino acid sequence of one of 23 flagellins from bacterial species that are depicted in FIG. 7 of U.S. Patent Publication No. 2003/0044429, the contents of which are incorporated herein by reference. The nucleotide sequences encoding the flagellin polypeptides listed in FIG. 7 of U.S. 2003/0044429 are publicly available at sources including the NCBI Genbank database.

Figure 10:
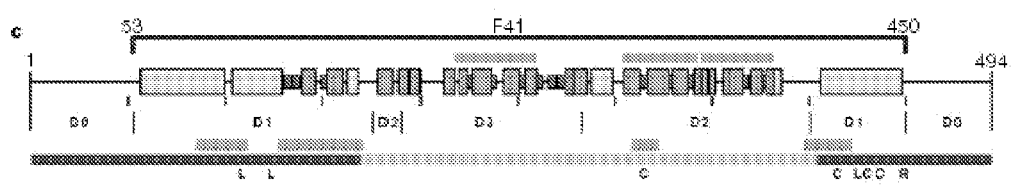
FIG. 10 shows the domain structure of bacterial flagellin. The Cα backbone trace, hydrophobic core distribution and structural information of F41. Four distinct hydrophobic cores that define domains D1, D2a, D2b and D3. All the hydrophobic side-chain atoms are displayed with the Cα backbone. Side-chain atoms are color coded: Ala, yellow; Leu, Ile or Val, orange; Phe and Tyr, purple (carbon atoms) and red (oxygen atoms). c, Position and region of various structural features in the amino-acid sequence of flagellin. Shown are, from top to bottom: the F41 fragment in blue; three b-folium folds in brown; the secondary structure distribution with a-helix in yellow, b-structure in green, and b-turn in purple; tic mark at every 50th residue in blue; domains D0, D1, D2 and D3; the axial subunit contact region within the proto-element in cyan; the well-conserved amino-acid sequence in red and variable region in violet; point mutations in F41 that produce the elements of different supercoils. Letters at the bottom indicate the morphology of mutant elements: L (D107E, R124A, R124S, G426A), L-type straight; R (A449V), R-type straight; C (D313Y, A414V, A427V, N433D), curly33.

Flagellin may be the major component of bacterial flagellum. Flagellin may be composed of three domains (FIG. 10). Domain 1 (D1) and domain 2 (D2) may be discontinuous and may be formed when residues in the amino terminus and carboxy terminus are juxtaposed by the formation of a hairpin structure. The amino and carboxy terminus comprising the D1 and D2 domains may be most conserved, whereas the middle hypervariable domain (D3) may be highly variable. Studies with a recombinant protein containing the amino D1 and D2 and carboxyl D1 and D2 separated by an *Escherichia coli* hinge (ND1-2/ECH/CD2) indicate that D1 and D2 may be bioactive when coupled to an ECH element. This chimera, but not the hinge alone, may includee IkBa degradation, NF-kB activation, and NO and IL-8 production in two intestinal epithelial cell lines. The non-conserved D3 domain may be on the surface of the flagellar filament and may contain the major antigenic epitopes. The potent proinflammatory activity of flagellin may reside in the highly conserved N and C D1 and D2 regions.

Flagellin may induce NF-kB activity by binding to Toll-like receptor 5 (TLR5). The TLR family may be composed of at least 10 members and is essential in innate immune defense against pathogens. The innate immune system may recognize pathogen-associated molecular patterns (PAMPs) that are conserved on microbial pathogens. TLR may recognize a conserved structure that is particular to bacterial flagellin. The conserved structure may be composed of a large group of residues that are somewhat permissive to variation in amino acid content. Smith et al., Nat. Immunol. 4:1247-53 (2003) have identified 13 conserved amino acids in flagellin that are part of the conserved structure recognized by TLR5. The 13 conserved amino acids of flagellin that may be important for TLR5 activity are shown in FIG. 11.

The flagellin may be from a species of *Salmonella*, a representative example of which is *S. dublin* (encoded by GenBank Accession Number M84972) (SEQ ID NO: 1). The flagellin related-polypeptide may be a fragment, variant, analog, homolog, or derivative of SEQ ID NO: 1, or combination thereof, that binds to TLR5 and induces TLR5-mediated activity, such as activation of NF-kB activity. A fragment, variant, analog, homolog, or derivative of flagellin may be obtained by rational-based design based on the domain structure of Flagellin and the conserved structure recognized by TLR5.

Figure 11:
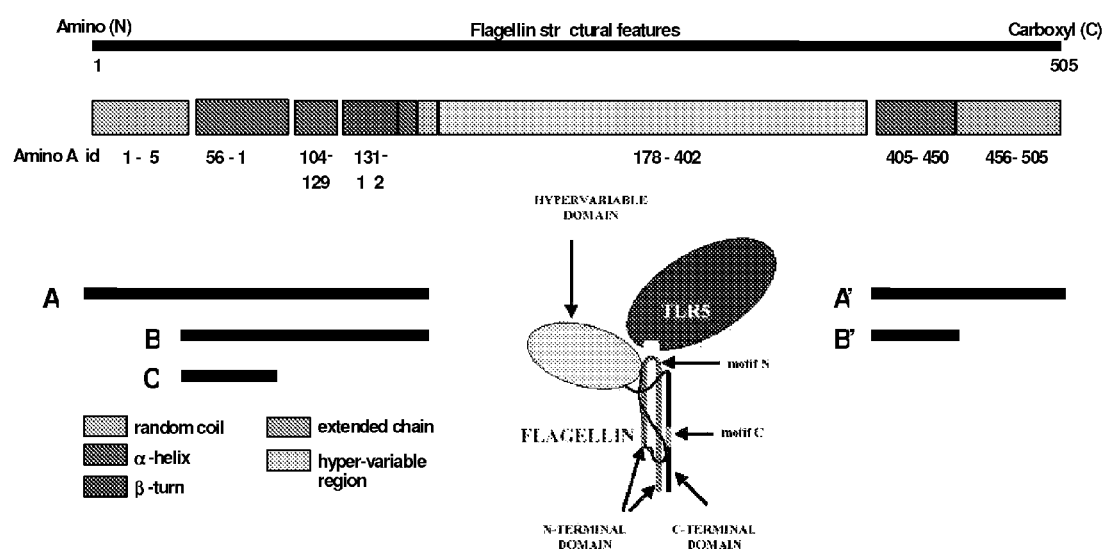
FIG. 11 shows a schematic of Salmonella flagellin domains, its fragments, and its interaction with TLR5. Dark bars denote regions of the flagellin gene used to construct fragments comprising A, B, C, A' and B'.
Figure 12:
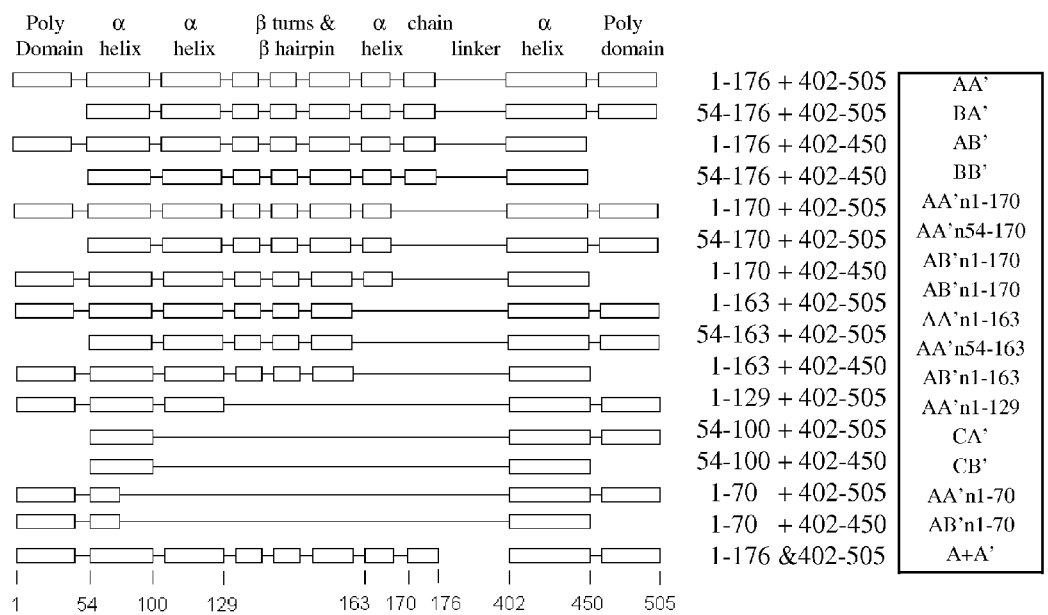
FIG. 12 depicts flagellin derivatives. The domain structure and approximate boundaries (amino acid coordinates) of selected flagellin derivatives (listed on the right). F11C flagellin of Salmonella dublin is encoded within 505 amino acids (aa).

The flagellin may comprise at least 10, 11, 12, or 13 of the 13 conserved amino acids shown in FIG. 11 (positions 89, 90, 91, 95, 98, 101, 115, 422, 423, 426, 431, 436 and 452). The flagellin may be at least 30-99% identical to amino acids 1 174 and 418 505 of SEQ ID NO: 1. FIG. 26 lists the percentage identity of the amino- and carboxy-terminus of flagellin with known TLR-5 stimulating activity, as compared to SEQ ID NO: 1.

The flagellin may be a flagellin polypeptide from any Gram-positive or Gram-negative bacterial species including, but not limited to, the flagellin polypeptides disclosed in U.S. Pat. Pub. 2003/000044429, the contents of which are incorporated herein, and the flagellin peptides corresponding to the Accession numbers listed in the BLAST results shown in FIG. 25 of U.S. Patent Pub. 2003/000044429, or variants thereof.

The flagellin may stimulate TLR5 activity. Numerous deletional mutants of flagellin have been made that retain at least some TLR5 stimulating activity. The flagellin may be a deletional mutant disclosed in the Examples herein, and may comprise a sequence translated from GenBank Accession number D13689 missing amino acids 185-306 or 444-492, or from GenBank Accession number M84973 missing amino acids 179-415, or a variant thereof.

The flagellin may comprise transposon insertions and changes to the variable D3 domain. The D3 domain may be substituted in part, or in whole, with a hinge or linker polypeptide that allows the D1 and D2 domains to properly fold such that the variant stimulates TLR5 activity. The variant hinge elements may be found in the *E. coli* MukB protein and may have a sequence as set forth in SEQ ID NOS: 3 and 4, or a variant thereof.

Other agents may be used to target TLR5 receptors. These agents may be agonists of TLR5 and stimulate TLR5 activity. The agonist may be an anti-TLR5 antibody or other small molecule.

b. Injury

The effects of reperfusion may be caused by an injury to the body component. The injury may be due to ischemia, hypoxia, an infarction, or an embolism. Treatment of the injury may lead to reperfusion and further damage to the body component.

(1) Ischemia

Ischemia may be an absolute or relative shortage of blood supply to a body component. Relative shortage may be a mismatch, however small, of blood supplied (oxygen delivery) to a body component vs. blood required to a body component for the adequate oxygenation. Ischemia may also be an inadequate flow of blood to a part of the body due to a constriction or blockage of blood vessels supplying it and may affect any body component in the body. Insufficient blood supply causes body components to become hypoxic, or, if no oxygen is supplied at all, anoxic. This may cause necrosis. The mechanisms of ischemia may vary greatly. For example, ischemia to any body component may be due to tachycardia (abnormally rapid beating of the heart), atherosclerosis (lipid-laden plaque obstructing the lumen of arteries), hypotension (low blood pressure in septic shock, heart failure), thromboembolisms (blood clots), outside compression of blood vessels (tumor), embolisms (foreign bodies in the circulation, e.g., amniotic fluid embolism), sickle cell disease (abnormally shaped hemoglobin), infarctions, induced g-forces which restrict the blood flow and force the blood to extremities of the body, localized extreme cold due to frostbite, ice, improper cold compression therapy, and any other force that restricts blood flow to the extremities such as a tourniquet. Force to restrict blood flow to extremities may be required due to severe lacerations, incisions, puncture such as a knifing, crushing injuries due to blunt force trauma, and ballistic trauma due to gunshot or shrapnel wounds. Ischemia may be a feature of heart diseases, ischemic colitis, transient ischemia attacks, cerebrovascular accidents, acute renal injury, ruptured arteriovenous malformations, and peripheral artery occlusive disease.

(2) Hypoxia

Hypoxia may be a deprivation of adequate supply of oxygen. Hypoxia may be pathological condition in which the body as a whole (generalized hypoxia) or region of the body (tissue hypoxia) is deprived of adequate oxygen supply. A variation in levels of arterial oxygen may be due to a mismatch between supply and demand of oxygen by body components. A complete deprivation of oxygen supply is anoxia. Hypoxia may be hypoxemic hypoxia, anemic hypoxia, hypoxemic hypoxia, histotoxic hypoxia, histotoxic hypoxia, and ischemic hypoxia.

Hypoxemic hypoxia may be an inadequate supply of oxygen to the body as a whole caused by low partial pressure of oxygen in arterial blood. Hypoxemic hypoxia may be due to low partial pressure of atmospheric oxygen such as at high altitudes, replacement of oxygen in breathing mix of a modified atmosphere such as a sewer, replacement of oxygen intentionally as in recreational use of nitrous oxide, a decrease in oxygen saturation of the blood due to sleep apnea, or hypopnea, inadequate pulmonary ventilation such as chronic obstructive pulmonary disease or respiratory arrest, anatomical or mechanical shunts in the pulmonary circulation or a right to left shunt in the heart and lung. Shunts may cause collapsed alveoli that are still perfused or a block in ventilation to an area of the lung. Shunts may present blood meant for the pulmonary system to not be ventilated and prevent gas exchange because Thebesia vessels empty into the left ventricle and the bronchial circulation, which supplies the bronchi with oxygen.

Anemia hypoxia may be the total oxygen content is reduced but the arterial oxygen pressure is normal. Hypoxemic hypoxia may be when blood fails to deliver oxygen to target body components. Hypoxemic hypoxia may be caused by carbon monoxide poisoning which inhibits the ability of haemoglobin to release the oxygen bound to it, or methaemoglobinaemia, an abnormal haemoglobin that accumulates in the blood.

Histotoxic hypoxia may be due to being unable to effectively use oxygen due to disabled oxidative phosphorylation enzymes.

(3) Infarction

Infarction is a is a type of pathological condition that can cause ischemia. Infarction may be a macroscopic area of necrotic tissue caused the loss of an adequate blood supply due to an occlusion. The infarction may be a white infarction composed of platelets and causes necrosis in organ tissues such as heart, spleen, and kidneys. The infarction may be a red infarction composed of red blood cells and fibrin strands in organ tissues of the lung. Disease associated with infarction may include myocardial infarction, pulmonary embolism, cerebrovascular accident (stroke), acute renal failure, peripheral artery occlusive disease (example being gangrene), antiphospholipid syndrome, sepsis, giant cell arthritis, hernia, and volvulus.

(4) Embolism

Embolism is a type of pathological condition that can cause ischemia. Embolism may be an object that migrates from one part of the body and causes an occlusion or blockage of a blood vessel in another part of the body. An embolism may be thromboembolism, fat embolism, air embolism, septic embolism, tissue embolism, foreign body embolism, amniotic fluid embolism. Thromboembolism may be a blood clot that is completely or partially detached from the site of thrombosis. Fat embolism may be endogenous fat tissues that escape into the blood circulation. The fracture of bones is one example of a leakage of fat tissue into the ruptured vessels and arteries. Air embolism may be a rupture of alveoli and inhaled air that leaks into the blood vessels. The puncture of the subclavian vein or intravenous therapy are examples of leakage of air into the blood vessels. A gas embolism may be gasses such as nitrogen and helium because insoluble and forming small bubbles in the blood.

c. Body Component

This invention relates to treatment of a body component in a mammal. The body component may be an organ, a tissue, or a cell. The body component may be from an abdomen, acetabulum, adipose, adrenal cortex, adrenal gland, adrenal medulla, alveolar macrophage, amnion, aorta, artery, ascites, ascitic fluid, axilla lymph node, bladder, blood, bone, bone marrow, bowel, brain, breast, bronchus, cartilage, caudal trunk, cerebellum, cervix, chorionic villi, colon, conjunctiva, connective tissue, cornea, dermis, dorsal root ganglion, duodenum, dysplastic tongue mucosa, egg, embryo, endocrine, endometrium, endothelium, epidermis, epithelium, erythropoietic, eye, fibroblast, fin, foetus, foot, foreskin, Gasser's node, gingival stroma, gonad, groin lymph node, heart, humerus, ileum, intestine, ileocecal, ileum, islets of Langerhanm, kidney, larvae, larval, larynx, liver, lung, lung (bronchioalveolar), lymph, lymph node, lymphatic tissue, lymphoid, lymphoid organs, mammary, mammary alveolar nodules, mammary gland, mesonephros, mesothelium, moulting nymph, mouth, muscle, nasal, nasal septum, nervous system, neural, oesophageal gastric junction, oesophagus, oral, ovary, palatal mesenchyme, pancreas, papillary ovarian, penis, peripheral blood, peritoneum, pharynx, pituitary, placenta, pleural effusion, pleural fluid, prostate, pupal ovary, rectum, retina, right axial lymph node, salivary duct, sialaden, skeletal muscle, skin, small bowel, small intestine, soft tissue, spleen, sternum, stomach, tail, testicle, testis, thigh, thymus, thyroid, thyroid glands, tongue, tonsil, trachea, trunk, turbinate, umbilical cord, umbilicus, uterus, vagina, viscera, vulva, GI tract, lungs, kidneys, liver, cardiovascular system, blood vessel endothelium, central and peripheral nervous system, muscle, bone, hair follicles, and yolk sac.

3. COMPOSITION

This invention also relates to a composition comprising a therapeutically effective amount of flagellin. The composition may be a pharmaceutical composition, which may be produced using methods well known in the art. The composition may also comprise a coagent. As described above, the composition may be administered to a mammal for treating the effects of reperfusion.

a. Administration

Administration of the compositions using the method described herein may be orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. For veterinary use, the composition may be administered as a suitably acceptable formulation in accordance with normal veterinary practice. The veterinarian can readily determine the dosing regimen and route of administration that is most appropriate for a particular animal. The compositions may be administered to a human patient, cat, dog, large animal, or an avian.

The composition may be administered simultaneously or metronomically with other treatments. The term "simultaneous" or "simultaneously" as used herein, means that the composition and other treatment be administered within 48 hours, preferably 24 hours, more preferably 12 hours, yet more preferably 6 hours, and most preferably 3 hours or less, of each other. The term "metronomically" as used herein means the administration of the composition at times different from the other treatment and at a certain frequency relative to repeat administration.

The composition may be administered at any point prior to reperfusion including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. prior to reperfusion. The composition may be administered at any point prior to the injury including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. prior to injury. The composition may be administered at any point after reperfusion including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr after reperfusion.

b. Formulation

The method may comprise administering a composition to treat for the effects of reperfusion. Compositions provided herein may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions provided herein may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions provided herein may also be formulated as suppositories, which may contain suppository bases including, but not limited to, cocoa butter or glycerides. Compositions provided herein may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions provided herein may also be formulated as transdermal formulations comprising aqueous or nonaqueous vehicles including, but not limited to, creams, ointments, lotions, pastes, medicated plaster, patch, or membrane.

Compositions provided herein may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions provided herein may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

c. Dosage

The method may comprise administering a therapeutically effective amount of the composition to a patient in need thereof. The therapeutically effective amount required for use in therapy varies with the nature of the condition being treated, the length of time desired to increase hematopoietic stem cells into the bloodstream, and the age/condition of the patient. In general, however, doses employed for adult human treatment typically are in the range of 0.001 mg/kg to about 200 mg/kg per day. The dose may be about 1 µg/kg to about 100 μg/kg per day. The desired dose may be conveniently administered in a single dose, or as multiple doses administered at appropriate intervals, for example as two, three, four or more sub-doses per day. Multiple doses may be desired, or required.

The dosage may be at any dosage including, but not limited to, about 0.1 μg/kg, 0.2 μg/kg, 0.3 μg/kg, 0.4 μg/kg, 0.5 μg/kg, 0.6 μg/kg, 0.7 μg/kg, 0.8 μg/kg, 0.9 μg/kg, 1 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg or 1 mg/kg.

4. COAGENT

Flagellin or the composition may be coadministered with a coagent. The coagent may be any compound that slows or prevents the effects of reperfusion. The coagent may be an antioxidant. The antioxidant may be able to slow and prevent the oxidation of other molecules, cells, tissues or organs. The antioxidant may be vitamin E, ascorbic acid, glutathione, lipoic acid, uric acid, carotenes such as β-carotene and retinol, vitamin E, and coenzyme Q, thiols such as cysteine, cysteamine, glutathione, and bilrubin, amifostine, and flavanoids.

The coagent may be a sodium-hydrogen antiport inhibitor. Injury and reperfusion may result in marked intracellular acidosis. A sodium-hydrogen antiport inhibitor may be used to reduce proton extrusion and prevent increases in Ca2+. A sodium-hydrogen inhibitor may be cariporide.

The coagent may be insulin. Insulin may be used to stimulate PDH activity and prevent inhibition of PDH activity after reperfusion.

The coagent may be adenosine. Adenosine may be used to open mitochondrial KATP channels.

5. COMBINATION TREATMENT

The method may be used in combination with other methods to treat the injury. The other methods may be treatments of myocardial infarction (heart attack), pulmonary embolism, cerebrovascular accident (stroke), peripheral artery occlusive disease (example being gangrene), antiphospholipid syndrome, sepsis, giant cell arteritis, hernia, volvulus, solid tumor cancers, decompression sickness, sickle cell anemia, puncture of the subclavian vein, bone fractures, high altitude sickness, recreational use of nitrous oxide, sleep apnea, hypopnea, shunts, anemia, carbon monoxide poisoning, methaemoglobinaemia, thromboembolism, fat embolism, air embolism, septic embolism, tissue embolism, foreign body embolism, amniotic fluid embolism, induced g-forces, and external pressure to prevent blood flow due to severe cuts, castration, or mangling. The method may also be used in combination with methods of treating reperfusion injuries such as administering low doses of hydrogen sulfate ($H_2S$), glisoden, or wheat glialin, or performing therapeutic hypothermia or aortic cross-clamping.

The present invention has multiple aspects, illustrated by the following non-limiting examples.

Example 1

Dose-Dependent Protection of Flagellin on Renal Function [Flagellin May be a TLR5 Agonist]

At particular dosages, flagellin does not affect renal function. This effect was demonstrated by measuring the levels of creatinine in the serum of mice after systemic administration of different dosages of flagellin. C57BL/6 mice were injected with either 0.01 μg, 0.5 μg, 1.0 μg, or 5.0 μg of flagellin and levels of serum creatinine (mg/dl) were monitored daily as shown in FIG. 1. Administration of 5 μg of flagellin resulted in increased serum concentrations that was evident within 24 hours after administration. After 24 additional hours (48 hours total), the levels of creatinine peaked and then fell back to background levels by 72 hours after administration and then began to slowly rise to low levels again (FIG. 1). In contrast, administration of 1 μg of flagellin also induced a rise in serum creatinine levels, but this was only detected as a single peak after 48 hours and then fell to background levels by 72 hours after administration. Administration of 0.5 μg and 0.1 μg did not induce any measurable increases in serum creatinine levels throughout the study period.

Example 2

Dose-Dependent Effect of Flagellin on Renal Function

At particular dosages, flagellin is capable of protecting renal tissue of a mammal from the effects of acute renal ischemia. This effect was demonstrated by administering flagellin to mice before imposition of renal ischemia and measuring survival following reperfusion of the ischemic kidneys. Specifically, 30 minutes before being subjected to 45 minutes of bilateral renal pedicle occlusion, groups of C57BL/6 mice were given either various doses of flagellin (0.01 μg, 0.5 μg, 1.0 μg, or 5.0 μg per body) in 400 μl of PBS or PBS alone (400 μl) via intravenous administration. Survival of the mice, levels of serum creatinine, and histopathology data were then collected.

a. Survival

Bilateral renal pedicle occlusion was performed in the mice as previously detailed. Mice were given 20 U (units/ml) sodium heparin via intraperitoneal administration 20 minutes before surgery. The mice were anesthetized with phenobarbital and kept warm under a 60-W light bulb until surgery. Under aseptic conditions, the abdominal cavity was opened with a midline incision and the bilateral renal pedicle was occluded nontraumatically with a microvascular clamp (World Precision Instruments, Sarasota, Fla.) and the wound was temporarily closed with 4-0 silk suture. Mice were placed on a heat pad under a 60 Watt light bulb and a sensor tip of the Traceable™ Certificate Memory Monitoring Thermometer (Fisher Scientific) was placed into the abdominal cavity to ensure temperature maintenance at 32° C. during the imposition of renal ischemia. Kidneys were subjected to ischemia for 45 minutes. After removal of the clamp, immediate and complete renal reperfusion was confirmed visually and the peritoneal cavity was closed. Sham-operated mice were treated in an identical manner except for the bilateral clamp of the renal pedicle.

Figure 2:
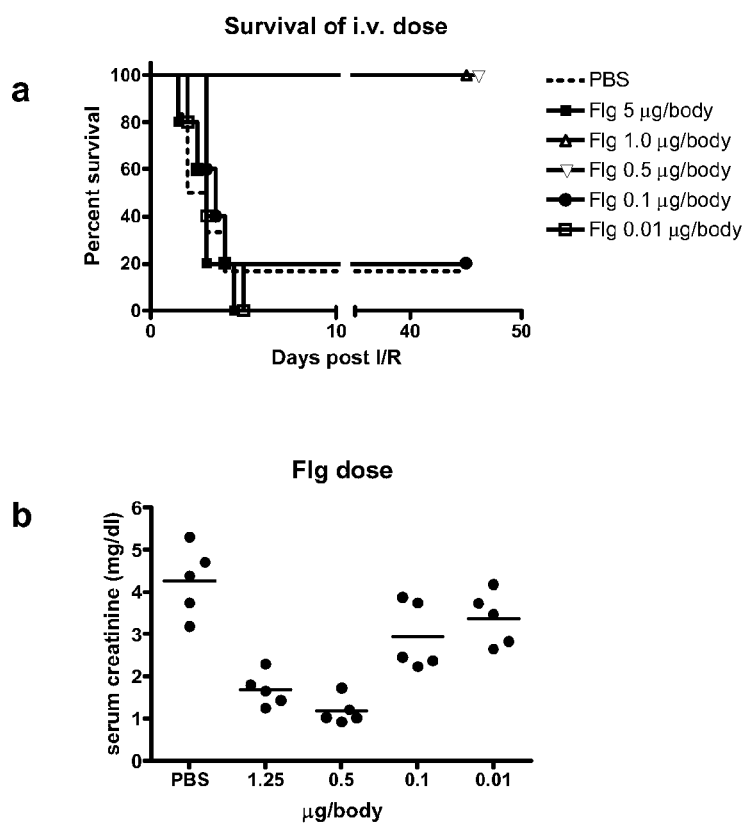
FIG. 2 demonstrates the affect of flagellin administered to mice before imposition of renal ischemia and measuring survival and creatinine following reperfusion of the ischemic kidneys. Panel A shows the percent survival of mice who were pretreated with flagellin at concentrations of either 0.01 µg, 0.5 µg, 1.0 µg, or 5.0 µg/body or PBS as a control. Panel B shows the level of creatinine in the same group of pretreated and control mice.

In the control group given PBS without flagellin, 80% of the animals expired within 5 days following reperfusion of the ischemic kidneys (see FIG. 2a). All animals given 5 μg of flagellin before imposition of renal ischemia expired within 5 days following reperfusion. In contrast, all animals given either 1 or 0.5 μg of flagellin before renal ischemia survived more than 45 days after reperfusion. The protective effect of flagellin in acute renal ischemia was also observed to be dose-dependent in that animals given 0.1 or 0.01 μg were not protected against the injury.

b. Renal Function Measurement

Serum creatinine levels were also measured to determine the protective effect of flagellin on renal function. Sham operated mice and mice subjected to bilateral renal I/R injury were anesthetized with isofluorane and bled from the postorbital plexus using a heparin-coated microcapillary tube at 24-hour intervals. The serum was stored at −80° C. until measurement. Serum creatinine levels were measured using the Creatinine Kit (Sigma Diagnostics, Inc., St. Louis, Mo.). The protective effect of flagellin was reflected by the low levels of serum creatinine determined at 24 hours post-reperfusion in animals given 1.25 or 0.5 μg flagellin 30 minutes before imposition of ischemia (see FIG. 2b). Animals given the non-protective low doses of flagellin (0.1 and 0.01 μg) had higher levels of creatinine levels that fell just below those observed in the control group that received PBS 30 minutes before bilateral pedicle occlusion.

c. Histology Studies of Renal Tissue

Figure 3:
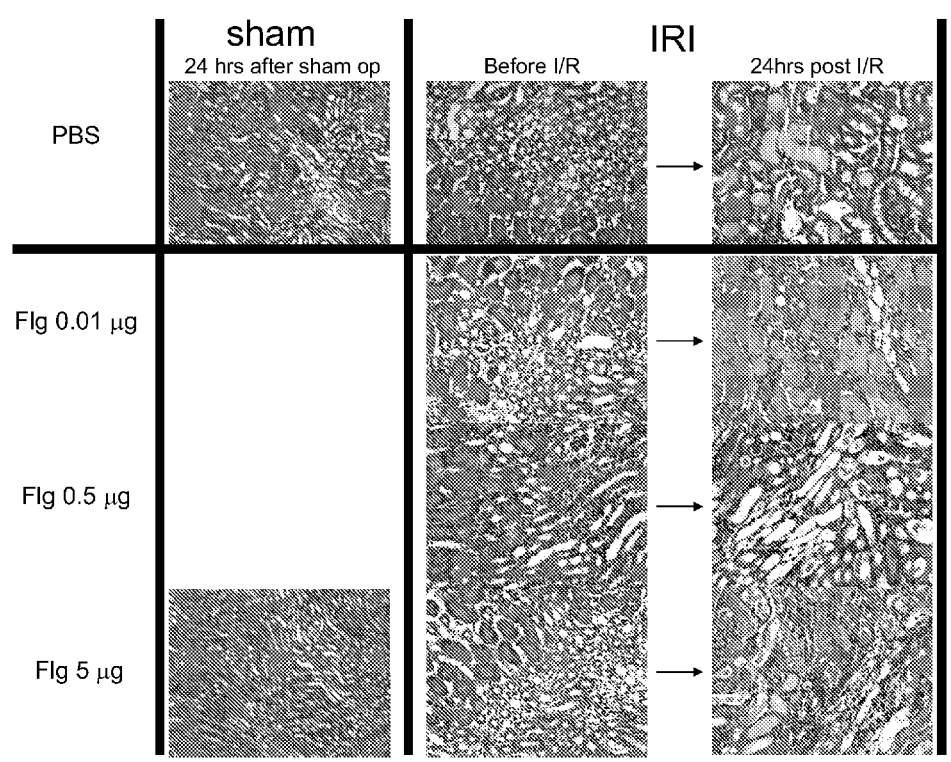
FIG. 3 demonstrates the histopathology of ischemic kidney cells 24 hours after reperfusion that were pretreated with PBS or flagellin at concentrations of either 0.01 µg, 0.5 µg, 1.0 µg, or 5.0 µg/body. The Sham column indicates kidney cells isolated from mice that were not imposed with renal ischemia.

High serum creatinine levels, an indication of renal dysfunction induced by imposition of ischemia-reperfusion injury, were supported by the histopathology of the ischemic kidneys 24 hours after reperfusion (see FIG. 3). For immunohistochemistry, retrieved kidneys were halved, embedded in OCT compound (Sakura Finetek U.S.A., Torrence, Calif.), and immediately frozen in liquid nitrogen. Coronal sections were cut (7 mm), mounted onto slides, dried for 1 hr, and then fixed in acetone for 10 minutes. Slides were immersed in PBS for 10 min and in 3% hydrogen peroxide/methanol for 5 minutes at room temperature to eliminate endogenous peroxidase activity. Endogenous biotin activity was blocked with the Biotin Blocking System (DAKO, Carpentaria, Calif.). After treating with normal rat serum (1:100), anti-mouse Gr-1 mAb (RB6.8C5) diluted at 1:100 in PBS with 1% bovine serum albumin (BSA) to detect neutrophils, or 1:50 dilutions of rat anti-mouse CD4 mAb (GK1.5) to detect CD4+ T cells, rat anti-mouse CD8a mAb (53-6.7) to detect CD8+ T cells, or rat anti-mouse macrophage (F4/80) mAb (SEROTEC, Raleigh, N.C.) was added to the sections. Control slides were incubated with rat IgG. After 1 hr, slides were washed 3× with PBS and incubated for 20 min with biotinylated rabbit anti-rat IgG antiserum (Sigma Aldrich) diluted 1:100 in PBS/1% BSA. After 3 washes in PBS, slides were incubated with streptavidin-horseradish peroxidase (DAKO) for 20 min. The DAB (3,3'-diaminobenzidine) substrate-chromagen solution (Vector Laboratories, Inc., Burlingame, Calif.) was applied to the slides for 0.5-3 min. After rinsing in dH2O, slides were counterstained with hematoxylin, washed with dH2O, cover-slipped, and viewed by light microscopy. Images were captured using Image Pro Plus (Media Cybernetics, Silver Spring, Md.).

To stain TLR5, 1 mg of anti-TLR5 mAb (ABR-Affinity BioReagents, Inc., Golden, Colo.) was applied to slides and incubated for 1 hr at room temperature and after washing biotinylated goat anti-mouse IgG antibody diluted 1:100 for 30 min at room temperature. After applying the DAB, the slides were washed with tap water, dipped for 3 sec in hematoxylin and then washed. The slides were dehydrated with increasing concentrations of ethanol to 50% and then immersed in citrasolve twice for 10 min each. The slides were washed with tap water, cover-slipped, and viewed by light microscopy.

Figure 4:
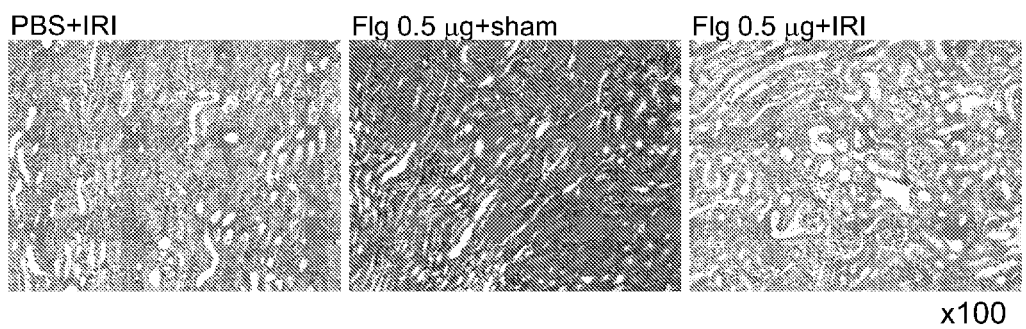
FIG. 4 demonstrates histopathology of kidney cells 7 days after reperfusion. In the first panel, the histopathology slide shows kidney cells isolated from mouse pretreated with PBS before renal ischemia and followed by reperfusion of the ischemic kidneys. In the first panel, the histopathology slide shows kidney cells isolated from mouse pretreated with PBS before renal ischemia and followed by reperfusion of the ischemic kidneys. In the second panel, the histopathology slide shows kidney cells isolated from mouse pretreated with flagellin at a concentration of 0.5 µg/body but not imposed with renal ischemia. The third panel demonstrates a histopathology slide showing kidney cells isolated from a mouse pretreated with flagellin at a concentration of 0.5 µg/body and imposed with renal ischemia and followed by reperfusion of the ischemic kidneys.

The use of serum creatinine levels as an indication of renal dysfunction induced by imposition of ischemia-reperfusion injury was supported by the histopathology of the ischemic kidneys 24 hours after reperfusion (see FIG. 3). Control group animals given PBS 30 min before imposition of renal ischemia had severe tubular necrosis with caste formation evident 24 hours after reperfusion. Consistent with the induction of renal dysfunction by administration of 5 μg of flagellin, there was evidence of renal pathology 30 min after administration of 5 μg of flagellin without imposing ischemia and this increased in severity following imposition of renal ischemia and reperfusion with obvious hemorrhage, thrombosis, and caste formation. In contrast, animals given 0.5 μg flagellin 30 min before imposition of ischemia had low levels of leukocytic infiltration 24 hours after reperfusion but the renal architecture appeared relatively normal. The low, non-protective dose, 0.1 μg flagellin, did not rescue the renal pathology induced by ischemia/reperfusion injury. When kidneys of surviving animals were examined at day 7 post-reperfusion, marked decreases in tubular necrosis and leukocytic infiltration as well as the absence of thrombosis and case formation were observed in animals given 0.5 μg flagellin prior to imposition of renal ischemia. (see FIG. 4).

d. Neutrophil Infiltration to Damaged Renal Tissue

Since neutrophil infiltration and activation is a major contributor to the tissue injury following renal ischemia-reperfusion, ischemic kidneys were retrieved 9 and 24 hours after reperfusion from animals treated with PBS alone or with 0.5 μg flagellin before imposition of ischemia and the levels of neutrophil infiltration was assessed by immunohistochemical staining of prepared tissue sections.

To directly determine the number of neutrophils, macrophages, CD4+ T cells and CD8+ T cells in ischemic kidneys during reperfusion, one quarter pieces of the retrieved kidney were cut and weighed. The kidneys were incubated in RPMI 1640 culture medium with 2% fetal calf serum for 1 hr and then were pushed through a 70 mm cell strainer using a syringe plunger. The cells were collected and the erythrocytes lysed using ACK Lysing Buffer (GIBCO, Grand island, NY). After 2 washes, viable cells were counted using Trypan blue exclusion. Aliquots of the cells were preincubated with anti-CD16/CD32 Fc receptor antibody (BD Pharmingen, San Diego, Calif.) for 5 min to block nonspecific antibody binding and then samples were incubated with FITC-conjugated anti-CD45 mAb as well as PE-conjugated antibody to detect macrophages (F4/80) or CD8+ T cells (53-6.7) and APC-conjugated antibody to detect neutrophils (RB6.8C5) or CD4+ T cells (GK1.5) (all antibodies from BD Pharmingen) for 30 min at 4° C. Cells were analyzed using two-color flow cytometry on a FACSCalibur (BD Biosciences, San Jose, Calif.). The forward scatter and FL1 (CD45+) channels were used to gate the leukocytes in the kidney tissue followed by analysis of the specific leukocyte populations. For each sample, 200,000 events were accumulated. The data were analyzed using CellQuest software (BD Biosciences). Total numbers of each leukocyte population were calculated by: (the total number of leukocytes counted)×(% of the leukocyte population counted in the CD45+ cells)/100. The data are reported as number of each leukocyte population/g kidney tissue from sham and I/R animals.

Figure 5A:
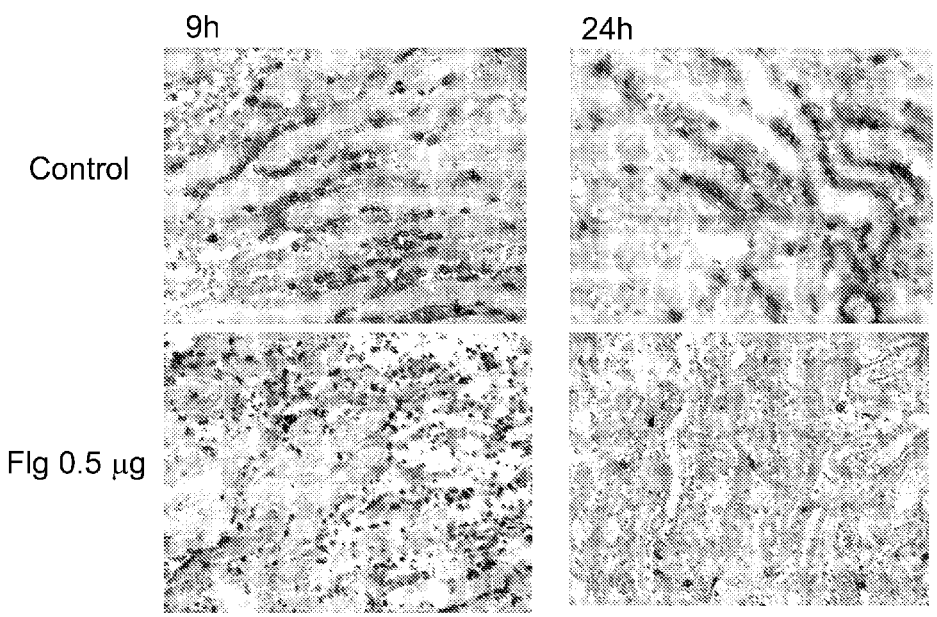
FIGS. 5a-5c demonstrate assessing leukocyte infiltration 9 hours and 24 hours after reperfusion into ischemic kidney cells isolated from mice pretreated with PBS or flagellin at 0.5 µg/body.
Figure 5B:
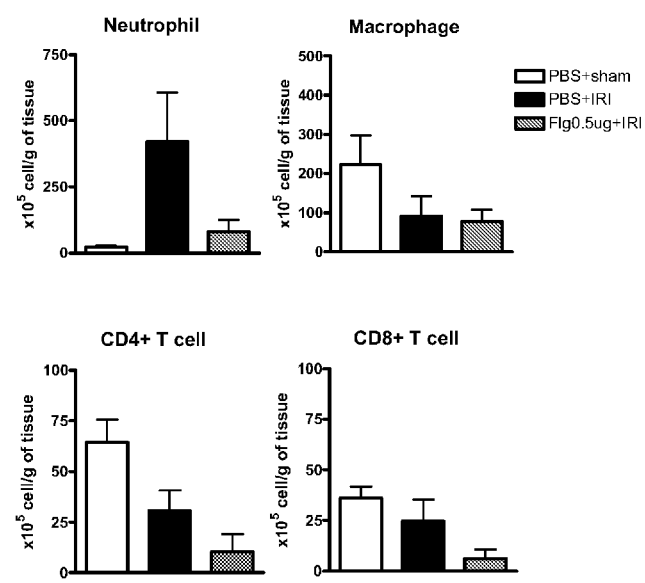
Figure 5C:
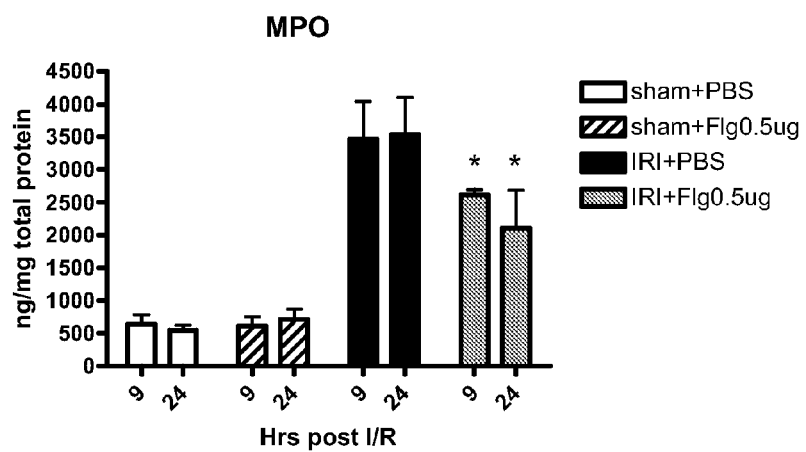

Marked decreases in neutrophil infiltration were observed 9 and 24 hours after reperfusion when animals were given 0.5 μg flagellin (see FIG. 5a). Direct quantitation of leukocytic infiltration into the ischemic kidneys indicated that 0.5 ug flagellin reduced neutrophil infiltration almost to the levels observed in the sham-operated control animals (see FIG. 5b). Decreases in the number of CD4 and CD8 T cells and macrophages were observed in ischemic kidneys 24 hours after reperfusion and administration of 0.5 μg of flagellin 30 minutes before ischemia decreased the number of both CD4 and CD8 T cells further.

Example 3

Flagellin Condition Decreases Pro-Inflammatory Cytokine Expression During Reperfusion of Ischemic Kidneys This example demonstrates the critical role of flagellin preventing chemokines CXCL1/KC and CXCL2/KC in directing leukocyte infiltration into ischemic kidney tissues. Previous studies have indicated that peak levels of the neutrophil chemoattractants CXCL1/KC and CXCL2/KC in ischemic kidneys occurs at 9 hours post-reperfusion [REFERENCE]

Figure 6A:
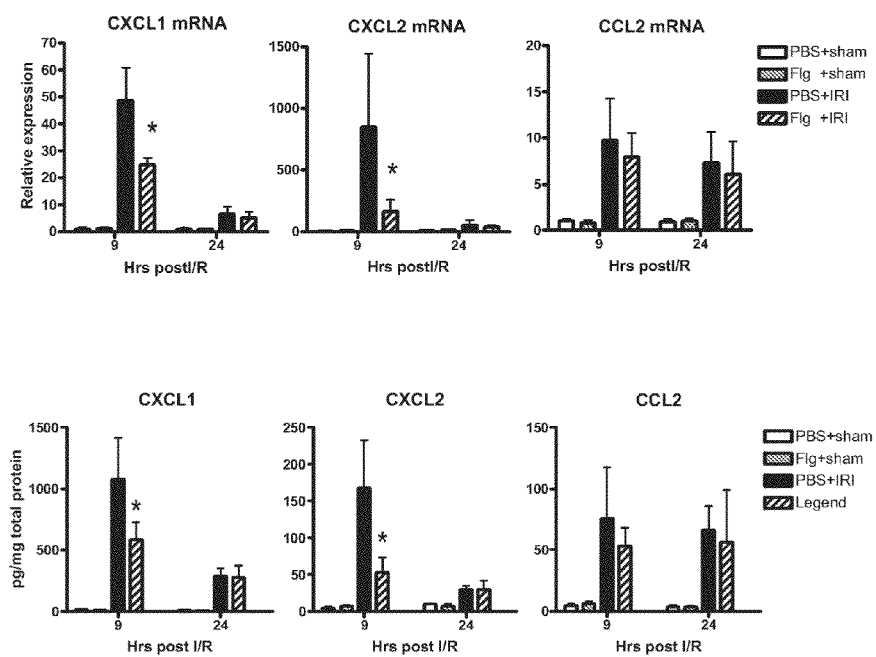
FIG. 6a demonstrates critical role of flagellin preventing chemokines CXCL1/KC and CXCL2/KC in directing leukocyte infiltration into ischemic kidney tissues.

To begin to investigate mechanisms underlying the decreased leukocytic infiltration into ischemic kidneys when animals were conditioned with 0.5 ug flagellin, kidneys were removed 9 and 24 hours after reperfusion and the mRNA and protein levels of neutrophil and macrophage chemoattractants were determined (FIG. 6a). One-quarter pieces were cut from harvested kidneys and frozen in liquid nitrogen. Total tissue RNA was extracted using RNeasy™ Mini Kit (QIAGEN, Valencia, Calif.) and reverse transcribed using the High-Capacity cDNA Archive Kit (Applied Biosystems, Foster City, Calif.). Real time PCR was performed on a Prism 7700 Sequence Detection System (Applied Biosystems, Foster City, Calif.) with test KC/CXCL1, MIP-2/CXCL2 and MCP-1/CCL2 primers and Mrp132 used as the control (Applied Biosystems, Foster City, Calif.).

Kidneys samples stored in liquid nitrogen were dissolved in 500 ml of PBS with 0.01M EDTA and a proteinase inhibitor cocktail (10 mg/ml phenylmethyl solfonyl fluoride, 2 mg/ml aprotinin, 2 mg/ml leupeptin, 100 mg/ml Pefabloc SC, and 100 mg/ml chymostatin), and then 1 ml of 1.5% Triton X-100 in PBS was added. After incubation with agitation for 1 hr at 4° C., samples were centrifuged, the supernatant was collected, and the total protein concentration was determined using the BCA™ Protein Assay Kit (Pierce, Rockford, Ill.). KC/CXCL1, MIP-2/CXCL2 and MCP-1/CCL2 concentrations were measured by sandwich ELISA using Quantikine M Kits (R&D Systems, Minneapolis, Minn.). To determine the activation of neutrophils during reperfusion of ischemic kidneys, the concentration of myeloperoxidase (MPO) was measured using the Mouse MPO ELISA test kit (Cell Sciences, Canton, Mass.). Results are reported as concentration of test protein per mg of total tissue protein±SD.

Figure 6B:
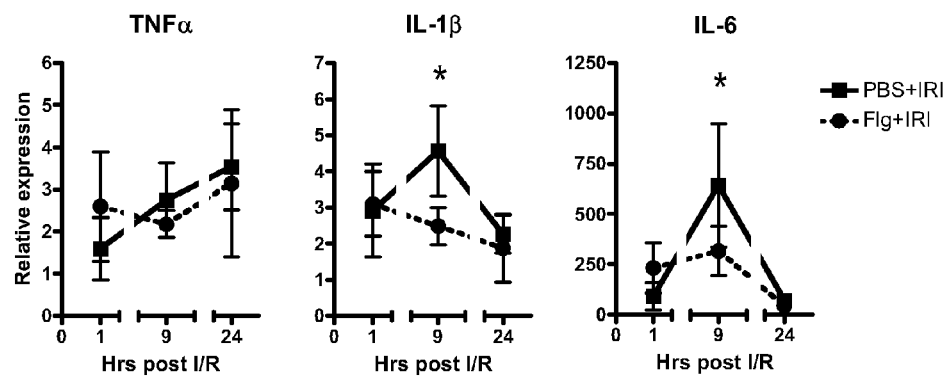
FIG. 6b demonstrates mRNA levels of the acute phase proteins IL-1b and IL-6 but not TNFa were also decreased in ischemic kidneys at 9 hours post-reperfusion in flagellin preconditioned animals.

Preconditioning with protective doses of flagellin (1.25 or 0.5 ug) resulted in significant decreases in mRNA expression and protein levels of the neutrophil chemoattractants CXCL1 and CXCL2 at 9 hours post-reperfusion. Expression of CCL2 mRNA or protein levels were low at both 9 and 24 hours after reperfusion and were not further influenced by preconditioning with flagellin. In addition, mRNA levels of the acute phase proteins IL-1b and IL-6 but not TNFa were also decreased in ischemic kidneys at 9 hours post-reperfusion in flagellin preconditioned animals (FIG. 6b).

Example 4

Protective Effect of Flagellin when Administered During Reperfusion of Ischemic Kidneys This example demonstrates that flagellin provides a protective effect to acute ischemic treated kidneys when given after the initiation of reperfusion. As described above, bilateral renal pedicle occlusion was performed in the mice and serum creatinine levels were measured to determine the protective effect of flagellin on renal function after initiation of reperfusion.

Specifically, groups of C57BL/6 mice were subjected to 45 minutes of bilateral renal pedicle occlusion and were administered 0.5 µg of flagellin at various times following the removal of the renal clamps (See FIG. 7). Administration of flagellin 30 minutes before or within 30 min after declamping rescued the viability of all mice subjected to the ischemic injury. Flagellin administration 1 hour as well as at later times after initiation of reperfusion failed to rescue any of the mice from the injury. The protective effect of administering the flagellin 30 minutes before declamping or within 30 minutes following declamping was reflected by the low levels of serum creatinine monitored 24 hours after reperfusion of the ischemic kidneys (FIG. 7b).

Example 5

Protective Effect of Flagellin Requires TLR5 Signaling on Renal Parenchymal Cells This example demonstrates the target source of protective effect of flagellin treatment during reperfusion of tissue. As discussed in Examples 1-4, reperfusion studies were performed on ischemic kidneys.

Radiation-induced bone marrow reconstituted chimeras were generated between wild-type C57BL/6 and B6.MyD88$^{-/-}$ mice. Radiation-induced bone marrow reconstituted chimeras were generated by cutting the tips of femurs and tibias from wild-type C57BL/6 and B6.MyD88$^{-/-}$ mice and flushing with RPMI 1640 to collect the bone marrow cells. Bone marrow recipient mice first received 1100 Rad g-irradiation and then 3 hours later received 20×10$^6$ bone marrow cells intravenously. Irradiated CD90.1 recipients received bone marrow from congenic CD90.1 donors or vice versa. The reconstituted recipients received antibiotics (0.2 mg/ml sulfamethoxazole and 0.4 mg/ml trimethoprim) in the drinking water from day 1 to 7 as prophylaxis. The recipients were allowed to recover for 8-12 weeks and complete chimerism was confirmed by staining peripheral blood cells with FITC-conjugated 90.2 and PE-conjugated 90.1.

Figure 8:
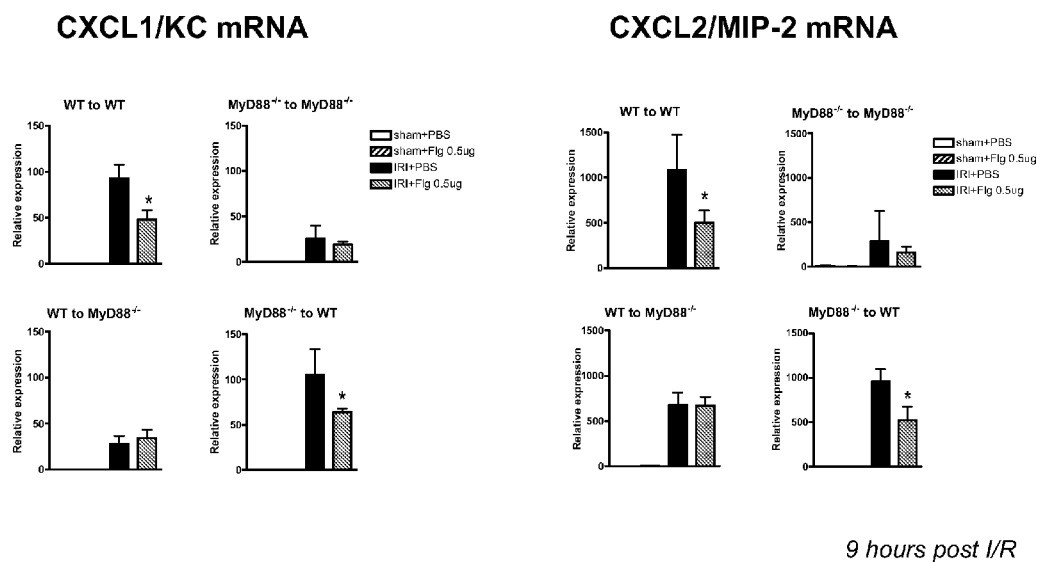
FIG. 8 demonstrates administration of 0.5 μg flagellin within 30 minutes of reperfusion of ischemic kidneys of wild-type C57BL/6 mice reconstituted with wild-type bone marrow decreased CXCL1 and CXCL2 mRNA levels. In MyD88$^{-/-}$ recipients reconstituted with either MyD88$^{-/-}$ or wild-type bone marrow, little CXCL1 and CXCL2 mRNA was induced during reperfusion of ischemic kidneys and administration of flagellin during reperfusion of these kidneys did not decrease the mRNA levels of these chemokines. In contrast, wild-type recipients of bone marrow from MyD88$^{-/-}$ donors expressed high levels of CXCL1 and CXCL2 mRNA and these levels were decreased by administration of flagellin during reperfusion of the ischemic kidneys.

FIG. 8 shows that administration of 0.5 µg flagellin within 30 minutes of reperfusion of ischemic kidneys of wild-type C57BL/6 mice reconstituted with wild-type bone marrow decreased CXCL1 and CXCL2 mRNA levels. In MyD88$^{-/-}$ recipients reconstituted with either MyD88$^{-/-}$ or wild-type bone marrow, little CXCL1 and CXCL2 mRNA was induced during reperfusion of ischemic kidneys and administration of flagellin during reperfusion of these kidneys did not decrease the mRNA levels of these chemokines. In contrast, wild-type recipients of bone marrow from MyD88$^{-/-}$ donors expressed high levels of CXCL1 and CXCL2 mRNA and these levels were decreased by administration of flagellin during reperfusion of the ischemic kidneys. This demonstrates that the target of the flagellin was a parenchymal kidney cell rather than a leukocyte.

Figure 9A:
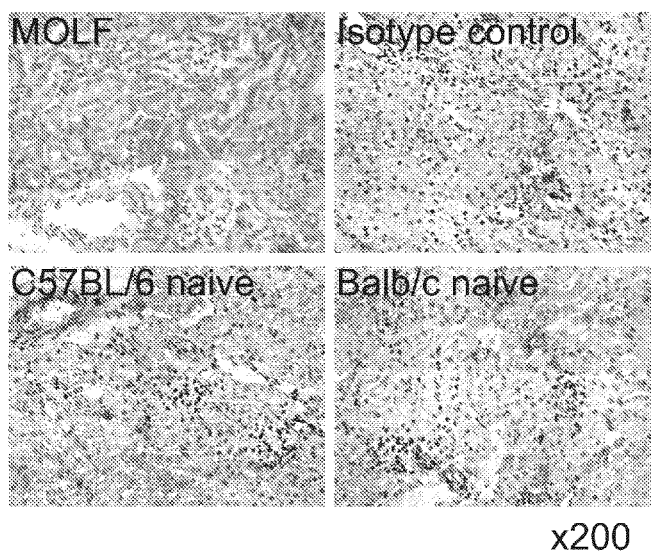
FIG. 9a demonstrates renal sections from wild-type C57BL/6 and BALB/c mice were stained with anti-TLR5 antibody.
Figure 9B:
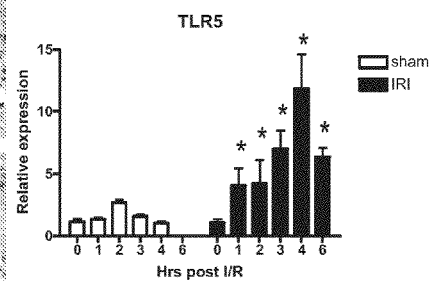
FIG. 9b demonstrates expression levels of TLR5 mRNA were low in kidneys prior to imposition of renal ischemia/reperfusion but increased quickly during reperfusion of ischemic kidneys.

To investigate this further, renal sections from wild-type C57BL/6 and BALB/c mice were stained with anti-TLR5 antibody (FIG. 9a). The cells staining positively were primarily cells in the vasculature and staining was not apparent on renal tubular cells or glomeruli. Kidney sections from Moth Eaten mice that have a genetic defect in the expression of TLR 5 did not stain with the anti-TLR5 antibody. Expression levels of TLR5 mRNA were low in kidneys prior to imposition of renal ischemia/reperfusion but increased quickly during reperfusion of ischemic kidneys (FIG. 9b).

Example 6

Protective Effect of Flagellin in Hind Limb Ischemia Model

The potential protective effects of CBLB502 in a mouse hind limb ischemia model were investigated in a simulation of a tourniquet-induced ischemic injury. These studies originated from studies indicating that CBLB502 given to mice subjected to bilateral renal pedicle occlusion attenuated ischemic injury and renal dysfunction including decreased neutrophil chemoattractant production in response to reperfusion, decreased neutrophil infiltration into the ischemic kidney, and attenuation of rises in serum creatinine levels and loss of viability. The protectant could be given either before imposition of renal pedicle occlusion, or more importantly for clinical use, up to 30 min after reperfusion of the ischemic kidney.

The tourniquet-induced injury was modeled by tightening a wide rubber band on the left hind limb of mice for 2-4 hours. After the ischemic time, the rubber band was loosened and removed. The animals recovered from anesthesia but exhibited an inability to use the ischemic limb, which was dragged behind them for periods of up to 9 days. The ischemic injury also included edema of the limb that was clearly visible and that was quantified by wet-dry weight measures and comparison with the contralateral, non-ischemic hind limb, and induction of high levels of proinflammatory cytokines including neutrophil chemoattractants and intense neutrophil infiltration into the ischemic limb. In addition, injection of Evan's blue dye indicated considerable amounts of vascular leak in the ischemic limb (data not shown).

Figure 14:
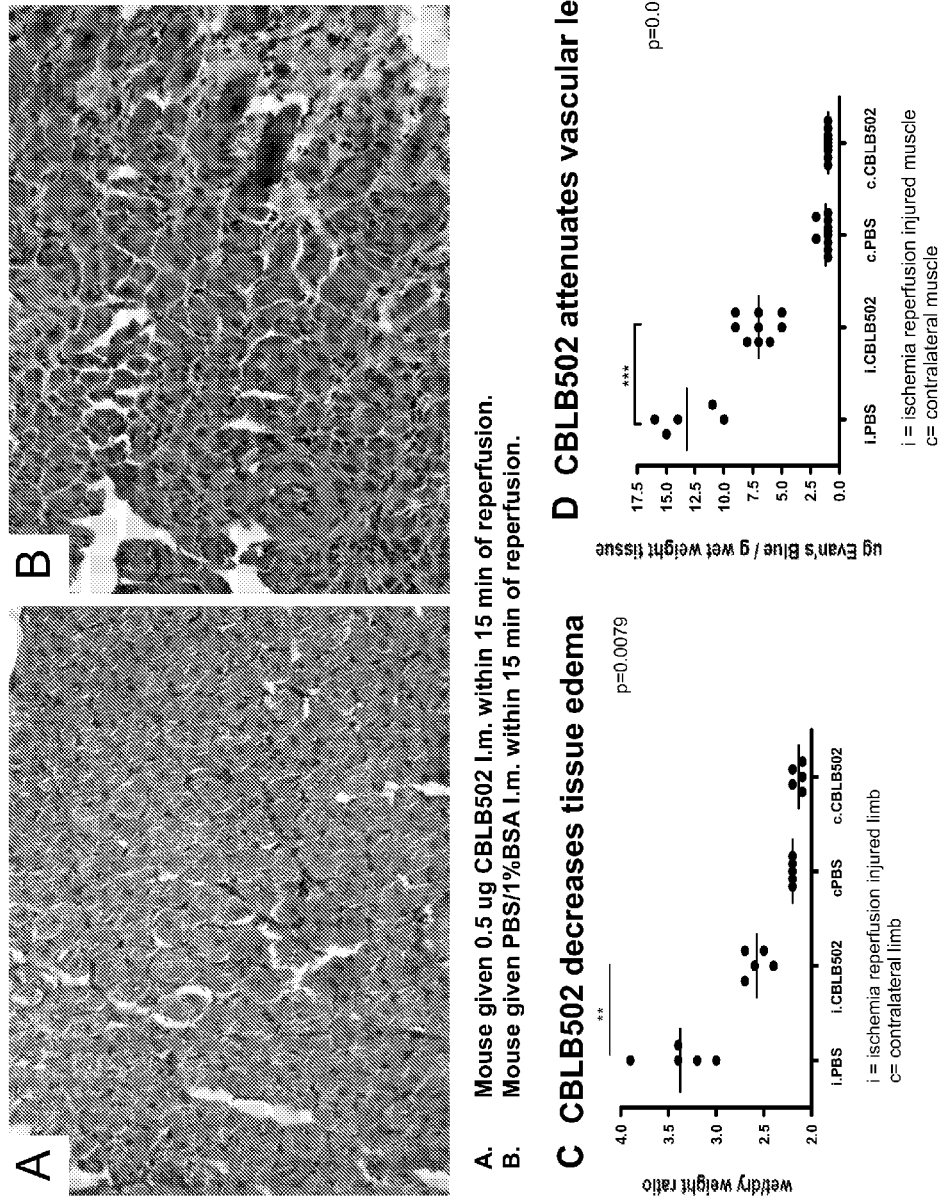
FIG. 14A shows histological section of mice hind limb muscle 14 days after reperfusion following 3 hours of warm ischemia using a hematoxylin/eosin stain where the mouse had been given 0.5 μg of CBLB502 within 15 minutes of reperfusion.
FIG. 14B shows histological section of mice hind limb muscle 14 days after reperfusion following 3 hours of warm ischemia using a hematoxylin/eosin stain where the mouse had been given vehicle (PBS) within 15 minutes of reperfusion.
FIG. 14C shows the wet/dry ratio of tissue edema in the limb of mice administered either with CBLB502 or PBS within 15 minutes of reperfusion after 3 hours of ischemia. The ratio of edema was also measured in the limb of mice administered CBLB502 or PBS, but spared 3 hours of ischemia.
FIG. 14D shows the wet/dry ration of vascular leaks using Blue Dye per gram weight limb of mice administered either CBLB502 or PBS within 15 minutes of reperfusion after 3 hours of ischemia. The ratio of vascular leaks was also measured in the limb of mice administered CBLB502 or PBS, but spared 3 hours of ischemia.

Studying the protective effects of CBLB502, mice were again subjected to a tourniquet-induced injury by tightening a wide rubber band on the left hind limb for 3 hours. After the ischemic time, the rubber bank was loosened and removed. Fifteen minutes upon removal of the rubber band and initiation of reperfusion, 0.5 µg of CBLB502 or vehicle (PBS) was administered intramuscularly into the left ischemic limb. Mice administered the CBLB502 has a more rapid recovery of limb usage and, by day 14 posted reperfusion, had a measurable grip strength for the ischemic limb of 10 GF. In contrast, mice administered only PBS 15 minutes post reperfusion did not achieve this strength until day 21. Limbs given CBLB502 also had almost no evidence of edema 25 hours after reperfusion as evidence by a wet/dry weight ratio of 2.5 vs. 3.4 for the ischemic limb from mice given only vehicle at reperfusion (See FIG. 14C). With regard to vascular leak, the CBLB501 administered mice had a 7.4 µg Evan's Blue Dye per gram web weight limb tissue vs. 13.1 µg for vehicle administered mice, P<0.001) (See FIG. 14D). Finally, limbs treated with CBLB502 at reperfusion had significant decreases in tissue neutrophil and macrophage chemoattractant sCXCL2, CCL2, and myeloperoxidase (P<0.05 for each assay). A hematoxylin/eosin stain was performed on the hind limb muscle on day 14 after reperfusion following 3 hours of ischemia on mice treated with CBLB502 (FIG. 14A) or vehicle (FIG. 14B).

Injection of CBLB502 within 30 min of reperfusion also resulted in decreases in neutrophil chemoattractant production and neutrophil infiltration into the ischemic limb, visible decreases in edema, and accelerated recovery (day 4-6) of the use of the ischemic limbs. Histological examination also indicated greater muscle fiber bundle thickness in the ischemic limbs of animals treated with the protectant (data not shown).

These results will be further investigated through quantitative measurement of inflammation and limb dysfunction in animals subjected to hind limb ischemia with vs. without administration of the CBLB502 protectant. This will include quantification of other proinflammatory cytokines, direct quantification of neutrophil infiltration, quantitation of muscle fiber bundle thickness and apoptosis of muscle fibers, and magnitude and duration of edema.

---

The invention claimed is:

1. A method of treating an injury to a mammal, comprising administering to the mammal a composition comprising flagellin,
   wherein the injury is tourniquet-induced injury to a limb of the mammal, and
   wherein the flagellin comprises the sequence of SEQ ID NO: 8.

2. The method of claim 1, wherein the tourniquet-induced injury is associated with reperfusion.

3. The method of claim 1, wherein the tourniquet-induced injury induces ischemia.

4. The method of claim 1, wherein the method reduces neutrophil chemoattractant production in the limb.

5. The method of claim 1, wherein the method reduces neutrophil infiltration in the limb.

6. The method of claim 1, wherein the method reduces edema in the limb.

7. The method of claim 1, wherein the method reduces inflammation in the limb.

8. The method of claim 1, wherein the method reduces apoptosis of ischemic cells in the limb.

9. The method of claim 1, wherein the method enhances muscle fiber bundle thickness in the limb.

10. The method of claim 1, wherein the composition is administered prior to, together with, or after the influx of oxygen resulting from reperfusion.

11. The method of claim 1, wherein the composition is administered in combination with an antioxidant.

12. The method of claim 11, wherein the antioxidant is selected from amifostine and vitamin E.

13. The method of claim 1, wherein the composition is administered by intramuscular injection.

* * * * *

SEQUENCE LISTING

<160> NUMBER OF SEQ ID NOS: 98

<210> SEQ ID NO 1
<211> LENGTH: 505
<212> TYPE: PRT
<213> ORGANISM: Salmonella dublin

<400> SEQUENCE: 1

```
Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110
```

```
Gln Asp Glu Ile Gln Gln Arg Leu Glu Glu Ile Asp Arg Val Ser Asn
            115                 120                 125
Gln Thr Gln Phe Asn Gly Val Lys Val Leu Ser Gln Asp Asn Gln Met
        130                 135                 140
Lys Ile Gln Val Gly Ala Asn Asp Gly Glu Thr Ile Thr Ile Asp Leu
145                 150                 155                 160
Gln Lys Ile Asp Val Lys Ser Leu Gly Leu Asp Gly Phe Asn Val Asn
                165                 170                 175
Gly Pro Lys Glu Ala Thr Val Gly Asp Leu Lys Ser Ser Phe Lys Asn
            180                 185                 190
Val Thr Gly Tyr Asp Thr Tyr Ala Ala Gly Ala Asp Lys Tyr Arg Val
        195                 200                 205
Asp Ile Asn Ser Gly Ala Val Val Thr Asp Ala Ala Pro Asp Lys
210                 215                 220
Val Tyr Val Asn Ala Ala Asn Gly Gln Leu Thr Thr Asp Asp Ala Glu
225                 230                 235                 240
Asn Asn Thr Ala Val Asp Leu Phe Lys Thr Thr Lys Ser Thr Ala Gly
                245                 250                 255
Thr Ala Glu Ala Lys Ala Ile Ala Gly Ala Ile Lys Gly Lys Glu
            260                 265                 270
Gly Asp Thr Phe Asp Tyr Lys Gly Val Thr Phe Thr Ile Asp Thr Lys
        275                 280                 285
Thr Gly Asp Asp Gly Asn Gly Lys Val Ser Thr Thr Ile Asn Gly Glu
290                 295                 300
Lys Val Thr Leu Thr Val Ala Asp Ile Ala Thr Gly Ala Ala Asp Val
305                 310                 315                 320
Asn Ala Ala Thr Leu Gln Ser Ser Lys Asn Val Tyr Thr Ser Val Val
                325                 330                 335
Asn Gly Gln Phe Thr Phe Asp Lys Thr Lys Asn Glu Ser Ala Lys
            340                 345                 350
Leu Ser Asp Leu Glu Ala Asn Asn Ala Val Lys Gly Glu Ser Lys Ile
        355                 360                 365
Thr Val Asn Gly Ala Glu Tyr Thr Ala Asn Ala Thr Gly Asp Lys Ile
370                 375                 380
Thr Leu Ala Gly Lys Thr Met Phe Ile Asp Lys Thr Ala Ser Gly Val
385                 390                 395                 400
Ser Thr Leu Ile Asn Glu Asp Ala Ala Ala Lys Lys Ser Thr Ala
                405                 410                 415
Asn Pro Leu Ala Ser Ile Asp Ser Ala Leu Ser Lys Val Asp Ala Val
            420                 425                 430
Arg Ser Ser Leu Gly Ala Ile Gln Asn Arg Phe Asp Ser Ala Ile Thr
        435                 440                 445
Asn Leu Gly Asn Thr Val Thr Asn Leu Asn Ser Ala Arg Ser Arg Ile
450                 455                 460
Glu Asp Ala Asp Tyr Ala Thr Glu Val Ser Asn Met Ser Lys Ala Gln
465                 470                 475                 480
Ile Leu Gln Gln Ala Gly Thr Ser Val Leu Ala Gln Ala Asn Gln Val
                485                 490                 495
Pro Gln Asn Val Leu Ser Leu Leu Arg
            500                 505

<210> SEQ ID NO 2
<211> LENGTH: 1518
<212> TYPE: DNA
```

<213> ORGANISM: Salmonella dublin

<400> SEQUENCE: 2

```
atggcacaag tcattaatac aaacagcctg tcgctgttga cccagaataa cctgaacaaa      60
tctcagtcct cactgagttc cgctattgag cgtctgtcct ctggtctgcg tatcaacagc     120
gcgaaagacg atgcggcagg ccaggcgatt gctaaccgct tcacttctaa tatcaaaggc     180
ctgactcagg cttcccgtaa cgctaacgac ggcatttcta ttgcgcagac cactgaaggt     240
gcgctgaatg aaatcaacaa caacctgcag cgtgtgcgtg agttgtctgt tcaggccact     300
aacgggacta actctgattc cgatctgaaa tctatccagg atgaaattca gcaacgtctg     360
gaagaaatcg atcgcgtttc taatcagact caatttaacg gtgttaaagt cctctctcag     420
gacaaccaga tgaaaatcca ggttggtgct aacgatggtg aaaccattac catcgatctg     480
caaaaaattg atgtgaaaag ccttggcctt gatgggttca atgttaatgg ccaaaagaa      540
gcgacagtgg gtgatctgaa atccagcttc aagaatgtta cgggttacga cacctatgca     600
gcgggtgccg ataaatatcg tgtagatatt aattccggtg ctgtagtgac tgatgcagca     660
gcaccggata agtatatgt aaatgcagca acggtcagt taacaactga cgatgcggaa      720
ataacactcg cggttgatct cttttaagacc actaaatcta ctgctggtac cgctgaagcc     780
aaagcgatag ctggtgccat taaaggtggt aaggaaggag atacctttga ttataaaggc     840
gtgacttttta ctattgatac aaaaactggt gatgacggta atggtaaggt ttctactacc     900
atcaatggtg aaaagttac gttaactgtc gctgatattg ccactggcgc ggcggatgtt     960
aatgctgcta ccttacaatc aagcaaaaat gtttatacat ctgtagtgaa cggtcagttt    1020
acttttgatg ataaaaccaa aaacgagagt gcgaaacttt ctgatttgga agcaaacaat    1080
gctgttaagg gcgaaagtaa aattacagta aatgggctg aatatactgc taacgccacg    1140
ggtgataaga tcaccttagc tgcaaaaacc atgtttattg ataaaacagc ttctggcgta    1200
agtacattaa tcaatgaaga cgctgccgca gccaagaaaa gtaccgctaa cccactggct    1260
tcaattgatt ctgcattgtc aaaagtggac gcagttcgtt cttctctggg ggcaattcaa    1320
aaccgttttg attcagccat taccaacctt ggcaatacgg taaccaatct gaactccgcg    1380
cgtagccgta tcgaagatgc tgactatgca acggaagttt ctaatatgtc taaagcgcag    1440
attctgcagc aggctggtac ttccgttctg gcgcaggcta accaggttcc gcaaaacgtc    1500
ctctcttac tgcgttaa                                                    1518
```

<210> SEQ ID NO 3
<211> LENGTH: 16
<212> TYPE: PRT
<213> ORGANISM: Artificial
<220> FEATURE:
<223> OTHER INFORMATION: peptide linker

<400> SEQUENCE: 3

Ser Pro Gly Ile Ser Gly Gly Gly Gly Ile Leu Asp Ser Met Gly
1               5                   10                  15

<210> SEQ ID NO 4
<211> LENGTH: 16
<212> TYPE: PRT
<213> ORGANISM: Artificial
<220> FEATURE:
<223> OTHER INFORMATION: peptide linker

<400> SEQUENCE: 4

Ile Pro Gly Ile Ser Gly Gly Gly Gly Gly Ile Leu Asp Ser Met Gly
1               5                   10                  15

<210> SEQ ID NO 5
<211> LENGTH: 46
<212> TYPE: DNA
<213> ORGANISM: Artificial
<220> FEATURE:
<223> OTHER INFORMATION: DNA coding sequence for peptide linker

<400> SEQUENCE: 5
tccccgggaa tttccggtgg tggtggtgga attctagact ccatgg    46

<210> SEQ ID NO 6
<211> LENGTH: 46
<212> TYPE: DNA
<213> ORGANISM: Artificial
<220> FEATURE:
<223> OTHER INFORMATION: DNA coding sequence for peptide linker

<400> SEQUENCE: 6
atcccgggaa tttccggtgg tggtggtgga attctagact ccatgg    46

<210> SEQ ID NO 7
<211> LENGTH: 990
<212> TYPE: DNA
<213> ORGANISM: Salmonella dublin

<400> SEQUENCE: 7
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtcgtcctc tggtctgcgt atcaacagcg cgaaagacga tgcggcaggc   240
caggcgattg ctaaccgctt cacttctaat atcaaaggcc tgactcaggc ttcccgtaac   300
gctaacgacg gcatttctat tgcgcagacc actgaaggtg cgctgaatga atcaacaac   360
aacctgcagc gtgtgcgtga gttgtctgtt caggccacta cgggactaa ctctgattcc   420
gatctgaaat ctatccagga tgaaattcag caacgtctgg aagaaatcga tcgcgtttct   480
aatcagactc aatttaacgg tgttaaagtc ctctctcagg acaaccagat gaaaatccag   540
gttggtgcta cgatggtga aaccattacc atcgatctgc aaaaaattga tgtgaaaagc   600
cttggccttg atgggttcaa tgttaattcc ccgggaattt ccggtggtgg tggtggaatt   660
ctagactcca tgggtacatt aatcaatgaa acgctgccg cagccaagaa aagtaccgct   720
aacccactgg cttcaattga ttctgcattg tcaaaagtgg acgcagttcg ttcttctctg   780
ggggcaattc aaaaccgttt tgattcagcc attaccaacc ttggcaatac ggtaaccaat   840
ctgaactccg cgcgtagccg tatcgaagat gctgactatg caacggaagt ttctaatatg   900
tctaaagcgc agattctgca gcaggctggt acttccgttc tggcgcaggc taaccaggtt   960
ccgcaaaacg tcctctcttt actgcgttag                                   990

<210> SEQ ID NO 8
<211> LENGTH: 329
<212> TYPE: PRT
<213> ORGANISM: Salmonella dublin

<400> SEQUENCE: 8

Met Arg Gly Ser His His His His His His Gly Met Ala Ser Met Thr
1               5                   10                  15

```
Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Gln Asn Arg Phe Asp Ser Ala Ile Thr
            260                 265                 270

Asn Leu Gly Asn Thr Val Thr Asn Leu Asn Ser Ala Arg Ser Arg Ile
        275                 280                 285

Glu Asp Ala Asp Tyr Ala Thr Glu Val Ser Asn Met Ser Lys Ala Gln
    290                 295                 300

Ile Leu Gln Gln Ala Gly Thr Ser Val Leu Ala Gln Ala Asn Gln Val
305                 310                 315                 320

Pro Gln Asn Val Leu Ser Leu Leu Arg
                325
```

<210> SEQ ID NO 9
<211> LENGTH: 825
<212> TYPE: DNA
<213> ORGANISM: Salmonella dublin

<400> SEQUENCE: 9

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggcc tgactcaggc ttcccgtaac   300
```

```
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagactc aatttaacgg tgttaaagtc ctctctcagg acaaccagat gaaaatccag    540
gttggtgcta acgatggtga accattacc atcgatctgc aaaaaattga tgtgaaaagc    600
cttggccttg atgggttcaa tgttaattcc ccgggaattt ccgtggtgg tggtggaattt    660 ctagactcca tgggtacatt aatcaatgaa gacgctgccg cagccaagaa aagtaccgct    720
aacccactgg cttcaattga ttctgcattg tcaaaagtgg acgcagttcg ttcttctctg    780
ggggcaattc aaaaccgttt tgattcagcc attaccaacc tttag                    825
```

<210> SEQ ID NO 10
<211> LENGTH: 274
<212> TYPE: PRT
<213> ORGANISM: Salmonella dublin

<400> SEQUENCE: 10

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Asn Gly Thr Asn Ser Asp Ser Asp Leu Lys Ser
130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Asp Gly Phe Asn Val
        195                 200                 205

Asn Ser Pro Gly Ile Ser Gly Gly Gly Gly Ile Leu Asp Ser Met
    210                 215                 220

Gly Thr Leu Ile Asn Glu Asp Ala Ala Ala Lys Lys Ser Thr Ala
225                 230                 235                 240

Asn Pro Leu Ala Ser Ile Asp Ser Ala Leu Ser Lys Val Asp Ala Val
                245                 250                 255

Arg Ser Ser Leu Gly Ala Ile Gln Asn Arg Phe Asp Ser Ala Ile Thr
            260                 265                 270

Asn Leu
```

<210> SEQ ID NO 11
<211> LENGTH: 831
<212> TYPE: DNA
<213> ORGANISM: Salmonella dublin

<400> SEQUENCE: 11

```
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta actctgattc cgatctgaaa tctatccagg atgaaattca gcaacgtctg     300
gaagaaatcg atcgcgtttc taatcagact caatttaacg gtgttaaagt cctctctcag     360
gacaaccaga tgaaaatcca ggttggtgct aacgatggtg aaaccattac catcgatctg     420
caaaaaattg atgtgaaaag ccttggcctt gatgggttca atgttaattc cccgggaatt     480
tccggtggtg gtggtggaat tctagactcc atgggtacat aatcaatga agacgctgcc     540
gcagccaaga aagtaccgc taacccactg gcttcaattg attctgcatt gtcaaaagtg     600
gacgcagttc gttcttctct ggggcaatt caaaaccgtt ttgattcagc cattaccaac     660
cttggcaata cggtaaccaa tctgaactcc gcgcgtagcc gtatcgaaga tgctgactat     720
gcaacggaag tttctaatat gtctaaagcg cagattctgc agcaggctgg tacttccgtt     780
ctggcgcagg ctaaccaggt tccgcaaaac gtcctctctt tactgcgtta g              831
```

<210> SEQ ID NO 12
<211> LENGTH: 276
<212> TYPE: PRT
<213> ORGANISM: Salmonella dublin

<400> SEQUENCE: 12

```
Met Arg Gly Ser His His His His His His Gly Met Ala Ser Met Thr
  1               5                  10                  15

Gly Gly Gln Gln Met Gly Arg Asp Leu Tyr Asp Asp Asp Lys Asp
             20                  25                  30

Pro Phe Thr Ser Asn Ile Lys Gly Leu Thr Gln Ala Ser Arg Asn Ala
         35                  40                  45

Asn Asp Gly Ile Ser Ile Ala Gln Thr Thr Glu Gly Ala Leu Asn Glu
     50                  55                  60

Ile Asn Asn Asn Leu Gln Arg Val Arg Glu Leu Ser Val Gln Ala Thr
 65                  70                  75                  80

Asn Gly Thr Asn Ser Asp Ser Asp Leu Lys Ser Ile Gln Asp Glu Ile
                 85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Asp Gly Phe Asn Val Asn Ser Pro Gly Ile
145                 150                 155                 160

Ser Gly Gly Gly Gly Ile Leu Asp Ser Met Gly Thr Leu Ile Asn
                165                 170                 175

Glu Asp Ala Ala Ala Ala Lys Lys Ser Thr Ala Asn Pro Leu Ala Ser
            180                 185                 190
```

```
Ile Asp Ser Ala Leu Ser Lys Val Asp Ala Val Arg Ser Ser Leu Gly
        195                 200                 205

Ala Ile Gln Asn Arg Phe Asp Ser Ala Ile Thr Asn Leu Gly Asn Thr
    210                 215                 220

Val Thr Asn Leu Asn Ser Ala Arg Ser Arg Ile Glu Asp Ala Asp Tyr
225                 230                 235                 240

Ala Thr Glu Val Ser Asn Met Ser Lys Ala Gln Ile Leu Gln Gln Ala
                245                 250                 255

Gly Thr Ser Val Leu Ala Gln Ala Asn Gln Val Pro Gln Asn Val Leu
            260                 265                 270

Ser Leu Leu Arg
        275

<210> SEQ ID NO 13
<211> LENGTH: 666
<212> TYPE: DNA
<213> ORGANISM: Salmonella dublin

<400> SEQUENCE: 13
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta actctgattc cgatctgaaa tctatccagg atgaaattca gcaacgtctg     300
gaagaaatcg atcgcgtttc taatcagact caatttaacg gtgttaaagt cctctctcag     360
gacaaccaga tgaaaatcca ggttggtgct aacgatggtg aaaccattac catcgatctg     420
caaaaaattg atgtgaaaag ccttggcctt gatgggttca atgttaattc cccgggaatt     480
tccggtggtg gtggtggaat tctagactcc atgggtacat taatcaatga agacgctgcc     540
gcagccaaga aaagtaccgc taacccactg gcttcaattg attctgcatt gtcaaaagtg     600
gacgcagttc gttcttctct gggggcaatt caaaaccgtt ttgattcagc cattaccaac     660
ctttag                                                                666

<210> SEQ ID NO 14
<211> LENGTH: 221
<212> TYPE: PRT
<213> ORGANISM: Salmonella dublin

<400> SEQUENCE: 14

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110
```

```
Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Asp Gly Phe Asn Val Asn Ser Pro Gly Ile
145                 150                 155                 160

Ser Gly Gly Gly Gly Ile Leu Asp Ser Met Gly Thr Leu Ile Asn
                165                 170                 175

Glu Asp Ala Ala Ala Lys Lys Ser Thr Ala Asn Pro Leu Ala Ser
            180                 185                 190

Ile Asp Ser Ala Leu Ser Lys Val Asp Ala Val Arg Ser Ser Leu Gly
        195                 200                 205

Ala Ile Gln Asn Arg Phe Asp Ser Ala Ile Thr Asn Leu
    210                 215                 220
```

<210> SEQ ID NO 15
<211> LENGTH: 603
<212> TYPE: DNA
<213> ORGANISM: Salmonella dublin

<400> SEQUENCE: 15

```
atgcggggtt ctcatcatca tcatcatcat ggtatggcta gcatgactgg tggacagcaa    60
atgggtcggg atctgtacga cgatgacgat aaggatccgt tcacttctaa tatcaaaggc   120
ctgactcagg cttcccgtaa cgctaacgac ggcatttcta ttgcgcagac cactgaaggt   180
gcgctgaatg aaatcaacaa caacctgcag cgtgtgcgtg agttgtctgt tcaggccact   240
tccccgggaa tttccggtgg tggtggtgga attctagact ccatgggtac attaatcaat   300
gaagacgctg ccgcagccaa gaaaagtacc gctaacccac tggcttcaat tgattctgca   360
ttgtcaaaag tggacgcagt tcgttcttct ctgggggcaa ttcaaaaccg ttttgattca   420
gccattacca accttggcaa tacggtaacc aatctgaact ccgcgcgtag ccgtatcgaa   480
gatgctgact atgcaacgga agtttctaat atgtctaaag cgcagattct gcagcaggct   540
ggtacttccg ttctggcgca ggctaaccag gttccgcaaa acgtcctctc tttactgcgt   600
tag                                                                 603
```

<210> SEQ ID NO 16
<211> LENGTH: 200
<212> TYPE: PRT
<213> ORGANISM: Salmonella dublin

<400> SEQUENCE: 16

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Ser Pro Gly Ile Ser Gly Gly Gly Gly Ile Leu Asp Ser Met Gly
            85                  90                  95

Thr Leu Ile Asn Glu Asp Ala Ala Ala Ala Lys Lys Ser Thr Ala Asn
```

```
                    100                 105                 110
Pro Leu Ala Ser Ile Asp Ser Ala Leu Ser Lys Val Asp Ala Val Arg
            115                 120                 125

Ser Ser Leu Gly Ala Ile Gln Asn Arg Phe Asp Ser Ala Ile Thr Asn
        130                 135                 140

Leu Gly Asn Thr Val Thr Asn Leu Asn Ser Ala Arg Ser Arg Ile Glu
145                 150                 155                 160

Asp Ala Asp Tyr Ala Thr Glu Val Ser Asn Met Ser Lys Ala Gln Ile
                165                 170                 175

Leu Gln Gln Ala Gly Thr Ser Val Leu Ala Gln Ala Asn Gln Val Pro
            180                 185                 190

Gln Asn Val Leu Ser Leu Leu Arg
            195                 200

<210> SEQ ID NO 17
<211> LENGTH: 438
<212> TYPE: DNA
<213> ORGANISM: Salmonella dublin

<400> SEQUENCE: 17
atgcggggtt ctcatcatca tcatcatcat ggtatggcta gcatgactgg tggacagcaa    60
atgggtcggg atctgtacga cgatgacgat aaggatccgt tcacttctaa tatcaaaggc   120
ctgactcagg cttcccgtaa cgctaacgac ggcatttcta ttgcgcagac cactgaaggt   180
gcgctgaatg aaatcaacaa caacctgcag cgtgtgcgtg agttgtctgt tcaggccact   240
tccccgggaa tttccggtgg tggtggtgga attctagact ccatgggtac attaatcaat   300
gaagacgctg ccgcagccaa gaaaagtacc gctaacccac tggcttcaat tgattctgca   360
ttgtcaaaag tggacgcagt tcgttcttct ctgggggcaa ttcaaaaccg ttttgattca   420
gccattacca acctttag                                                 438

<210> SEQ ID NO 18
<211> LENGTH: 145
<212> TYPE: PRT
<213> ORGANISM: Salmonella dublin

<400> SEQUENCE: 18

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Ser Pro Gly Ile Ser Gly Gly Gly Gly Ile Leu Asp Ser Met Gly
                85                  90                  95

Thr Leu Ile Asn Glu Asp Ala Ala Ala Ala Lys Lys Ser Thr Ala Asn
            100                 105                 110

Pro Leu Ala Ser Ile Asp Ser Ala Leu Ser Lys Val Asp Ala Val Arg
        115                 120                 125

Ser Ser Leu Gly Ala Ile Gln Asn Arg Phe Asp Ser Ala Ile Thr Asn
    130                 135                 140
```

Leu
145

<210> SEQ ID NO 19
<211> LENGTH: 639
<212> TYPE: DNA
<213> ORGANISM: Salmonella dublin

<400> SEQUENCE: 19

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggtc tgactcaggc ttcccgtaac   300
gctaacgacg gcatttctat tgcgcagacc actgaaggtg cgctgaatga aatcaacaac   360
aacctgcagc gtgtgcgtga gttgtctgtt caggccacta cgggactaa ctctgattcc   420
gatctgaaat ctatccagga tgaaattcag caacgtctgg aagaaatcga tcgcgtttct   480
aatcagactc aatttaacgg tgttaaagtc ctgtctcagg acaaccagat gaaaatccag   540
gttggtgcta acgatggtga accattacc atcgatctgc aaaaaattga tgtgaaaagc   600
cttggccttg atgggttcaa tgttaattcc ccgggatga                           639
```

<210> SEQ ID NO 20
<211> LENGTH: 212
<212> TYPE: PRT
<213> ORGANISM: Salmonella dublin

<400> SEQUENCE: 20

```
Met Arg Gly Ser His His His His His His Gly Met Ala Ser Met Thr
  1               5                  10                  15
Gly Gly Gln Gln Met Gly Arg Asp Leu Tyr Asp Asp Asp Lys Asp
             20                  25                  30
Pro Met Ala Gln Val Ile Asn Thr Asn Ser Leu Ser Leu Leu Thr Gln
         35                  40                  45
Asn Asn Leu Asn Lys Ser Gln Ser Ser Leu Ser Ser Ala Ile Glu Arg
     50                  55                  60
Leu Ser Ser Gly Leu Arg Ile Asn Ser Ala Lys Asp Asp Ala Ala Gly
 65                  70                  75                  80
Gln Ala Ile Ala Asn Arg Phe Thr Ser Asn Ile Lys Gly Leu Thr Gln
                 85                  90                  95
Ala Ser Arg Asn Ala Asn Asp Gly Ile Ser Ile Ala Gln Thr Thr Glu
            100                 105                 110
Gly Ala Leu Asn Glu Ile Asn Asn Asn Leu Gln Arg Val Arg Glu Leu
        115                 120                 125
Ser Val Gln Ala Thr Asn Gly Thr Asn Ser Asp Ser Asp Leu Lys Ser
    130                 135                 140
Ile Gln Asp Glu Ile Gln Gln Arg Leu Glu Glu Ile Asp Arg Val Ser
145                 150                 155                 160
Asn Gln Thr Gln Phe Asn Gly Val Lys Val Leu Ser Gln Asp Asn Gln
                165                 170                 175
Met Lys Ile Gln Val Gly Ala Asn Asp Gly Glu Thr Ile Thr Ile Asp
            180                 185                 190
Leu Gln Lys Ile Asp Val Lys Ser Leu Gly Leu Asp Gly Phe Asn Val
        195                 200                 205
```

Asn Ser Pro Gly
    210

<210> SEQ ID NO 21
<211> LENGTH: 480
<212> TYPE: DNA
<213> ORGANISM: Salmonella dublin

<400> SEQUENCE: 21

```
atgcggggtt ctcatcatca tcatcatcat ggtatggcta gcatgactgg tggacagcaa    60
atgggtcggg atctgtacga cgatgacgat aaggatccgt tcacttctaa tatcaaaggt   120
ctgactcagg cttcccgtaa cgctaacgac ggcatttcta ttgcgcagac cactgaaggt   180
gcgctgaatg aaatcaacaa caacctgcag cgtgtgcgtg agttgtctgt tcaggccact   240
aacgggacta actctgattc cgatctgaaa tctatccagg atgaaattca gcaacgtctg   300
gaagaaatcg atcgcgtttc taatcagact caatttaacg gtgttaaagt cctgtctcag   360
gacaaccaga tgaaaatcca ggttggtgct aacgatggtg aaaccattac catcgatctg   420
caaaaaattg atgtgaaaag ccttggcctt gatgggttca atgttaattc cccgggatga   480
```

<210> SEQ ID NO 22
<211> LENGTH: 159
<212> TYPE: PRT
<213> ORGANISM: Salmonella dublin

<400> SEQUENCE: 22

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Asp Gly Phe Asn Val Asn Ser Pro Gly
145                 150                 155

<210> SEQ ID NO 23
<211> LENGTH: 252
<212> TYPE: DNA
<213> ORGANISM: Salmonella dublin

<400> SEQUENCE: 23

```
atgcggggtt ctcatcatca tcatcatcat ggtatggcta gcatgactgg tggacagcaa    60
atgggtcggg atctgtacga cgatgacgat aaggatccgt tcacttctaa tatcaaaggt   120
ctgactcagg cttcccgtaa cgctaacgac ggcatttcta ttgcgcagac cactgaaggt   180
```

```
gcgctgaatg aaatcaacaa caacctgcag cgtgtgcgtg agttgtctgt tcaggccact    240
tccccgggat ga                                                        252

<210> SEQ ID NO 24
<211> LENGTH: 83
<212> TYPE: PRT
<213> ORGANISM: Salmonella dublin

<400> SEQUENCE: 24

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Ser Pro Gly

<210> SEQ ID NO 25
<211> LENGTH: 1038
<212> TYPE: DNA
<213> ORGANISM: Salmonella dublin

<400> SEQUENCE: 25
atgtccccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg ttgtcccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480 gttgtttat acatggaccc aatgtgcctg gatgcgttcc caaaattagt ttgttttaaa   540
aaacgtattg aagctatccc acaaattgat aagtacttga atccagcaa gtatatagca   600 tggcctttgc agggctggca agccacgttt ggtggtggcg accatcctcc aaaatcggat   660
ctggttccgc gtggatcccc gggaattccc ggtggtggtg gtggaattct agactccatg   720
ggtacattaa tcaatgaaga cgctgccgca gccaagaaaa gtaccgctaa cccactggct   780
tcaattgatt ctgcattgtc aaaagtggac gcagttcgtt cttctctggg ggcaattcaa   840
aaccgttttg attcagccat taccaacctt ggcaatacgg taaccaatct gaactccgcg   900
cgtagccgta tcgaagatgc tgactatgca acggaagttt ctaatatgtc taaagcgcag   960
attctgcagc aggctggtac ttccgttctg gcgcaggcta accaggttcc gcaaaacgtc  1020
ctctctttac tgcgttag                                                1038

<210> SEQ ID NO 26
<211> LENGTH: 345
<212> TYPE: PRT
<213> ORGANISM: Salmonella dublin
```

<400> SEQUENCE: 26

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Ser Gly Gly Gly Gly Ile Leu Asp Ser Met
225                 230                 235                 240

Gly Thr Leu Ile Asn Glu Asp Ala Ala Ala Lys Lys Ser Thr Ala
                245                 250                 255

Asn Pro Leu Ala Ser Ile Asp Ser Ala Leu Ser Lys Val Asp Ala Val
            260                 265                 270

Arg Ser Ser Leu Gly Ala Ile Gln Asn Arg Phe Asp Ser Ala Ile Thr
        275                 280                 285

Asn Leu Gly Asn Thr Val Thr Asn Leu Asn Ser Ala Arg Ser Arg Ile
    290                 295                 300

Glu Asp Ala Asp Tyr Ala Thr Glu Val Ser Asn Met Ser Lys Ala Gln
305                 310                 315                 320

Ile Leu Gln Gln Ala Gly Thr Ser Val Leu Gln Ala Asn Gln Val
                325                 330                 335

Pro Gln Asn Val Leu Ser Leu Leu Arg
            340                 345
```

<210> SEQ ID NO 27
<211> LENGTH: 873
<212> TYPE: DNA
<213> ORGANISM: Salmonella dublin

<400> SEQUENCE: 27
atgtccccta tactaggtta ttggaaaatt aagggccttg tgcaacccac tcgacttctt    60

```
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa     540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatcccc gggaatttcc ggtggtggtg gtggaattct agactccatg    720
ggtacattaa tcaatgaaga cgctgccgca gccaagaaaa gtaccgctaa cccactggct    780
tcaattgatt ctgcattgtc aaaagtggac gcagttcgtt cttctctggg ggcaattcaa    840
aaccgttttg attcagccat taccaacctt tag                                 873

<210> SEQ ID NO 28
<211> LENGTH: 290
<212> TYPE: PRT
<213> ORGANISM: Salmonella dublin

<400> SEQUENCE: 28

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Ser Gly Gly Gly Gly Gly Ile Leu Asp Ser Met
```

```
                225                 230                 235                 240
Gly Thr Leu Ile Asn Glu Asp Ala Ala Ala Lys Lys Ser Thr Ala
                    245                 250                 255

Asn Pro Leu Ala Ser Ile Asp Ser Ala Leu Ser Lys Val Asp Ala Val
                260                 265                 270

Arg Ser Ser Leu Gly Ala Ile Gln Asn Arg Phe Asp Ser Ala Ile Thr
            275                 280                 285

Asn Leu
    290

<210> SEQ ID NO 29
<211> LENGTH: 972
<212> TYPE: DNA
<213> ORGANISM: Salmonella dublin

<400> SEQUENCE: 29
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtcgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga atcaacaac     360 aacctgcagc gtgtgcgtga gttgtctgtt caggccacta cgggactaa ctctgattcc     420 gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta acgatggtga aaccattacc atcgatctgc aaaaaattga tgtgaaaagc     600
cttggcctta tcccgggaat tccggtggt ggtggtggaa ttctagactc catgggtaca     660
ttaatcaatg aagacgctgc cgcagccaag aaaagtaccg ctaacccact ggcttcaatt     720
gattctgcat tgtcaaaagt ggacgcagtt cgttcttctc tggggggcaat tcaaaaccgt     780 tttgattcag ccattaccaa ccttggcaat acggtaacca atctgaactc cgcgcgtagc     840
cgtatcgaag atgctgacta tgcaacggaa gtttctaata tgtctaaagc gcagattctg     900
cagcaggctg gtacttccgt tctggcgcag gctaaccagg ttccgcaaaa cgtcctctct     960
ttactgcgtt ag                                                          972

<210> SEQ ID NO 30
<211> LENGTH: 323
<212> TYPE: PRT
<213> ORGANISM: Salmonella dublin

<400> SEQUENCE: 30

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80
```

```
Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Leu Gln Arg Val Arg Glu Leu
        115                 120                 125

Ser Val Gln Ala Thr Asn Gly Thr Asn Ser Asp Ser Asp Leu Lys Ser
130                 135                 140

Ile Gln Asp Glu Ile Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Ile Pro Gly Ile Ser
        195                 200                 205

Gly Gly Gly Gly Ile Leu Asp Ser Met Gly Thr Leu Ile Asn Glu
210                 215                 220

Asp Ala Ala Ala Lys Lys Ser Thr Ala Asn Pro Leu Ala Ser Ile
225                 230                 235                 240

Asp Ser Ala Leu Ser Lys Val Asp Ala Val Arg Ser Ser Leu Gly Ala
                245                 250                 255

Ile Gln Asn Arg Phe Asp Ser Ala Ile Thr Asn Leu Gly Asn Thr Val
            260                 265                 270

Thr Asn Leu Asn Ser Ala Arg Ser Arg Ile Glu Asp Ala Asp Tyr Ala
        275                 280                 285

Thr Glu Val Ser Asn Met Ser Lys Ala Gln Ile Leu Gln Gln Ala Gly
290                 295                 300

Thr Ser Val Leu Ala Gln Ala Asn Gln Val Pro Gln Asn Val Leu Ser
305                 310                 315                 320

Leu Leu Arg

<210> SEQ ID NO 31
<211> LENGTH: 813
<212> TYPE: DNA
<213> ORGANISM: Salmonella dublin

<400> SEQUENCE: 31
atgcggggtt ctcatcatca tcatcatcat ggtatggcta gcatgactgg tggacagcaa     60
atgggtcggg atctgtacga cgatgacgat aaggatccgt tcacttctaa tatcaaaggc    120
ctgactcagg cttcccgtaa cgctaacgac ggcatttcta ttgcgcagac cactgaaggt    180
gcgctgaatg aaatcaacaa caacctgcag cgtgtgcgtg agttgtctgt tcaggccact    240
aacgggacta actctgattc cgatctgaaa tctatccagg atgaaattca gcaacgtctg    300
gaagaaatcg atcgcgtttc taatcagact caatttaacg gtgttaaagt cctctctcag    360
gacaaccaga tgaaaatcca ggttggtgct aacgatggtg aaaccattac catcgatctg    420
caaaaaattg atgtgaaaag ccttggcctt atcccgggaa tttccggtgg tggtggtgga    480
attctagact ccatgggtac attaatcaat gaagacgctg ccgcagccaa gaaaagtacc    540
gctaacccac tggcttcaat tgattctgca ttgtcaaaag tggacgcagt tcgttcttct    600 ctggggggcaa ttcaaaaccg ttttgattca gccattacca accttggcaa tacggtaacc    660
aatctgaact ccgcgcgtag ccgtatcgaa gatgctgact atgcaacgga agtttctaat    720
```
atgtctaaag cgcagattct gcagcaggct ggtacttccg ttctggcgca ggctaaccag    780
gttccgcaaa acgtcctctc tttactgcgt tag                                 813

<210> SEQ ID NO 32
<211> LENGTH: 270
<212> TYPE: PRT
<213> ORGANISM: Salmonella dublin

<400> SEQUENCE: 32

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
        115                 120                 125

Gly Ala Asn Asp Gly Glu Thr Ile Thr Ile Asp Leu Gln Lys Ile Asp
    130                 135                 140

Val Lys Ser Leu Gly Leu Ile Pro Gly Ile Ser Gly Gly Gly Gly
145                 150                 155                 160

Ile Leu Asp Ser Met Gly Thr Leu Ile Asn Glu Asp Ala Ala Ala Ala
                165                 170                 175

Lys Lys Ser Thr Ala Asn Pro Leu Ala Ser Ile Asp Ser Ala Leu Ser
            180                 185                 190

Lys Val Asp Ala Val Arg Ser Ser Leu Gly Ala Ile Gln Asn Arg Phe
        195                 200                 205

Asp Ser Ala Ile Thr Asn Leu Gly Asn Thr Val Thr Asn Leu Asn Ser
    210                 215                 220

Ala Arg Ser Arg Ile Glu Asp Ala Asp Tyr Ala Thr Glu Val Ser Asn
225                 230                 235                 240

Met Ser Lys Ala Gln Ile Leu Gln Gln Ala Gly Thr Ser Val Leu Ala
                245                 250                 255

Gln Ala Asn Gln Val Pro Gln Asn Val Leu Ser Leu Leu Arg
            260                 265                 270

<210> SEQ ID NO 33
<211> LENGTH: 951
<212> TYPE: DNA
<213> ORGANISM: Salmonella dublin

<400> SEQUENCE: 33
atgcggggtt ctcatcatca tcatcatcat ggtatggcta gcatgactgg tggacagcaa     60
atgggtcggg atctgtacga cgatgacgat aaggatccga tggcacaagt cattaataca    120
aacagcctgt cgctgttgac ccagaataac ctgaacaaat ctcagtcctc actgagttcc    180
gctattgagc gtctgtcctc tggtctgcgt atcaacagcg cgaaagacga tgcggcaggc    240

```
caggcgattg ctaaccgctt cacttctaat atcaaaggcc tgactcaggc ttcccgtaac    300
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagactc aatttaacgg tgttaaagtc ctctctcagg acaaccagat gaaaatccag    540
gttggtgcta acgatggtga aaccattacc atcgatctgc aaaaaattat cccgggaatt    600
tccggtggtg gtggtggaat tctagactcc atgggtacat taatcaatga agacgctgcc    660
gcagccaaga aaagtaccgc taacccactg gcttcaattg attctgcatt gtcaaaagtg    720
gacgcagttc gttcttctct gggggcaatt caaaaccgtt ttgattcagc cattaccaac    780
cttggcaata cggtaaccaa tctgaactcc gcgcgtagcc gtatcgaaga tgctgactat    840
gcaacggaag tttctaatat gtctaaagcg cagattctgc agcaggctgg tacttccgtt    900
ctggcgcagg ctaaccaggt tccgcaaaac gtcctctctt tactgcgtta g             951

<210> SEQ ID NO 34
<211> LENGTH: 316
<212> TYPE: PRT
<213> ORGANISM: Salmonella dublin

<400> SEQUENCE: 34

Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
        50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Ile Pro Gly Ile Ser Gly Gly Gly Gly Ile Leu
        195                 200                 205

Asp Ser Met Gly Thr Leu Ile Asn Glu Asp Ala Ala Ala Ala Lys Lys
    210                 215                 220

Ser Thr Ala Asn Pro Leu Ala Ser Ile Asp Ser Ala Leu Ser Lys Val
225                 230                 235                 240

Asp Ala Val Arg Ser Ser Leu Gly Ala Ile Gln Asn Arg Phe Asp Ser
                245                 250                 255
```

```
Ala Ile Thr Asn Leu Gly Asn Thr Val Thr Asn Leu Asn Ser Ala Arg
            260                 265                 270

Ser Arg Ile Glu Asp Ala Asp Tyr Ala Thr Glu Val Ser Asn Met Ser
        275                 280                 285

Lys Ala Gln Ile Leu Gln Gln Ala Gly Thr Ser Val Leu Ala Gln Ala
    290                 295                 300

Asn Gln Val Pro Gln Asn Val Leu Ser Leu Leu Arg
305                 310                 315

<210> SEQ ID NO 35
<211> LENGTH: 792
<212> TYPE: DNA
<213> ORGANISM: Salmonella dublin

<400> SEQUENCE: 35
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta actctgattc cgatctgaaa tctatccagg atgaaattca gcaacgtctg     300
gaagaaatcg atcgcgtttc taatcagact caatttaacg gtgttaaagt cctctctcag     360
gacaaccaga tgaaaatcca ggttggtgct aacgatggtg aaaccattac catcgatctg     420
caaaaaatta tcccgggaat ttccggtggt ggtggtggaa ttctagactc catgggtaca     480
ttaatcaatg aagacgctgc cgcagccaag aaaagtaccg ctaacccact ggcttcaatt     540
gattctgcat tgtcaaaagt ggacgcagtt cgttcttctc tgggggcaat tcaaaaccgt     600
tttgattcag ccattaccaa ccttggcaat acggtaacca atctgaactc cgcgcgtagc     660
cgtatcgaag atgctgacta tgcaacggaa gtttctaata tgtctaaagc gcagattctg     720
cagcaggctg gtacttccgt tctggcgcag gctaaccagg ttccgcaaaa cgtcctctct     780
ttactgcgtt ag                                                         792

<210> SEQ ID NO 36
<211> LENGTH: 263
<212> TYPE: PRT
<213> ORGANISM: Salmonella dublin

<400> SEQUENCE: 36

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Thr Gln Phe
            100                 105                 110

Asn Gly Val Lys Val Leu Ser Gln Asp Asn Gln Met Lys Ile Gln Val
```

```
              115                 120                 125
Gly Ala Asn Asp Gly Glu Thr Ile Thr Ile Asp Leu Gln Lys Ile Ile
        130                 135                 140

Pro Gly Ile Ser Gly Gly Gly Gly Ile Leu Asp Ser Met Gly Thr
145                 150                 155                 160

Leu Ile Asn Glu Asp Ala Ala Ala Lys Lys Ser Thr Ala Asn Pro
            165                 170                 175

Leu Ala Ser Ile Asp Ser Ala Leu Ser Lys Val Asp Ala Val Arg Ser
            180                 185                 190

Ser Leu Gly Ala Ile Gln Asn Arg Phe Asp Ser Ala Ile Thr Asn Leu
            195                 200                 205

Gly Asn Thr Val Thr Asn Leu Asn Ser Ala Arg Ser Arg Ile Glu Asp
        210                 215                 220

Ala Asp Tyr Ala Thr Glu Val Ser Asn Met Ser Lys Ala Gln Ile Leu
225                 230                 235                 240

Gln Gln Ala Gly Thr Ser Val Leu Ala Gln Ala Asn Gln Val Pro Gln
            245                 250                 255

Asn Val Leu Ser Leu Leu Arg
            260
```

<210> SEQ ID NO 37
<211> LENGTH: 807
<212> TYPE: DNA
<213> ORGANISM: Salmonella dublin

<400> SEQUENCE: 37

```
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggcc tgactcaggc ttcccgtaac   300
gctaacgacg gcatttctat tgcgcagacc actgaaggtg cgctgaatga atcaacaac   360
aacctgcagc gtgtgcgtga tgtctgtt caggccacta cgggactaa ctctgattcc     420
gatctgaaat ctatccagga tgaaattcag caacgtctgg aagaaatcga tcgcgtttct   480
aatcagactc aatttaacgg tgttaaagtc ctctctcagg acaaccagat gaaaatccag   540
gttggtgcta cgatggtga aaccattacc atcgatctgc aaaaaattga tgtgaaaagc   600
cttggcctta tcccgggaat ttccggtggt ggtggtggaa ttctagactc catgggtaca   660
ttaatcaatg aagacgctgc cgcagccaag aaaagtaccg ctaacccact ggcttcaatt   720
gattctgcat tgtcaaaagt ggacgcagtt cgttcttctc tgggggcaat tcaaaaccgt   780
tttgattcag ccattaccaa cctttag                                       807
```

<210> SEQ ID NO 38
<211> LENGTH: 268
<212> TYPE: PRT
<213> ORGANISM: Salmonella dublin

<400> SEQUENCE: 38

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30
```

Pro Met Ala Gln Val Ile Asn Thr Asn Ser Leu Ser Leu Leu Thr Gln
            35                  40                  45

Asn Asn Leu Asn Lys Ser Gln Ser Ser Leu Ser Ser Ala Ile Glu Arg
 50                  55                  60

Leu Ser Ser Gly Leu Arg Ile Asn Ser Ala Lys Asp Asp Ala Ala Gly
 65                  70                  75                  80

Gln Ala Ile Ala Asn Arg Phe Thr Ser Asn Ile Lys Gly Leu Thr Gln
                 85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
            115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Asp Val Lys Ser Leu Gly Leu Ile Pro Gly Ile Ser
            195                 200                 205

Gly Gly Gly Gly Gly Ile Leu Asp Ser Met Gly Thr Leu Ile Asn Glu
    210                 215                 220

Asp Ala Ala Ala Lys Lys Ser Thr Ala Asn Pro Leu Ala Ser Ile
225                 230                 235                 240

Asp Ser Ala Leu Ser Lys Val Asp Ala Val Arg Ser Ser Leu Gly Ala
                245                 250                 255

Ile Gln Asn Arg Phe Asp Ser Ala Ile Thr Asn Leu
            260                 265

<210> SEQ ID NO 39
<211> LENGTH: 786
<212> TYPE: DNA
<213> ORGANISM: Salmonella dublin

<400> SEQUENCE: 39
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga aatcaacaac     360
aacctgcagc gtgtgcgtga gttgtctgtt caggccacta acgggactaa ctctgattcc     420
gatctgaaat ctatccagga tgaaattcag caacgtctgg aagaaatcga tcgcgtttct     480
aatcagactc aatttaacgg tgttaaagtc ctctctcagg acaaccagat gaaaatccag     540
gttggtgcta acgatggtga aaccattacc atcgatctgc aaaaaattat cccgggaatt     600
tccggtggtg gtggtggaat tctagactcc atgggtacat taatcaatga agacgctgcc     660
gcagccaaga aaagtaccgc taacccactg gcttcaattg attctgcatt gtcaaaagtg     720
gacgcagttc gttcttctct ggggggcaatt caaaaccgtt ttgattcagc cattaccaac     780

```
ctttag                                                           786

<210> SEQ ID NO 40
<211> LENGTH: 261
<212> TYPE: PRT
<213> ORGANISM: Salmonella dublin

<400> SEQUENCE: 40

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Thr Gln Phe Asn Gly Val Lys Val Leu Ser Gln Asp Asn Gln
                165                 170                 175

Met Lys Ile Gln Val Gly Ala Asn Asp Gly Glu Thr Ile Thr Ile Asp
            180                 185                 190

Leu Gln Lys Ile Ile Pro Gly Ile Ser Gly Gly Gly Gly Ile Leu
        195                 200                 205

Asp Ser Met Gly Thr Leu Ile Asn Glu Asp Ala Ala Ala Lys Lys
    210                 215                 220

Ser Thr Ala Asn Pro Leu Ala Ser Ile Asp Ser Ala Leu Ser Lys Val
225                 230                 235                 240

Asp Ala Val Arg Ser Ser Leu Gly Ala Ile Gln Asn Arg Phe Asp Ser
                245                 250                 255

Ala Ile Thr Asn Leu
            260

<210> SEQ ID NO 41
<211> LENGTH: 849
<212> TYPE: DNA
<213> ORGANISM: Salmonella dublin

<400> SEQUENCE: 41
atgcggggtt ctcatcatca tcatcatcat ggtatggcta gcatgactgg tggacagcaa    60
atgggtcggg atctgtacga cgatgacgat aaggatccga tggcacaagt cattaataca   120
aacagcctgt cgctgttgac ccagaataac ctgaacaaat ctcagtcctc actgagttcc   180
gctattgagc gtctgtcctc tggtctgcgt atcaacagcg cgaaagacga tgcggcaggc   240
caggcgattg ctaaccgctt cacttctaat atcaaaggcc tgactcaggc ttcccgtaac   300
```

```
gctaacgacg gcatttctat tgcgcagacc actgaaggtg cgctgaatga aatcaacaac    360
aacctgcagc gtgtgcgtga gttgtctgtt caggccacta acgggactaa ctctgattcc    420
gatctgaaat ctatccagga tgaaattcag caacgtctgg aagaaatcga tcgcgtttct    480
aatcagatcc cgggaattt c cggtggtggt ggtggaattc tagactccat gggtacatta    540
atcaatgaag acgctgccgc agccaagaaa agtaccgcta acccactggc ttcaattgat    600
tctgcattgt caaaagtgga cgcagttcgt tcttctctgg gggcaattca aaaccgtttt    660
gattcagcca ttaccaacct tggcaatacg gtaaccaatc tgaactccgc gcgtagccgt    720
atcgaagatg ctgactatgc aacggaagtt tctaatatgt ctaaagcgca gattctgcag    780
caggctggta cttccgttct ggcgcaggct aaccaggttc gcaaaaacgt cctctcttta    840
ctgcgttag                                                            849
```

<210> SEQ ID NO 42
<211> LENGTH: 282
<212> TYPE: PRT
<213> ORGANISM: Salmonella dublin

<400> SEQUENCE: 42

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Ile Pro Gly Ile Ser Gly Gly Gly Gly Ile Leu Asp Ser
                165                 170                 175

Met Gly Thr Leu Ile Asn Glu Asp Ala Ala Ala Ala Lys Lys Ser Thr
            180                 185                 190

Ala Asn Pro Leu Ala Ser Ile Asp Ser Ala Leu Ser Lys Val Asp Ala
        195                 200                 205

Val Arg Ser Ser Leu Gly Ala Ile Gln Asn Arg Phe Asp Ser Ala Ile
    210                 215                 220

Thr Asn Leu Gly Asn Thr Val Thr Asn Leu Asn Ser Ala Arg Ser Arg
225                 230                 235                 240

Ile Glu Asp Ala Asp Tyr Ala Thr Glu Val Ser Asn Met Ser Lys Ala
                245                 250                 255

Gln Ile Leu Gln Gln Ala Gly Thr Ser Val Leu Ala Gln Ala Asn Gln
            260                 265                 270
```

Val Pro Gln Asn Val Leu Ser Leu Leu Arg
            275                 280

<210> SEQ ID NO 43
<211> LENGTH: 690
<212> TYPE: DNA
<213> ORGANISM: Salmonella dublin

<400> SEQUENCE: 43
atgcggggtt ctcatcatca tcatcatcat ggtatggcta gcatgactgg tggacagcaa     60
atgggtcggg atctgtacga cgatgacgat aaggatccgt tcacttctaa tatcaaaggc    120
ctgactcagg cttcccgtaa cgctaacgac ggcatttcta ttgcgcagac cactgaaggt    180
gcgctgaatg aaatcaacaa caacctgcag cgtgtgcgtg agttgtctgt tcaggccact    240
aacgggacta actctgattc cgatctgaaa tctatccagg atgaaattca gcaacgtctg    300
gaagaaatcg atcgcgtttc taatcagatc ccgggaattt ccggtggtgg tggtggaatt    360
ctagactcca tgggtacatt aatcaatgaa gacgctgccg cagccaagaa aagtaccgct    420
aacccactgg cttcaattga ttctgcattg tcaaaagtgg acgcagttcg ttcttctctg    480
ggggcaattc aaaaccgttt tgattcagcc attaccaacc ttggcaatac ggtaaccaat    540
ctgaactccg cgcgtagccg tatcgaagat gctgactatg caacggaagt ttctaatatg    600
tctaaagcgc agattctgca gcaggctggt acttccgttc tggcgcaggc taaccaggtt    660
ccgcaaaacg tcctctcttt actgcgttag                                     690

<210> SEQ ID NO 44
<211> LENGTH: 229
<212> TYPE: PRT
<213> ORGANISM: Salmonella dublin

<400> SEQUENCE: 44

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Ile Pro Gly
            100                 105                 110

Ile Ser Gly Gly Gly Gly Gly Ile Leu Asp Ser Met Gly Thr Leu Ile
        115                 120                 125

Asn Glu Asp Ala Ala Ala Ala Lys Lys Ser Thr Ala Asn Pro Leu Ala
    130                 135                 140

Ser Ile Asp Ser Ala Leu Ser Lys Val Asp Ala Val Arg Ser Ser Leu
145                 150                 155                 160

Gly Ala Ile Gln Asn Arg Phe Asp Ser Ala Ile Thr Asn Leu Gly Asn
                165                 170                 175

Thr Val Thr Asn Leu Asn Ser Ala Arg Ser Arg Ile Glu Asp Ala Asp
            180                 185                 190

Tyr Ala Thr Glu Val Ser Asn Met Ser Lys Ala Gln Ile Leu Gln Gln
            195                 200                 205

Ala Gly Thr Ser Val Leu Ala Gln Ala Asn Gln Val Pro Gln Asn Val
        210                 215                 220

Leu Ser Leu Leu Arg
225

<210> SEQ ID NO 45
<211> LENGTH: 684
<212> TYPE: DNA
<213> ORGANISM: Salmonella dublin

<400> SEQUENCE: 45

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga atcaacaac      360
aacctgcagc gtgtgcgtga gttgtctgtt caggccacta cgggactaa ctctgattcc      420
gatctgaaat ctatccagga tgaaattcag caacgtctgg aagaaatcga tcgcgtttct     480
aatcagatcc cggaatttc cggtggtggt ggtggaattc tagactccat gggtacatta      540
atcaatgaag acgctgccgc agccaagaaa agtaccgcta acccactggc ttcaattgat     600
tctgcattgt caaaagtgga cgcagttcgt tcttctctgg gggcaattca aaaccgtttt     660
gattcagcca ttaccaacct ttag                                             684
```

<210> SEQ ID NO 46
<211> LENGTH: 227
<212> TYPE: PRT
<213> ORGANISM: Salmonella dublin

<400> SEQUENCE: 46

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Asn Gly Thr Asn Ser Asp Ser Asp Leu Lys Ser
    130                 135                 140

Ile Gln Asp Glu Ile Gln Gln Arg Leu Glu Glu Ile Asp Arg Val Ser
145                 150                 155                 160

Asn Gln Ile Pro Gly Ile Ser Gly Gly Gly Gly Ile Leu Asp Ser
            165                 170                 175

Met Gly Thr Leu Ile Asn Glu Asp Ala Ala Ala Lys Lys Ser Thr
        180                 185                 190

Ala Asn Pro Leu Ala Ser Ile Asp Ser Ala Leu Ser Lys Val Asp Ala
        195                 200                 205

Val Arg Ser Ser Leu Gly Ala Ile Gln Asn Arg Phe Asp Ser Ala Ile
    210                 215                 220

Thr Asn Leu
225

<210> SEQ ID NO 47
<211> LENGTH: 525
<212> TYPE: DNA
<213> ORGANISM: Salmonella dublin

<400> SEQUENCE: 47

```
atgcggggtt ctcatcatca tcatcatcat ggtatggcta gcatgactgg tggacagcaa      60
atgggtcggg atctgtacga cgatgacgat aaggatccgt tcacttctaa tatcaaaggc     120
ctgactcagg cttcccgtaa cgctaacgac ggcatttcta ttgcgcagac cactgaaggt     180
gcgctgaatg aaatcaacaa caacctgcag cgtgtgcgtg agttgtctgt tcaggccact     240
aacgggacta actctgattc cgatctgaaa tctatccagg atgaaattca gcaacgtctg     300
gaagaaatcg atcgcgtttc taatcagatc ccgggaattt ccggtggtgg tggtggaatt     360
ctagactcca tgggtacatt aatcaatgaa gacgctgccg cagccaagaa aagtaccgct     420
aacccactgg cttcaattga ttctgcattg tcaaaagtgg acgcagttcg ttcttctctg     480
ggggcaattc aaaaccgttt tgattcagcc attaccaacc tttag                     525
```

<210> SEQ ID NO 48
<211> LENGTH: 174
<212> TYPE: PRT
<213> ORGANISM: Salmonella dublin

<400> SEQUENCE: 48

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Phe Thr Ser Asn Ile Lys Gly Leu Thr Gln Ala Ser Arg Asn Ala
        35                  40                  45

Asn Asp Gly Ile Ser Ile Ala Gln Thr Thr Glu Gly Ala Leu Asn Glu
    50                  55                  60

Ile Asn Asn Asn Leu Gln Arg Val Arg Glu Leu Ser Val Gln Ala Thr
65                  70                  75                  80

Asn Gly Thr Asn Ser Asp Ser Asp Leu Lys Ser Ile Gln Asp Glu Ile
                85                  90                  95

Gln Gln Arg Leu Glu Glu Ile Asp Arg Val Ser Asn Gln Ile Pro Gly
            100                 105                 110

Ile Ser Gly Gly Gly Gly Gly Ile Leu Asp Ser Met Gly Thr Leu Ile
        115                 120                 125

Asn Glu Asp Ala Ala Ala Ala Lys Lys Ser Thr Ala Asn Pro Leu Ala
    130                 135                 140

Ser Ile Asp Ser Ala Leu Ser Lys Val Asp Ala Val Arg Ser Ser Leu
145                 150                 155                 160

Gly Ala Ile Gln Asn Arg Phe Asp Ser Ala Ile Thr Asn Leu
            165                 170

<210> SEQ ID NO 49
<211> LENGTH: 762
<212> TYPE: DNA
<213> ORGANISM: Salmonella dublin

<400> SEQUENCE: 49

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgacg gcatttctat tgcgcagacc actgaaggtg cgctgaatga aatcaacaac     360
aacctgcagc gtgtgcgtga gttgtctgtt caggccacta tcccgggaat ttccggtggt     420
ggtggtggaa ttctagactc catgggtaca ttaatcaatg aagacgctgc cgcagccaag     480
aaaagtaccg ctaacccact ggcttcaatt gattctgcat tgtcaaaagt ggacgcagtt     540
cgttcttctc tggggcaat tcaaaaccgt tttgattcag ccattaccaa ccttggcaat     600
acggtaacca atctgaactc cgcgcgtagc cgtatcgaag atgctgacta tgcaacggaa     660
gtttctaata tgtctaaagc gcagattctg cagcaggctg gtacttccgt tctggcgcag     720
gctaaccagg ttccgcaaaa cgtcctctct ttactgcgtt ag                        762
```

<210> SEQ ID NO 50
<211> LENGTH: 253
<212> TYPE: PRT
<213> ORGANISM: Salmonella dublin

<400> SEQUENCE: 50

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Ile Pro Gly Ile Ser Gly Gly Gly Gly Ile
    130                 135                 140

Leu Asp Ser Met Gly Thr Leu Ile Asn Glu Asp Ala Ala Ala Ala Lys
145                 150                 155                 160

Lys Ser Thr Ala Asn Pro Leu Ala Ser Ile Asp Ser Ala Leu Ser Lys
                165                 170                 175

Val Asp Ala Val Arg Ser Ser Leu Gly Ala Ile Gln Asn Arg Phe Asp

```
                180                 185                 190
Ser Ala Ile Thr Asn Leu Gly Asn Thr Val Thr Asn Leu Asn Ser Ala
            195                 200                 205

Arg Ser Arg Ile Glu Asp Ala Asp Tyr Ala Thr Glu Val Ser Asn Met
        210                 215                 220

Ser Lys Ala Gln Ile Leu Gln Gln Ala Gly Thr Ser Val Leu Ala Gln
225                 230                 235                 240

Ala Asn Gln Val Pro Gln Asn Val Leu Ser Leu Leu Arg
                245                 250

<210> SEQ ID NO 51
<211> LENGTH: 597
<212> TYPE: DNA
<213> ORGANISM: Salmonella dublin

<400> SEQUENCE: 51
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtcgtcctc tggtctgcgt atcaacagcg cgaaagacga tgcggcaggc     240
caggcgattg ctaaccgctt cacttctaat atcaaaggcc tgactcaggc ttcccgtaac    300
gctaacgacg gcatttctat tgcgcagacc actgaaggtg cgctgaatga atcaacaac     360 aacctgcagc gtgtgcgtga gttgtctgtt caggccacta tcccgggaat tccggtggt     420 ggtggtggaa ttctagactc catgggtaca ttaatcaatg aagacgctgc cgcagccaag    480
aaaagtaccg ctaacccact ggcttcaatt gattctgcat tgtcaaaagt ggacgcagtt    540
cgttcttctc tgggggcaat tcaaaaccgt tttgattcag ccattaccaa cctttag       597

<210> SEQ ID NO 52
<211> LENGTH: 198
<212> TYPE: PRT
<213> ORGANISM: Salmonella dublin

<400> SEQUENCE: 52

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Gly Ile Ser Ile Ala Gln Thr Thr Glu
            100                 105                 110

Gly Ala Leu Asn Glu Ile Asn Asn Asn Leu Gln Arg Val Arg Glu Leu
        115                 120                 125

Ser Val Gln Ala Thr Ile Pro Gly Ile Ser Gly Gly Gly Gly Ile
    130                 135                 140

Leu Asp Ser Met Gly Thr Leu Ile Asn Glu Asp Ala Ala Ala Ala Lys
145                 150                 155                 160
```

Lys Ser Thr Ala Asn Pro Leu Ala Ser Ile Asp Ser Ala Leu Ser Lys
                165                 170                 175

Val Asp Ala Val Arg Ser Ser Leu Gly Ala Ile Gln Asn Arg Phe Asp
            180                 185                 190

Ser Ala Ile Thr Asn Leu
        195

<210> SEQ ID NO 53
<211> LENGTH: 672
<212> TYPE: DNA
<213> ORGANISM: Salmonella dublin

<400> SEQUENCE: 53

```
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgaca tcccgggaat tccggtggt ggtggtggaa tcctagactc catgggtaca      360
ttaatcaatg aagacgctgc cgcagccaag aaaagtaccg ctaacccact ggcttcaatt     420
gattctgcat tgtcaaaagt ggacgcagtt cgttcttctc tggggcaat tcaaaaccgt      480
tttgattcag ccattaccaa ccttggcaat acggtaacca atctgaactc cgcgcgtagc     540
cgtatcgaag atgctgacta tgcaacggaa gtttctaata tgtctaaagc gcagattctg     600
cagcaggctg gtacttccgt tctggcgcag gctaaccagg ttccgcaaaa cgtcctctct     660
ttactgcgtt ag                                                         672
```

<210> SEQ ID NO 54
<211> LENGTH: 223
<212> TYPE: PRT
<213> ORGANISM: Salmonella dublin

<400> SEQUENCE: 54

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Ile Pro Gly Ile Ser Gly Gly Gly Gly
            100                 105                 110

Gly Ile Leu Asp Ser Met Gly Thr Leu Ile Asn Glu Asp Ala Ala Ala
        115                 120                 125

Ala Lys Lys Ser Thr Ala Asn Pro Leu Ala Ser Ile Asp Ser Ala Leu
    130                 135                 140

Ser Lys Val Asp Ala Val Arg Ser Ser Leu Gly Ala Ile Gln Asn Arg
145                 150                 155                 160

```
Phe Asp Ser Ala Ile Thr Asn Leu Gly Asn Thr Val Thr Asn Leu Asn
                165                 170                 175

Ser Ala Arg Ser Arg Ile Glu Asp Ala Asp Tyr Ala Thr Glu Val Ser
            180                 185                 190

Asn Met Ser Lys Ala Gln Ile Leu Gln Gln Ala Gly Thr Ser Val Leu
        195                 200                 205

Ala Gln Ala Asn Gln Val Pro Gln Asn Val Leu Ser Leu Leu Arg
    210                 215                 220

<210> SEQ ID NO 55
<211> LENGTH: 507
<212> TYPE: DNA
<213> ORGANISM: Salmonella dublin

<400> SEQUENCE: 55
atgcggggtt ctcatcatca tcatcatcat ggtatggcta gcatgactgg tggacagcaa      60
atgggtcggg atctgtacga cgatgacgat aaggatccga tggcacaagt cattaataca     120
aacagcctgt cgctgttgac ccagaataac ctgaacaaat ctcagtcctc actgagttcc     180
gctattgagc gtctgtcctc tggtctgcgt atcaacagcg cgaaagacga tgcggcaggc     240
caggcgattg ctaaccgctt cacttctaat atcaaaggcc tgactcaggc ttcccgtaac     300
gctaacgaca tcccgggaat tccggtggt ggtggtggaa ttctagactc catgggtaca     360
ttaatcaatg aagacgctgc cgcagccaag aaaagtaccg ctaacccact ggcttcaatt     420
gattctgcat tgtcaaaagt ggacgcagtt cgttcttctc tgggggcaat tcaaaaccgt     480
tttgattcag ccattaccaa cctttag                                          507

<210> SEQ ID NO 56
<211> LENGTH: 168
<212> TYPE: PRT
<213> ORGANISM: Salmonella dublin

<400> SEQUENCE: 56

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Met Ala Gln Val Ile Asn Thr Asn Ser Leu Ser Leu Leu Thr Gln
        35                  40                  45

Asn Asn Leu Asn Lys Ser Gln Ser Ser Leu Ser Ser Ala Ile Glu Arg
    50                  55                  60

Leu Ser Ser Gly Leu Arg Ile Asn Ser Ala Lys Asp Asp Ala Ala Gly
65                  70                  75                  80

Gln Ala Ile Ala Asn Arg Phe Thr Ser Asn Ile Lys Gly Leu Thr Gln
                85                  90                  95

Ala Ser Arg Asn Ala Asn Asp Ile Pro Gly Ile Ser Gly Gly Gly Gly
            100                 105                 110

Gly Ile Leu Asp Ser Met Gly Thr Leu Ile Asn Glu Asp Ala Ala Ala
        115                 120                 125

Ala Lys Lys Ser Thr Ala Asn Pro Leu Ala Ser Ile Asp Ser Ala Leu
    130                 135                 140

Ser Lys Val Asp Ala Val Arg Ser Ser Leu Gly Ala Ile Gln Asn Arg
145                 150                 155                 160

Phe Asp Ser Ala Ile Thr Asn Leu
                165
```

```
<210> SEQ ID NO 57
<211> LENGTH: 174
<212> TYPE: PRT
<213> ORGANISM: Salmonella enterica

<400> SEQUENCE: 57

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ser Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ser
                85                  90                  95

Val Gln Ala Thr Asn Gly Thr Asn Ser Asp Ser Asp Leu Lys Ser Ile
            100                 105                 110

Gln Asp Glu Ile Gln Gln Arg Leu Glu Glu Ile Asp Arg Val Ser Asn
    115                 120                 125

Gln Thr Gln Phe Asn Gly Val Lys Val Leu Ser Gln Asp Asn Gln Met
130                 135                 140

Lys Ile Gln Val Gly Ala Asn Asp Gly Glu Thr Ile Thr Ile Asp Leu
145                 150                 155                 160

Gln Lys Ile Asp Val Lys Ser Leu Gly Leu Asp Gly Phe Asn
                165                 170

<210> SEQ ID NO 58
<211> LENGTH: 189
<212> TYPE: PRT
<213> ORGANISM: Pseudomonas aeruginosa

<400> SEQUENCE: 58

Met Ala Leu Thr Val Asn Thr Asn Ile Ala Ser Leu Asn Thr Gln Arg
1               5                   10                  15

Asn Leu Asn Ala Ser Ser Asn Asp Leu Asn Thr Ser Leu Gln Arg Leu
                20                  25                  30

Thr Thr Gly Tyr Arg Ile Asn Ser Ala Lys Asp Asp Ala Ala Gly Leu
            35                  40                  45

Gln Ile Ser Asn Arg Leu Ser Asn Gln Ile Ser Gly Leu Asn Val Ala
    50                  55                  60

Thr Arg Asn Ala Asn Asp Gly Ile Ser Leu Ala Gln Thr Ala Glu Gly
65                  70                  75                  80

Ala Leu Gln Gln Ser Thr Asn Ile Leu Gln Arg Ile Arg Asp Leu Ala
                85                  90                  95

Leu Gln Ser Ala Asn Gly Ser Asn Ser Asp Ala Asp Arg Ala Ala Leu
            100                 105                 110

Gln Lys Glu Val Ala Ala Gln Gln Ala Glu Leu Thr Arg Ile Ser Asp
    115                 120                 125

Thr Thr Thr Phe Gly Gly Arg Lys Leu Leu Asp Gly Ser Phe Gly Thr
130                 135                 140

Thr Ser Phe Gln Val Gly Ser Asn Ala Tyr Glu Thr Ile Asp Ile Ser
145                 150                 155                 160
```

Leu Gln Asn Ala Ser Ala Ser Ala Ile Gly Ser Tyr Gln Val Gly Ser
                165                 170                 175

Asn Gly Ala Gly Thr Val Ala Ser Val Ala Gly Thr Ala
            180                 185

<210> SEQ ID NO 59
<211> LENGTH: 179
<212> TYPE: PRT
<213> ORGANISM: Legionella pneumophila

<400> SEQUENCE: 59

Met Ala Gln Val Ile Asn Thr Asn Val Ala Ser Leu Thr Ala Gln Arg
1               5                   10                  15

Asn Leu Gly Val Ser Gly Asn Met Met Gln Thr Ser Ile Gln Arg Leu
            20                  25                  30

Ser Ser Gly Leu Arg Ile Asn Ser Ala Lys Asp Asp Ala Ala Gly Leu
        35                  40                  45

Ala Ile Ser Gln Arg Met Thr Ala Gln Ile Arg Gly Met Asn Gln Ala
    50                  55                  60

Val Arg Asn Ala Asn Asp Gly Ile Ser Leu Ala Gln Val Ala Glu Gly
65                  70                  75                  80

Ala Met Gln Glu Thr Thr Asn Ile Leu Gln Arg Met Arg Glu Leu Ser
                85                  90                  95

Val Gln Ala Ala Asn Ser Thr Asn Asn Ser Ser Asp Arg Ala Ser Ile
            100                 105                 110

Gln Ser Glu Ile Ser Gln Leu Lys Ser Glu Leu Glu Arg Ile Ala Gln
        115                 120                 125

Asn Thr Glu Phe Asn Gly Gln Arg Ile Leu Asp Gly Ser Phe Ser Gly
    130                 135                 140

Ala Ser Phe Gln Val Gly Ala Asn Ser Asn Gln Thr Ile Asn Phe Ser
145                 150                 155                 160

Ile Gly Ser Ile Lys Ala Ser Ser Ile Gly Ile Ala Thr Ala Thr
                165                 170                 175

Gly Thr Glu

<210> SEQ ID NO 60
<211> LENGTH: 174
<212> TYPE: PRT
<213> ORGANISM: Escherichia coli

<400> SEQUENCE: 60

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Val Ala Gln Thr Thr Glu Gly
65                  70                  75                  80

Ala Leu Asn Glu Ile Asn Asn Asn Leu Gln Arg Val Arg Glu Leu Thr
                85                  90                  95

Val Gln Ala Thr Asn Gly Thr Asn Ser Asp Ser Asp Leu Ser Ser Ile
            100                 105                 110

```
Gln Ala Glu Ile Thr Gln Arg Leu Glu Glu Ile Asp Arg Val Ser Glu
            115                 120                 125
Gln Thr Gln Phe Asn Gly Val Lys Val Leu Ala Glu Asn Asn Glu Met
        130                 135                 140
Lys Ile Gln Val Gly Ala Asn Asp Gly Glu Thr Ile Thr Ile Asn Leu
145                 150                 155                 160
Ala Lys Ile Asp Ala Lys Thr Leu Gly Leu Asp Gly Phe Asn
                165                 170
```

<210> SEQ ID NO 61
<211> LENGTH: 173
<212> TYPE: PRT
<213> ORGANISM: Serratia marcescens

<400> SEQUENCE: 61

```
Met Ala Gln Val Ile Asn Thr Asn Ser Leu Ser Leu Met Ala Gln Asn
1               5                   10                  15
Asn Leu Asn Lys Ser Gln Ser Ser Leu Gly Thr Ala Ile Glu Arg Leu
            20                  25                  30
Ser Ser Gly Leu Arg Ile Asn Ser Ala Lys Asp Asp Ala Ala Gly Gln
        35                  40                  45
Ala Ile Ser Asn Arg Phe Thr Ala Asn Ile Lys Gly Leu Thr Gln Ala
    50                  55                  60
Ser Arg Asn Ala Asn Asp Gly Ile Ser Leu Ala Gln Thr Thr Glu Gly
65                  70                  75                  80
Ala Leu Asn Glu Val Asn Asp Asn Leu Gln Asn Ile Arg Arg Leu Thr
                85                  90                  95
Val Gln Ala Gln Asn Gly Ser Asn Ser Thr Ser Asp Leu Lys Ser Ile
            100                 105                 110
Gln Asp Glu Ile Thr Gln Arg Leu Ser Glu Ile Asn Arg Ile Ser Glu
        115                 120                 125
Gln Thr Asp Phe Asn Gly Val Lys Val Leu Ser Ser Asp Gln Lys Leu
    130                 135                 140
Thr Ile Gln Val Gly Ala Asn Asp Gly Glu Thr Thr Asp Ile Asp Leu
145                 150                 155                 160
Lys Lys Ile Asp Ala Lys Gln Leu Gly Met Asp Thr Phe
                165                 170
```

<210> SEQ ID NO 62
<211> LENGTH: 168
<212> TYPE: PRT
<213> ORGANISM: Bacillus subtilis

<400> SEQUENCE: 62

```
Met Arg Ile Asn His Asn Ile Ala Ala Leu Asn Thr Ser Arg Gln Leu
1               5                   10                  15
Asn Ala Gly Ser Asn Ser Ala Ala Lys Asn Met Glu Lys Leu Ser Ser
            20                  25                  30
Gly Leu Arg Ile Asn Arg Ala Gly Asp Asp Ala Ala Gly Leu Ala Ile
        35                  40                  45
Ser Glu Lys Met Arg Ser Gln Ile Arg Gly Leu Asp Met Ala Ser Lys
    50                  55                  60
Asn Ala Gln Asp Gly Ile Ser Leu Ile Gln Thr Ser Glu Gly Ala Leu
65                  70                  75                  80
Asn Glu Thr His Ser Ile Leu Gln Arg Met Ser Glu Leu Ala Thr Gln
                85                  90                  95
```

```
Ala Ala Asn Asp Thr Asn Thr Asp Ser Asp Arg Ser Glu Leu Gln Lys
            100                 105                 110

Glu Met Asp Gln Leu Ala Ser Glu Val Thr Arg Ile Ser Thr Asp Thr
        115                 120                 125

Glu Phe Asn Thr Lys Lys Leu Leu Asp Gly Thr Ala Gln Asn Leu Thr
    130                 135                 140

Phe Gln Ile Gly Ala Asn Glu Gly Gln Thr Met Ser Leu Ser Ile Asn
145                 150                 155                 160

Lys Met Asp Ser Glu Ser Leu Lys
                165

<210> SEQ ID NO 63
<211> LENGTH: 192
<212> TYPE: PRT
<213> ORGANISM: Listeria monocytogenes

<400> SEQUENCE: 63

Met Lys Val Asn Thr Asn Ile Ile Ser Leu Lys Thr Gln Glu Tyr Leu
1               5                   10                  15

Arg Lys Asn Asn Glu Gly Met Thr Gln Ala Gln Glu Arg Leu Ala Ser
            20                  25                  30

Gly Lys Arg Ile Asn Ser Ser Leu Asp Asp Ala Ala Gly Leu Ala Val
        35                  40                  45

Val Thr Arg Met Asn Val Lys Ser Thr Gly Leu Asp Ala Ala Ser Lys
    50                  55                  60

Asn Ser Ser Met Gly Ile Asp Leu Leu Gln Thr Ala Asp Ser Ala Leu
65                  70                  75                  80

Ser Ser Met Ser Ser Ile Leu Gln Arg Met Arg Gln Leu Ala Val Gln
                85                  90                  95

Ser Ser Asn Gly Ser Phe Ser Asp Glu Asp Arg Lys Gln Tyr Thr Ala
            100                 105                 110

Glu Phe Gly Ser Leu Ile Lys Glu Leu Asp His Val Ala Asp Thr Thr
        115                 120                 125

Asn Tyr Asn Asn Ile Lys Leu Leu Asp Gln Thr Ala Thr Gly Ala Ala
    130                 135                 140

Thr Gln Val Ser Ile Gln Ala Ser Asp Lys Ala Asn Asp Leu Ile Asn
145                 150                 155                 160

Ile Asp Leu Phe Asn Ala Lys Gly Leu Ser Ala Gly Thr Ile Thr Leu
                165                 170                 175

Gly Ser Gly Ser Thr Val Ala Gly Tyr Ser Ala Leu Ser Val Ala Asp
            180                 185                 190

<210> SEQ ID NO 64
<211> LENGTH: 174
<212> TYPE: PRT
<213> ORGANISM: Shigella sonnei

<400> SEQUENCE: 64

Met Ala Gln Val Ile Asn Thr Asn Ser Leu Ser Leu Leu Thr Gln Asn
1               5                   10                  15

Asn Leu Asn Lys Ser Gln Ser Ser Leu Ser Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60
```

```
Ser Arg Asn Ala Asn Asp Gly Ile Ser Val Ala Gln Thr Thr Glu Gly
 65                  70                  75                  80

Ala Leu Ser Glu Ile Asn Asn Asn Leu Gln Arg Ile Arg Glu Leu Ser
                 85                  90                  95

Val Gln Ala Thr Asn Gly Thr Asn Ser Asp Ser Asp Leu Asn Ser Ile
            100                 105                 110

Gln Asp Glu Ile Thr Gln Arg Leu Ser Glu Ile Asp Arg Val Ser Asn
        115                 120                 125

Gln Thr Gln Phe Asn Gly Val Lys Val Leu Ala Ser Asp Gln Thr Met
    130                 135                 140

Lys Ile Gln Val Gly Ala Asn Asp Gly Glu Thr Ile Glu Ile Ala Leu
145                 150                 155                 160

Asp Lys Ile Asp Ala Lys Thr Leu Gly Leu Asp Asn Phe Ser
                165                 170

<210> SEQ ID NO 65
<211> LENGTH: 174
<212> TYPE: PRT
<213> ORGANISM: Edwardsiella tarda

<400> SEQUENCE: 65

Met Ala Gln Val Ile Asn Thr Asn Ser Leu Ser Leu Met Ala Gln Asn
 1               5                  10                  15

Asn Leu Asn Lys Ser Gln Ser Ala Leu Gly Thr Ala Ile Glu Arg Leu
             20                  25                  30

Ser Ser Gly Leu Arg Ile Asn Ser Ala Lys Asp Asp Ala Ala Gly Gln
         35                  40                  45

Ala Ile Ser Asn Arg Phe Thr Ala Asn Ile Asn Gly Leu Thr Gln Ala
     50                  55                  60

Ser Arg Asn Ala Asn Asp Gly Ile Ser Leu Ala Gln Thr Thr Glu Gly
 65                  70                  75                  80

Ala Leu Asn Glu Val Asn Asp Asn Leu Gln Asn Ile Arg Arg Leu Thr
                 85                  90                  95

Val Gln Ala Gln Asn Gly Ser Asn Ser Ser Asp Leu Gln Ser Ile
            100                 105                 110

Gln Asp Glu Ile Thr Gln Arg Leu Ser Glu Ile Asp Arg Ile Ser Gln
        115                 120                 125

Gln Thr Asp Phe Asn Gly Val Lys Val Leu Ser Lys Asp Gln Lys Leu
    130                 135                 140

Thr Ile Gln Val Gly Ala Asn Asp Gly Glu Thr Ile Asp Ile Asp Leu
145                 150                 155                 160

Lys Asn Ile Asn Ala Gln Ser Leu Gly Leu Asp Lys Phe Asn
                165                 170

<210> SEQ ID NO 66
<211> LENGTH: 186
<212> TYPE: PRT
<213> ORGANISM: Acidovorax avenae

<400> SEQUENCE: 66

Met Ala Ser Thr Ile Asn Thr Asn Val Ser Ser Leu Thr Ala Gln Arg
 1               5                  10                  15

Asn Leu Ser Leu Ser Gln Ser Ser Leu Asn Thr Ser Ile Gln Arg Leu
             20                  25                  30

Ser Ser Gly Leu Arg Ile Asn Ser Ala Lys Asp Asp Ala Ala Gly Leu
         35                  40                  45
```

```
Ala Ile Ser Glu Arg Phe Thr Ser Gln Ile Arg Gly Leu Asn Gln Ala
        50                  55                  60

Val Arg Asn Ala Asn Asp Gly Ile Ser Leu Ala Gln Thr Ala Glu Gly
 65                  70                  75                  80

Ala Leu Lys Ser Thr Gly Asp Ile Leu Gln Arg Val Arg Glu Leu Ala
                 85                  90                  95

Val Gln Ser Ala Asn Ala Thr Asn Ser Ser Gly Asp Arg Lys Ala Ile
                100                 105                 110

Gln Ala Glu Val Gly Gln Leu Leu Ser Glu Met Asp Arg Ile Ala Gly
                115                 120                 125

Asn Thr Glu Phe Asn Gly Gln Lys Leu Leu Asp Gly Ser Phe Gly Ser
        130                 135                 140

Ala Thr Phe Gln Val Gly Ala Asn Ala Asn Gln Thr Ile Thr Ala Thr
145                 150                 155                 160

Thr Gly Asn Phe Arg Thr Asn Asn Tyr Gly Ala Gln Leu Thr Ala Ser
                    165                 170                 175

Ala Ser Gly Ala Ala Thr Ser Gly Ala Ser
                180                 185
```

<210> SEQ ID NO 67
<211> LENGTH: 173
<212> TYPE: PRT
<213> ORGANISM: Yersinia pestis

<400> SEQUENCE: 67

```
Met Ala Val Ile Asn Thr Asn Ser Leu Ser Leu Leu Thr Gln Asn Asn
  1

Asn Leu Asn Arg Ser Gln Gly Thr Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Arg Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Thr Asn Leu Gln Arg Ile Arg Glu Leu Thr
                85                  90                  95

Val Gln Ser Gln Asn Gly Ser Asn Ser Glu Ser Asp Ile Lys Ser Ile
            100                 105                 110

Gln Glu Glu Val Thr Gln Arg Leu Lys Glu Ile Asp Arg Ile Ser Glu
        115                 120                 125

Gln Thr Gln Phe Asn Gly Val Arg Val Leu Arg Glu Asp Ser Lys Met
    130                 135                 140

Thr Ile Gln Val Gly Ala Asn Asp Asn Glu Val Ile Asp Ile Asp Leu
145                 150                 155                 160

Lys Lys Ile Asp Lys Glu Ala Leu Asn Leu Gly Lys Phe Thr
                165                 170

<210> SEQ ID NO 69
<211> LENGTH: 189
<212> TYPE: PRT
<213> ORGANISM: Rhodobacter sphaeroides

<400> SEQUENCE: 69

Met Thr Thr Ile Asn Thr Asn Ile Gly Ala Ile Ala Ala Gln Ala Asn
1               5                   10                  15

Met Thr Lys Val Asn Asp Gln Phe Asn Thr Ala Met Thr Arg Leu Ser
            20                  25                  30

Thr Gly Leu Arg Ile Asn Ala Ala Lys Asp Asp Ala Ala Gly Met Ala
        35                  40                  45

Ile Gly Glu Lys Met Thr Ala Gln Val Met Gly Leu Asn Gln Ala Ile
    50                  55                  60

Arg Asn Ala Gln Asp Gly Lys Asn Leu Val Asp Thr Thr Glu Gly Ala
65                  70                  75                  80

His Val Glu Val Ser Ser Met Leu Gln Arg Leu Arg Glu Leu Ala Val
                85                  90                  95

Gln Ser Ser Asn Asp Thr Asn Thr Ala Ala Asp Arg Gly Ser Leu Ala
            100                 105                 110

Ala Glu Gly Lys Gln Leu Ile Ala Glu Ile Asn Arg Val Ala Glu Ser
        115                 120                 125

Thr Thr Phe Asn Gly Met Lys Val Leu Asp Gly Ser Phe Thr Gly Lys
    130                 135                 140

Gln Leu Gln Ile Gly Ala Asp Ser Gly Gln Thr Met Ala Ile Asn Val
145                 150                 155                 160

Asp Ser Ala Ala Ala Thr Asp Ile Gly Ala His Lys Ile Ser Ser Ala
                165                 170                 175

Ser Thr Val Val Ala Asp Ala Ala Leu Thr Asp Thr Thr
            180                 185

<210> SEQ ID NO 70
<211> LENGTH: 175
<212> TYPE: PRT
<213> ORGANISM: Xenorhabdus nematophila

<400> SEQUENCE: 70

Met Ala Ser Val Ile Asn Thr Asn Asp Ser Ala Leu Leu Ala Gln Asn
1               5                   10                  15

Asn Leu Thr Lys Ser Lys Gly Ile Leu Gly Ser Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Val Lys Gly Leu Thr Gln Ala
    50                  55                  60

Ala Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ser Glu Asn Gly Ser Asn Ser Lys Ser Asp Leu Asp Ser Ile
            100                 105                 110

Gln Lys Glu Val Thr Gln Arg Leu Glu Glu Ile Asp Arg Ile Ser Thr
        115                 120                 125

Gln Thr Gln Phe Asn Gly Ile Lys Val Leu Asn Gly Asp Val Thr Glu
    130                 135                 140

Met Lys Ile Gln Val Gly Ala Asn Asp Asn Glu Thr Ile Gly Ile Lys
145                 150                 155                 160

Leu Gly Lys Ile Asn Ser Glu Lys Leu Asn Leu Lys Glu Phe Ser
                165                 170                 175

<210> SEQ ID NO 71
<211> LENGTH: 175
<212> TYPE: PRT
<213> ORGANISM: Proteus mirabilis

<400> SEQUENCE: 71

Met Ala Gln Val Ile Asn Thr Asn Tyr Leu Ser Leu Val Thr Gln Asn
1               5                   10                  15

Asn Leu Asn Arg Ser Gln Ser Ala Leu Gly Asn Ala Ile Glu Arg Leu
            20                  25                  30

Ser Ser Gly Met Arg Ile Asn Ser Ala Lys Asp Asp Ala Ala Gly Gln
        35                  40                  45

Ala Ile Ala Asn Arg Phe Thr Ser Asn Ile Asn Gly Leu Thr Gln Ala
    50                  55                  60

Ser Arg Asn Ala Asn Asp Gly Ile Ser Val Ser Gln Thr Thr Glu Gly
65                  70                  75                  80

Ala Leu Asn Glu Ile Asn Asn Asn Leu Gln Arg Ile Arg Glu Leu Thr
                85                  90                  95

Val Gln Ala Lys Asn Gly Thr Asn Ser Asn Ser Asp Ile Asn Ser Ile
            100                 105                 110

Gln Asn Glu Val Asn Gln Arg Leu Asp Glu Ile Asn Arg Val Ser Glu
        115                 120                 125

Gln Thr Gln Phe Asn Gly Val Lys Val Leu Ser Gly Glu Lys Ser Lys
    130                 135                 140

Met Thr Ile Gln Val Gly Thr Asn Asp Asn Glu Val Ile Glu Phe Asn
145                 150                 155                 160

Leu Asp Lys Ile Asp Asn Asp Thr Leu Gly Val Ala Ser Asp Lys
                165                 170                 175

<210> SEQ ID NO 72

<211> LENGTH: 200
<212> TYPE: PRT
<213> ORGANISM: Butyrivibrio fibrisolvens

<400> SEQUENCE: 72

```
Met Val Val Gln His Asn Met Gln Ala Ala Asn Ala Ser Arg Met Leu
1               5                   10                  15
Gly Ile Thr Thr Gly Asp Gln Ser Lys Ser Thr Glu Lys Leu Ser Ser
            20                  25                  30
Gly Phe Lys Ile Asn Arg Ala Ala Asp Asp Ala Ala Gly Leu Ser Ile
        35                  40                  45
Ser Glu Lys Met Arg Lys Gln Ile Arg Gly Leu Asp Gln Ala Ser Thr
50                  55                  60
Asn Ala Ser Asp Gly Ile Ser Ala Val Gln Thr Ala Glu Gly Ala Leu
65                  70                  75                  80
Thr Glu Val His Ser Met Leu Gln Arg Met Asn Glu Leu Ala Val Gln
                85                  90                  95
Ala Ala Asn Gly Thr Asn Ser Glu Ser Asp Arg Ser Ser Ile Gln Asp
            100                 105                 110
Glu Ile Asn Gln Leu Thr Thr Glu Ile Asp Arg Val Ala Glu Thr Thr
        115                 120                 125
Lys Phe Asn Glu Thr Tyr Leu Leu Lys Gly Gly Asn Gly Asp Arg Thr
130                 135                 140
Val Arg Val Tyr Ala His Asp Ala Gly Leu Val Gly Ser Leu Ser Gln
145                 150                 155                 160
Asn Thr Thr Lys Ala Thr Phe Gln Met Arg Lys Leu Glu Ile Gly Asp
                165                 170                 175
Ser Tyr Thr Ile Gly Gly Thr Thr Tyr Lys Ile Gly Ala Glu Thr Val
            180                 185                 190
Lys Glu Ala Met Thr Ala Leu Lys
        195                 200
```

<210> SEQ ID NO 73
<211> LENGTH: 177
<212> TYPE: PRT
<213> ORGANISM: Bordetella pertussis

<400> SEQUENCE: 73

Met Ala Ala Val Ile Asn Thr Asn Tyr Leu Ser Leu Val Ala Gln Asn
1 5 10 15

Asn Leu Asn Lys Ser Gln Ser Ala Leu Gly Ser Ala Ile Glu Arg Leu
20 25 30

Ser Ser Gly Leu Arg Ile Asn Ser Ala Lys Asp Asp Ala Ala Gly Gln
35 40 45

Ala Ile Ala Asn Arg Phe Thr Ala Asn Val Lys Gly Leu Thr Gln Ala
50 55 60

Ala Arg Asn Ala Asn Asp Gly Ile Ser Ile Ala Gln Thr Thr Glu Gly
65 70 75 80

Ala Leu Asn Glu Ile Asn Asn Asn Leu Gln Arg Ile Arg Glu Leu Thr
85 90 95

Val Gln Ala Ser Asn Gly Thr Asn Ser Ala Ser Asp Ile Asp Ser Ile
100 105 110

Gln Gln Glu Val Asn Gln Arg Leu Glu Glu Ile Asn Arg Ile Ala Glu
115 120 125

Gln Thr Asp Phe Asn Gly Ile Lys Val Leu Lys Ser Asn Ala Thr Asp
130 135 140

Met Thr Leu Ser Ile Gln Val Gly Ala Lys Asp Asn Glu Thr Ile Asp
145                 150                 155                 160

Ile Lys Ile Asp Arg Asn Ser Asn Trp Asn Leu Tyr Asp Ala Val Gly
                165                 170                 175

Thr

<210> SEQ ID NO 74
<211> LENGTH: 167
<212> TYPE: PRT
<213> ORGANISM: Clostridium chauvoei

<400> SEQUENCE: 74

Met Ile Ile Asn His Asn Met Asn Ala Leu Asn Ala His Arg Asn Met
1               5                   10                  15

Met Gly Asn Ile Ala Thr Ala Gly Lys Ser Met Glu Lys Leu Ser Ser
                20                  25                  30

Gly Leu Arg Ile Asn Arg Ala Gly Asp Asp Ala Ala Gly Leu Ala Ile
            35                  40                  45

Ser Glu Lys Met Arg Gly Gln Ile Arg Gly Leu Asp Gln Ala Ser Arg
    50                  55                  60

Asn Ala Gln Asp Gly Ile Ser Leu Ile Gln Thr Ala Glu Gly Ala Leu
65                  70                  75                  80

Ala Glu Thr His Ser Ile Leu Gln Arg Met Arg Glu Leu Ser Val Gln
                85                  90                  95

Ser Ala Asn Asp Thr Asn Val Ala Val Asp Arg Thr Ala Ile Gln Asp
            100                 105                 110

Glu Ile Asn Ser Leu Thr Glu Glu Ile Asn Arg Ile Ser Gly Asp Thr
        115                 120                 125

Glu Phe Asn Thr Gln Lys Leu Leu Asp Gly Gly Phe Lys Gly Glu Phe
    130                 135                 140

Gln Ile Gly Ala Asn Ser Asn Gln Thr Val Lys Leu Asp Ile Gly Asn
145                 150                 155                 160

Met Ser Ala Ala Ser Leu Gly
                165

<210> SEQ ID NO 75
<211> LENGTH: 178
<212> TYPE: PRT
<213> ORGANISM: Xanthomonas campestris

<400> SEQUENCE: 75

Met Ala Gln Val Ile Asn Thr Asn Val Met Ser Leu Asn Ala Gln Arg
1               5                   10                  15

Asn Leu Asn Thr Asn Ser Ser Ser Met Ala Leu Ser Ile Gln Gln Leu
                20                  25                  30

Ser Ser Gly Lys Arg Ile Thr Ser Ala Ser Val Asp Ala Ala Gly Leu
            35                  40                  45

Ala Ile Ser Glu Arg Phe Thr Thr Gln Ile Arg Gly Leu Asp Val Ala
    50                  55                  60

Ser Arg Asn Ala Asn Asp Gly Ile Ser Leu Ala Gln Thr Ala Glu Gly
65                  70                  75                  80

Ala Met Val Glu Ile Gly Asn Asn Leu Gln Arg Ile Arg Glu Leu Ser
                85                  90                  95

Val Gln Ser Ala Asn Ala Thr Asn Ser Ala Thr Asp Arg Glu Ala Leu
            100                 105                 110

```
Asn Ser Glu Val Lys Gln Leu Thr Ser Glu Ile Asp Arg Val Ala Asn
            115                 120                 125

Gln Thr Ser Phe Asn Gly Thr Lys Leu Leu Asn Gly Asp Phe Ser Gly
        130                 135                 140

Ala Leu Phe Gln Val Gly Ala Asp Ala Gly Gln Thr Ile Gly Ile Asn
145                 150                 155                 160

Ser Ile Val Asp Ala Asn Val Asp Ser Leu Gly Lys Ala Asn Phe Ala
                165                 170                 175

Ala Ser
```

<210> SEQ ID NO 76
<211> LENGTH: 161
<212> TYPE: PRT
<213> ORGANISM: Nitrosomonas europaea

<400> SEQUENCE: 76

```
Met Pro Gln Val Ile Asn Thr Asn Ile Ala Ser Leu Asn Ala Gln Arg
1               5                   10                  15

Asn Leu Asn Val Ser Gln Asn Ser Leu Ser Thr Ala Leu Gln Arg Leu
            20                  25                  30

Ser Ser Gly Leu Arg Ile Asn Ser Ala Lys Asp Asp Ala Ala Gly Leu
        35                  40                  45

Ala Ile Ser Glu Arg Met Thr Ser Gln Ile Arg Gly Met Asn Gln Ala
50                  55                  60

Ala Arg Asn Ala Asn Asp Gly Ile Ser Leu Ala Gln Thr Ala Glu Gly
65                  70                  75                  80

Ala Leu Val Glu Ile Gly Asn Asn Leu Gln Arg Ile Arg Glu Leu Ala
                85                  90                  95

Val Gln Ser Ala Asn Ala Thr Asn Ser Glu Asp Asp Arg Glu Ala Leu
            100                 105                 110

Gln Lys Glu Val Thr Gln Leu Ile Asp Glu Ile Gln Arg Val Gly Glu
        115                 120                 125

Gln Thr Ser Phe Asn Gly Thr Lys Leu Leu Asp Gly Ser Phe Ala Ser
    130                 135                 140

Gln Ile Phe Gln Val Gly Ala Asn Glu Gly Glu Thr Ile Asp Phe Thr
145                 150                 155                 160

Asp
```

<210> SEQ ID NO 77
<211> LENGTH: 178
<212> TYPE: PRT
<213> ORGANISM: Campylobacter lari

<400> SEQUENCE: 77

```
Gly Phe Arg Ile Asn Thr Asn Gly Ala Ser Leu Asn Ala Gln Val Asn
1               5                   10                  15

Ala Gly Leu Asn Ser Arg Asn Leu Asp Ser Ser Leu Ala Arg Leu Ser
            20                  25                  30

Ser Gly Leu Arg Ile Asn Ser Ala Ala Asp Asp Ala Ser Gly Leu Ala
        35                  40                  45

Ile Ala Asp Ser Leu Lys Thr Gln Ala Asn Ser Leu Gly Gln Ala Ile
50                  55                  60

Asn Asn Ala Asn Asp Ala Asn Ser Met Leu Gln Ile Ala Asp Lys Ala
65                  70                  75                  80

Met Asp Glu Gln Leu Lys Ile Leu Asp Thr Ile Lys Val Lys Ala Thr
                85                  90                  95
```

```
Gln Ala Ala Gln Asp Gly Gln Thr Ala Lys Thr Arg Ala Met Ile Gln
                100                 105                 110

Gly Glu Ile Asn Lys Leu Met Glu Glu Leu Asp Asn Ile Ala Asn Thr
            115                 120                 125

Thr Thr Tyr Asn Gly Lys Gln Leu Leu Ser Gly Ser Phe Ser Asn Ala
        130                 135                 140

Gln Phe Gln Ile Gly Asp Lys Ala Asn Gln Thr Val Asn Ala Thr Ile
145                 150                 155                 160

Gly Ser Thr Asn Ser Ala Lys Val Gly Gln Thr Arg Phe Glu Thr Gly
                165                 170                 175

Ala Val

<210> SEQ ID NO 78
<211> LENGTH: 88
<212> TYPE: PRT
<213> ORGANISM: Salmonella enterica

<400> SEQUENCE: 78

Pro Leu Ala Ser Ile Asp Ser Ala Leu Ser Lys Val Asp Ala Val Arg
1               5                   10                  15

Ser Ser Leu Gly Ala Ile Gln Asn Arg Phe Asp Ser Ala Ile Thr Asn
            20                  25                  30

Leu Gly Asn Thr Val Thr Asn Leu Asn Ser Ala Arg Ser Arg Ile Glu
        35                  40                  45

Asp Ala Asp Tyr Ala Thr Glu Val Ser Asn Met Ser Lys Ala Gln Ile
    50                  55                  60

Leu Gln Gln Ala Gly Thr Ser Val Leu Ala Gln Ala Asn Gln Val Pro
65                  70                  75                  80

Gln Asn Val Leu Ser Leu Leu Arg
                85

<210> SEQ ID NO 79
<211> LENGTH: 88
<212> TYPE: PRT
<213> ORGANISM: Pseudomonas aeruginosa

<400> SEQUENCE: 79

Ala Ile Ala Val Val Asp Asn Ala Leu Ala Ile Asp Ala Gln Arg
1               5                   10                  15

Ala Asp Leu Gly Ala Val Gln Asn Arg Phe Lys Asn Thr Ile Asp Asn
            20                  25                  30

Leu Thr Asn Ile Ser Glu Asn Ala Thr Asn Ala Arg Ser Arg Ile Lys
        35                  40                  45

Asp Thr Asp Phe Ala Ala Glu Thr Ala Ala Leu Ser Lys Asn Gln Val
    50                  55                  60

Leu Gln Gln Ala Gly Thr Ala Ile Leu Ala Gln Ala Asn Gln Leu Pro
65                  70                  75                  80

Gln Ala Val Leu Ser Leu Leu Arg
                85

<210> SEQ ID NO 80
<211> LENGTH: 89
<212> TYPE: PRT
<213> ORGANISM: Legionella pneumophila

<400> SEQUENCE: 80

Ala Ile Lys Arg Ile Asp Ala Ala Leu Asn Ser Val Asn Ser Asn Arg
```

```
                1               5                  10                 15
          Ala Asn Met Gly Ala Leu Gln Asn Arg Phe Glu Ser Thr Ile Ala Asn
                              20                  25                 30

Leu Gln Asn Val Ser Asp Asn Leu Ser Ala Ala Arg Ser Arg Ile Gln
                              35                  40                 45

Asp Ala Asp Tyr Ala Ala Glu Met Ala Ser Leu Thr Lys Asn Gln Ile
                      50                  55                 60

Leu Gln Gln Ala Gly Thr Ala Met Leu Ala Gln Ala Asn Ser Leu Pro
           65                  70                  75                 80

Gln Ser Val Leu Ser Leu Leu Gly Arg
                              85

<210> SEQ ID NO 81
<211> LENGTH: 89
<212> TYPE: PRT
<213> ORGANISM: Escherichia coli

<400> SEQUENCE: 81

Pro Leu Glu Thr Ile Asp Lys Ala Leu Ala Lys Val Asp Asn Leu Arg
           1               5                  10                 15

Ser Asp Leu Gly Ala Val Gln Asn Arg Phe Asp Ser Ala Ile Thr Asn
                              20                  25                 30

Leu Gly Asn Thr Val Asn Asn Leu Ser Ser Ala Arg Ser Arg Ile Glu
                              35                  40                 45

Asp Ala Asp Tyr Ala Thr Glu Val Ser Asn Met Ser Arg Ala Gln Ile
                      50                  55                 60

Leu Gln Gln Ala Gly Thr Ser Val Leu Ala Gln Ala Asn Gln Thr Thr
           65                  70                  75                 80

Gln Asn Val Leu Ser Leu Leu Gln Gly
                              85

<210> SEQ ID NO 82
<211> LENGTH: 88
<212> TYPE: PRT
<213> ORGANISM: Serratia marcescens

<400> SEQUENCE: 82

Pro Leu Ala Thr Leu Asp Lys Ala Leu Ala Gln Val Asp Gly Leu Arg
           1               5                  10                 15

Ser Ser Leu Gly Ala Val Gln Asn Arg Phe Asp Ser Val Ile Asn Asn
                              20                  25                 30

Leu Asn Ser Thr Val Asn Asn Leu Ser Ala Ser Gln Ser Arg Ile Gln
                              35                  40                 45

Asp Ala Asp Tyr Ala Thr Glu Val Ser Asn Met Ser Arg Ala Asn Ile
                      50                  55                 60

Leu Gln Gln Ala Gly Thr Ser Val Leu Ala Gln Ala Asn Gln Ser Thr
           65                  70                  75                 80

Gln Asn Val Leu Ser Leu Leu Arg
                              85

<210> SEQ ID NO 83
<211> LENGTH: 89
<212> TYPE: PRT
<213> ORGANISM: Bacillus subtilis

<400> SEQUENCE: 83

Ala Leu Thr Thr Ile Lys Thr Ala Ile Asp Thr Val Ser Ser Glu Arg
           1               5                  10                 15
```

```
Ala Lys Leu Gly Ala Val Gln Asn Arg Leu Glu His Thr Ile Asn Asn
            20                  25                  30

Leu Gly Thr Ser Ser Glu Asn Leu Thr Ser Ala Glu Ser Arg Ile Arg
        35                  40                  45

Asp Val Asp Met Ala Ser Glu Met Met Glu Tyr Thr Lys Asn Asn Ile
 50                  55                  60

Leu Thr Gln Ala Ser Gln Ala Met Leu Ala Gln Ala Asn Gln Pro
 65                  70                  75                  80

Gln Gln Val Leu Gln Leu Leu Lys Gly
                85
```

<210> SEQ ID NO 84
<211> LENGTH: 90
<212> TYPE: PRT
<213> ORGANISM: Leptospira interrogans

<400> SEQUENCE: 84

```
Val Ile Gly Leu Ala Asp Ala Ala Leu Thr Lys Ile Met Lys Gln Arg
 1               5                  10                  15

Ala Asp Met Gly Ala Tyr Tyr Asn Arg Leu Glu Tyr Thr Ala Lys Gly
            20                  25                  30

Leu Met Gly Ala Tyr Glu Asn Met Gln Ala Ser Glu Ser Arg Ile Arg
        35                  40                  45

Asp Ala Asp Met Ala Glu Glu Val Val Ser Leu Thr Thr Lys Gln Ile
 50                  55                  60

Leu Val Gln Ser Gly Thr Ala Met Leu Ala Gln Ala Asn Met Lys Pro
 65                  70                  75                  80

Asn Ser Val Leu Lys Leu Leu Gln Gln Ile
                85                  90
```

<210> SEQ ID NO 85
<211> LENGTH: 88
<212> TYPE: PRT
<213> ORGANISM: Shigella sonnei

<400> SEQUENCE: 85

```
Pro Leu Ser Lys Leu Asp Glu Ala Leu Ala Lys Val Asp Lys Leu Arg
 1               5                  10                  15

Ser Ser Leu Gly Ala Val Gln Asn Arg Phe Asp Ser Ala Ile Thr Asn
            20                  25                  30

Leu Gly Asn Thr Val Asn Asp Leu Ser Ser Ala Arg Ser Arg Ile Glu
        35                  40                  45

Asp Ala Asp Tyr Ala Thr Glu Val Ser Asn Met Ser Arg Ala Gln Ile
 50                  55                  60

Leu Gln Gln Ala Gly Thr Ser Val Leu Ala Gln Ala Asn Gln Thr Thr
 65                  70                  75                  80

Gln Asn Val Leu Ser Leu Leu Arg
                85
```

<210> SEQ ID NO 86
<211> LENGTH: 88
<212> TYPE: PRT
<213> ORGANISM: Edwardsiella tarda

<400> SEQUENCE: 86

```
Pro Leu Ala Thr Leu Asp Lys Ala Leu Ser Gln Val Asp Asp Leu Arg
 1               5                  10                  15
```

```
Ser Gly Leu Gly Ala Val Gln Asn Arg Phe Asp Ser Val Ile Asn Asn
            20                  25                  30

Leu Asn Ser Thr Val Asn Asn Leu Ser Ala Ser Arg Ser Arg Ile Gln
        35                  40                  45

Asp Ala Asp Tyr Ala Thr Glu Val Ser Asn Met Ser Arg Ala Gln Ile
    50                  55                  60

Leu Gln Gln Ala Gly Thr Ser Val Leu Ala Gln Ala Asn Gln Ser Thr
65                  70                  75                  80

Gln Asn Val Leu Ser Leu Leu Arg
                85

<210> SEQ ID NO 87
<211> LENGTH: 88
<212> TYPE: PRT
<213> ORGANISM: Acidovorax avenae

<400> SEQUENCE: 87

Ala Leu Lys Ile Ile Asp Ala Ala Leu Ser Ala Val Asn Gly Gln Arg
1               5                   10                  15

Ala Ser Phe Gly Ala Leu Gln Ser Arg Phe Glu Thr Thr Val Asn Asn
            20                  25                  30

Leu Gln Ser Thr Ser Glu Asn Met Ser Ala Ser Arg Ser Arg Ile Gln
        35                  40                  45

Asp Ala Asp Phe Ala Ala Glu Thr Ala Asn Leu Ser Arg Ser Gln Ile
    50                  55                  60

Leu Gln Gln Ala Gly Thr Ala Met Val Ala Gln Ala Asn Gln Leu Pro
65                  70                  75                  80

Gln Gly Val Leu Ser Leu Leu Lys
                85

<210> SEQ ID NO 88
<211> LENGTH: 88
<212> TYPE: PRT
<213> ORGANISM: Yersinia pestis

<400> SEQUENCE: 88

Pro Leu Glu Thr Leu Asp Asp Ala Ile Lys Gln Val Asp Gly Leu Arg
1               5                   10                  15

Ser Ser Leu Gly

```
                20                  25                  30

Leu Asn Asn Thr Val Asn Asn Leu Ser Ala Ala Arg Ser Arg Ile Glu
        35                  40                  45

Asp Ala Asp Tyr Ala Thr Glu Val Ser Asn Met Ser Arg Gly Gln Ile
    50                  55                  60

Leu Gln Gln Ala Gly Thr Ala Val Leu Ala Gln Ala Asn Gln Val Pro
65                  70                  75                  80

Gln Asn Val Met Ser Leu Leu Arg
                85

<210> SEQ ID NO 90
<211> LENGTH: 89
<212> TYPE: PRT
<213> ORGANISM: Rhodobacter sphaeroides

<400> SEQUENCE: 90

Ala Ile Gly Val Ile Asp Val Ala Leu Ser Lys Ile Ser Gln Ser Arg
1               5                   10                  15

Ser Glu Leu Gly Ala Val Ser Asn Arg Leu Asp Ser Thr Ile Ser Asn
                20                  25                  30

Leu Thr Asn Ile Ser Thr Ser Val Gln Ala Ala Lys Ser Gln Val Met
        35                  40                  45

Asp Ala Asp Phe Ala Ala Glu Ser Thr Asn Leu Ala Arg Ser Gln Ile
    50                  55                  60

Leu Ser Gln Ala Ser Thr Ala Met Leu Ala Gln Ala Asn Ser Ser Lys
65                  70                  75                  80

Gln Asn Val Leu Ser Leu Leu Arg Gly
                85

<210> SEQ ID NO 91
<211> LENGTH: 88
<212> TYPE: PRT
<213> ORGANISM: Xenorhabdus nematophila

<400> SEQUENCE: 91

Pro Leu Asp Thr Leu Asp Lys Ala Leu Ala Gln Val Asp Asp Met Arg
1               5                   10                  15

Ser Ser Leu Gly Ala Val Gln Asn Arg Leu Glu Ser Thr Val Asn Asn
                20                  25                  30

Leu Asn Asn Thr Val Asn Asn Leu Ser Ala Ala Arg Ser Arg Ile Glu
        35                  40                  45

Asp Ala Asp Tyr Ala Val Glu Val Ser Asn Met Ser Arg Gly Gln Ile
    50                  55                  60

Leu Gln Gln Ala Gly Thr Ser Val Leu Ala Gln Ala Asn Gln Val Pro
65                  70                  75                  80

Gln Thr Val Leu Ser Leu Leu Arg
                85

<210> SEQ ID NO 92
<211> LENGTH: 88
<212> TYPE: PRT
<213> ORGANISM: Proteus mirabilis

<400> SEQUENCE: 92

Ala Leu Ala Thr Leu Asp Asn Ala Ile Ser Lys Val Asp Glu Ser Arg
1               5                   10                  15

Ser Lys Leu Gly Ala Ile Gln Asn Arg Phe Gln Ser Thr Ile Asn Asn
                20                  25                  30
```

```
Leu Asn Asn Thr Val Asn Asn Leu Ser Ala Ser Arg Ser Arg Ile Leu
            35                  40                  45

Asp Ala Asp Tyr Ala Thr Glu Val Ser Asn Met Ser Lys Asn Gln Ile
 50                  55                  60

Leu Gln Gln Ala Gly Thr Ala Val Leu Ala Gln Ala Asn Gln Val Pro
 65                  70                  75                  80

Gln Thr Val Leu Ser Leu Leu Arg
                85
```

<210> SEQ ID NO 93
<211> LENGTH: 88
<212> TYPE: PRT
<213> ORGANISM: Butyrivibrio fibrisolvens

<400> SEQUENCE: 93

```
Ala Ile Asp Ala Ile Ser Asp Ala Leu Ala Lys Val Ser Ala Gln Arg
 1               5                  10                  15

Ser Ala Leu Gly Ser Ile Gln Asn Arg Leu Glu His Ser Ile Ala Asn
            20                  25                  30

Leu Asp Asn Val Val Glu Asn Thr Asn Ala Ala Glu Ser Arg Ile Arg
            35                  40                  45

Asp Thr Asp Met Ala Asp Glu Met Val Thr Tyr Ser Lys Asn Asn Ile
 50                  55                  60

Leu Met Gln Ala Gly Gln Ser Met Leu Ala Gln Ala Asn Gln Ala Thr
 65                  70                  75                  80

Gln Gly Val Leu Ser Ile Leu Gln
                85
```

<210> SEQ ID NO 94
<211> LENGTH: 88
<212> TYPE: PRT
<213> ORGANISM: Bordetella pertussis

<400> SEQUENCE: 94

```
Ala Leu Ser Lys Leu Asp Asp Ala Met Lys Ala Val Asp Glu Gln Arg
 1               5                  10                  15

Ser Ser Leu Gly Ala Ile Gln Asn Arg Phe Glu Ser Thr Val Ala Asn
            20                  25                  30

Leu Asn Asn Thr Ile Thr Asn Leu Ser Ala Ala Arg Ser Arg Ile Glu
            35                  40                  45

Asp Ser Asp Tyr Ala Thr Glu Val Ser Asn Met Thr Lys Asn Gln Ile
 50                  55                  60

Leu Gln Gln Ala Gly Thr Ser Val Leu Ala Gln Ala Asn Gln Val Pro
 65                  70                  75                  80

Gln Asn Val Leu Ser Leu Leu Arg
                85
```

<210> SEQ ID NO 95
<211> LENGTH: 88
<212> TYPE: PRT
<213> ORGANISM: Clostridium chauvoei

<400> SEQUENCE: 95

```
Ser Ile Lys Thr Ile Asn Ser Ala Ile Glu Gln Val Ser Thr Gln Arg
 1               5                  10                  15

Ser Lys Leu Gly Ala Val Gln Asn Arg Leu Glu His Thr Ile Asn Asn
            20                  25                  30
```

```
Leu Asn Thr Ser Ser Glu Asn Leu Thr Ala Ala Glu Ser Arg Val Arg
             35                  40                  45

Asp Val Asp Met Ala Lys Glu Met Met Ala Phe Ser Lys Asn Asn Ile
 50                  55                  60

Leu Ser Gln Ala Ala Gln Ala Met Leu Gly Gln Ala Asn Gln Pro
 65                  70                  75                  80

Gln Gly Val Leu Gln Leu Leu Arg
                 85
```

<210> SEQ ID NO 96
<211> LENGTH: 88
<212> TYPE: PRT
<213> ORGANISM: Xanthomonas campestris

<400> SEQUENCE: 96

```
Ala Leu Glu Ile Val Asp Lys Ala Leu Thr Ser Val Asn Ser Ser Arg
 1               5                  10                  15

Ala Asp Met Gly Ala Val Gln Asn Arg Phe Thr Ser Thr Ile Ala Asn
             20                  25                  30

Leu Ala Ala Thr Ser Glu Asn Leu Thr Ala Ser Arg Ser Arg Ile Ala
             35                  40                  45

Asp Thr Asp Tyr Ala Lys Thr Thr Ala Glu Leu Thr Arg Thr Gln Ile
 50                  55                  60

Leu Gln Gln Ala Gly Thr Ala Met Leu Ala Gln Ala Lys Ser Val Pro
 65                  70                  75                  80

Gln Asn Val Leu Ser Leu Leu Gln
                 85
```

<210> SEQ ID NO 97
<211> LENGTH: 84
<212> TYPE: PRT
<213> ORGANISM: Nitrosomonas europaea

<400> SEQUENCE: 97

```
Ile Asp Asp Ala Leu Lys Ile Val Asn Ser Thr Arg Ala Asp Leu Gly
 1               5                  10                  15

Ala Ile Gln Asn Arg Phe Ser Ser Ala Ile Ala Asn Leu Gln Thr Ser
             20                  25                  30

Ala Glu Asn Leu Ser Ala Ser Arg Ser Arg Ile Gln Asp Ala Asp Phe
             35                  40                  45

Ala Ala Glu Thr Ala Ala Leu Thr Arg Ala Gln Ile Leu Gln Gln Ala
 50                  55                  60

Gly Val Ala Met Leu Ser Gln Ala Asn Ala Leu Pro Asn Asn Val Leu
 65                  70                  75                  80

Ser Leu Leu Arg
```

<210> SEQ ID NO 98
<211> LENGTH: 88
<212> TYPE: PRT
<213> ORGANISM: Campylobacter lari

<400> SEQUENCE: 98

```
Val Met Asp Ile Ala Asp Thr Ala Ile Ala Asn Leu Asp Thr Ile Arg
 1               5                  10                  15

Ala Asn Ile Gly Ala Thr Gln Asn Gln Ile Thr Ser Thr Ile Asn Asn
             20                  25                  30

Ile Ser Val Thr Gln Val Asn Val Lys Ala Ala Glu Ser Gln Ile Arg
             35                  40                  45
```

```
Asp Val Asp Phe Ala Ser Glu Ser Ala Asn Tyr Ser Lys Ala Asn Ile
    50                  55                  60

Leu Ala Gln Ser Gly Ser Tyr Ala Met Ala Gln Ala Asn Ala Ala Ser
65                  70                  75                  80

Gln Asn Val Leu Arg Leu Leu Gln
                85
```